US012609215B2

(12) United States Patent
deBock et al.

(10) Patent No.: US 12,609,215 B2
(45) **Date of Patent: \*Apr. 21, 2026**

(54) FRACTURE RESISTANT STIMULATION LEAD

(71) Applicant: SPR THERAPEUTICS, INC., Cleveland, OH (US)

(72) Inventors: Matthew deBock, Morrisville, OH (US); Joseph Boggs, III, Carrboro, NC (US); Nathan Crosby, Cleveland, OH (US); Brandon Swan, Cleveland, OH (US); Devin Sell, Brecksville, OH (US); Bryce Dimit, Cleveland, OH (US)

(73) Assignee: SPR THERAPEUTICS, INC., Cleveland, OH (US)

( * ) Notice: Subject to any disclaimer, the term of this patent is extended or adjusted under 35 U.S.C. 154(b) by 349 days.

This patent is subject to a terminal disclaimer.

(21) Appl. No.: 18/226,309

(22) Filed: Jul. 26, 2023

(65) Prior Publication Data

US 2023/0411038 A1 Dec. 21, 2023

Related U.S. Application Data

(63) Continuation of application No. 18/008,479, filed as application No. PCT/US2022/037317 on Jul. 15, 2022, now Pat. No. 11,742,106.

(Continued)

(51) Int. Cl.
*H01B 7/00* (2006.01)
*A61N 1/05* (2006.01)
*H01B 7/04* (2006.01)

(52) U.S. Cl.
CPC ......... *H01B 7/0009* (2013.01); *A61N 1/0558* (2013.01); *H01B 7/048* (2013.01)

(58) Field of Classification Search
None
See application file for complete search history.

(56) References Cited

U.S. PATENT DOCUMENTS

| | | | | |
|---|---|---|---|---|
| 22,922 | A | * 2/1859 | Maynard | H01B 3/008 |
| | | | | 174/121 R |
| 817,328 | A | * 4/1906 | Lloyd | D07B 7/025 |
| | | | | 174/126.1 |

(Continued)

OTHER PUBLICATIONS

Patent Cooperation Treaty (PCT), International Search Report and Written Opinion for Application PCT/US2022/037317 filed Jul. 15, 2022, mailed Oct. 4, 2022, International Searching Authority, US.

*Primary Examiner* — Krystal Robinson
(74) *Attorney, Agent, or Firm* — McDonald Hopkins LLC

(57) ABSTRACT

A lead may comprise a multiple filar wire comprising an inner core, an inner layer and an outer layer, where a portion of the inner layer is wound in a first orientation and the inner layer comprises a first number of filars of wire and where a portion of the outer layer is wound in a second orientation opposite the first orientation and the outer layer comprises a second number of filars of wire, the second number of filars of wire being greater than the first number of filars of wire. The lead may also comprise insulation covering a portion of the multiple filar wire, the portion of the multiple filar wire and the insulation comprising a helical coil structure wound in the first orientation and an anchor formed by the inner core, inner layer and outer layer extending away from the portion of the multiple filar wire, wherein the anchor comprises no helical coil structure.

37 Claims, 27 Drawing Sheets

Related U.S. Application Data

(60) Provisional application No. 63/255,247, filed on Oct. 13, 2021, provisional application No. 63/222,279, filed on Jul. 15, 2021.

(56) References Cited

U.S. PATENT DOCUMENTS

| | | | | |
|---|---|---|---|---|
| 1,626,776 A * | 5/1927 | Austin | H01B 5/104 | |
| | | | | 174/128.1 |
| 1,852,902 A * | 4/1932 | Rockwell | H01B 11/00 | |
| | | | | 379/90.01 |
| 2,003,990 A * | 6/1935 | Carlson | H01B 7/226 | |
| | | | | 174/117 R |
| 2,018,461 A * | 10/1935 | Morgan | H01B 13/0214 | |
| | | | | 57/309 |
| 2,289,732 A * | 7/1942 | Rosch | H01B 7/285 | |
| | | | | 174/114 R |
| 2,532,135 A * | 11/1950 | Whyland | H01B 3/30 | |
| | | | | 174/128.1 |
| 2,584,027 A * | 1/1952 | Kendrick | H01B 7/046 | |
| | | | | 174/128.1 |
| 2,856,453 A * | 10/1958 | Shepp | H01B 7/041 | |
| | | | | 174/116 |
| 2,886,631 A * | 5/1959 | Muller | H01B 7/226 | |
| | | | | 174/115 |
| 2,956,311 A * | 10/1960 | Raydt | B29C 48/12 | |
| | | | | 156/244.14 |
| 2,967,902 A * | 1/1961 | Pasini | H01B 9/027 | |
| | | | | 174/2 |
| 2,978,530 A * | 4/1961 | Braeckman | H01B 13/02 | |
| | | | | 174/128.1 |
| 3,155,769 A * | 11/1964 | Burley | H01B 7/041 | |
| | | | | 174/124 R |
| 3,164,669 A * | 1/1965 | Meyerhoff | H01B 7/303 | |
| | | | | 174/114 R |
| 3,233,032 A * | 2/1966 | Crowdes | H01B 9/027 | |
| | | | | 174/24 |
| 3,604,833 A * | 9/1971 | Beck | H01B 12/08 | |
| | | | | 174/29 |
| 3,679,812 A * | 7/1972 | Owens | H01B 7/226 | |
| | | | | 174/29 |
| 3,683,103 A * | 8/1972 | Mancino | H01B 7/0009 | |
| | | | | 174/126.2 |
| 3,717,987 A * | 2/1973 | Gilmore | D07B 5/007 | |
| | | | | 57/215 |
| 3,749,813 A * | 7/1973 | Shealy | H02G 7/14 | |
| | | | | 174/42 |
| 3,866,670 A * | 2/1975 | Cramer | F16L 53/70 | |
| | | | | 165/47 |
| 4,125,741 A * | 11/1978 | Wahl | H01B 7/0009 | |
| | | | | 174/113 A |
| 4,683,349 A * | 7/1987 | Takebe | H01B 7/0009 | |
| | | | | 174/113 C |
| 5,449,861 A * | 9/1995 | Fujino | H01B 13/0285 | |
| | | | | 174/113 A |
| 7,168,165 B2 | 1/2007 | Calzada et al. | | |
| 7,205,479 B2 * | 4/2007 | Caveney | H01B 11/04 | |
| | | | | 174/113 AS |
| 8,639,352 B2 | 1/2014 | Wang et al. | | |
| 8,996,134 B2 | 3/2015 | Duncan et al. | | |
| 9,659,679 B2 | 5/2017 | Mcintyre et al. | | |
| 9,901,731 B2 * | 2/2018 | Marshall | A61N 1/3718 | |
| 2008/0262584 A1 * | 10/2008 | Bottomley | A61N 1/0488 | |
| | | | | 29/605 |
| 2009/0270956 A1 | 10/2009 | Vase et al. | | |
| 2010/0174348 A1 | 7/2010 | Bulkes et al. | | |
| 2011/0079423 A1 * | 4/2011 | Zhao | A61N 1/056 | |
| | | | | 336/208 |
| 2011/0253415 A1 * | 10/2011 | Muschiatti | H01B 11/1821 | |
| | | | | 174/107 |
| 2012/0136419 A1 * | 5/2012 | Zarembo | A61N 1/05 | |
| | | | | 607/116 |
| 2012/0232625 A1 * | 9/2012 | Sage | A61N 1/0551 | |
| | | | | 607/116 |
| 2012/0271386 A1 * | 10/2012 | Li | C22F 1/183 | |
| | | | | 607/116 |
| 2013/0110215 A1 * | 5/2013 | Fan | A61N 1/362 | |
| | | | | 977/925 |
| 2013/0341065 A1 * | 12/2013 | Sato | H01B 11/1895 | |
| | | | | 174/107 |
| 2018/0339139 A1 | 11/2018 | Boucher et al. | | |

* cited by examiner

102

108

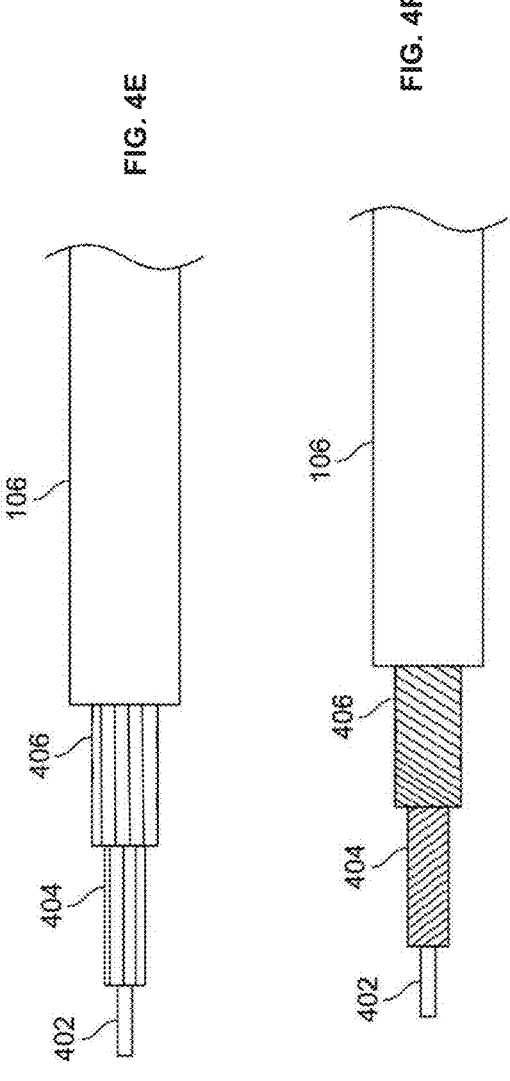

Status   ○ Intact   △ Fractured (Electrode)   × Fractured (Insulation)

Insulation
Wall Thickness

Strand
(Group of Filars)

Individual Filar (Metal
Conductor)
(Filars are also called Filaments)

A Group of Strands would be a Cable.
A Cable could also be made of a
single strand

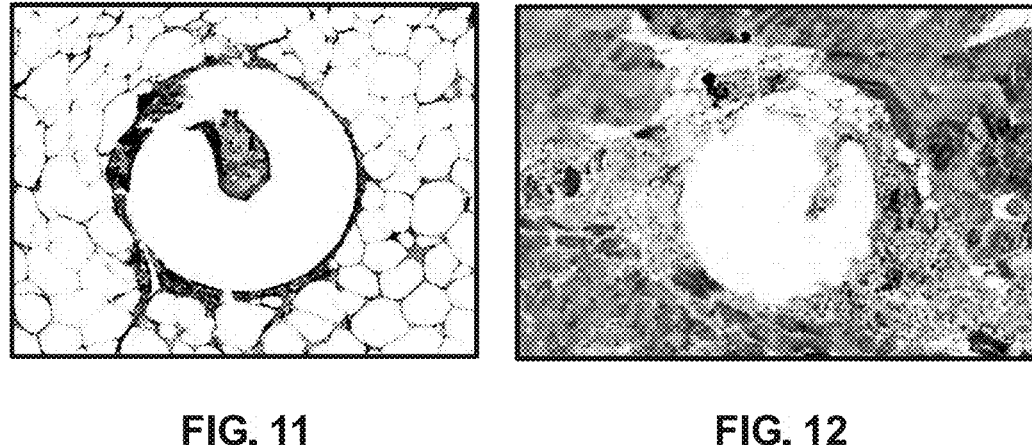
FIG. 11                    FIG. 12
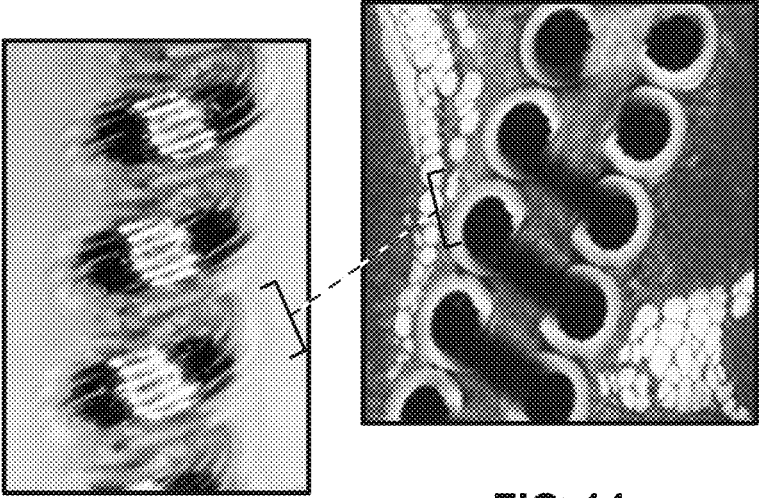
Fibrotic
Ingrowth into
open coils
(longitudinal)
FIG. 14
FIG. 13

Tensile Forces

Bending Forces

Shear Forces

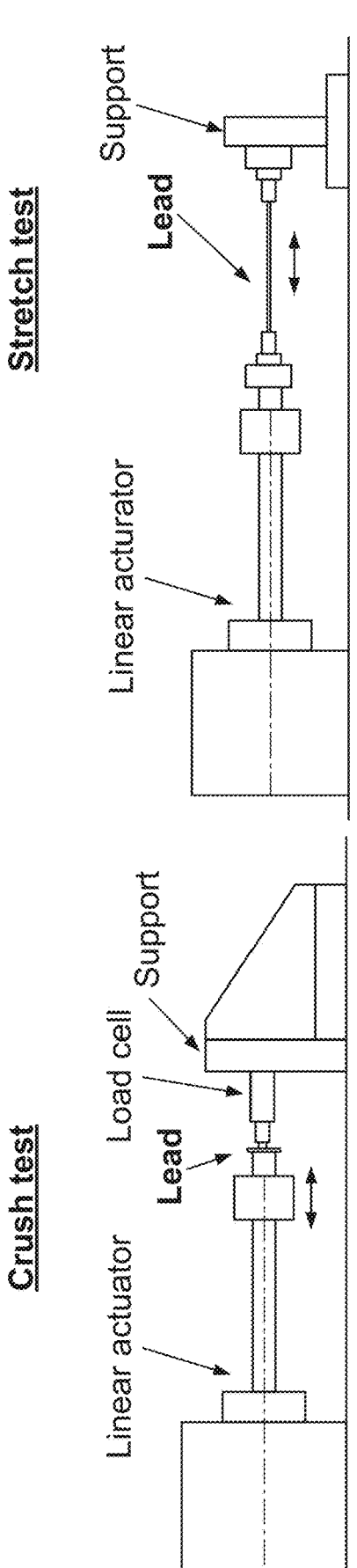
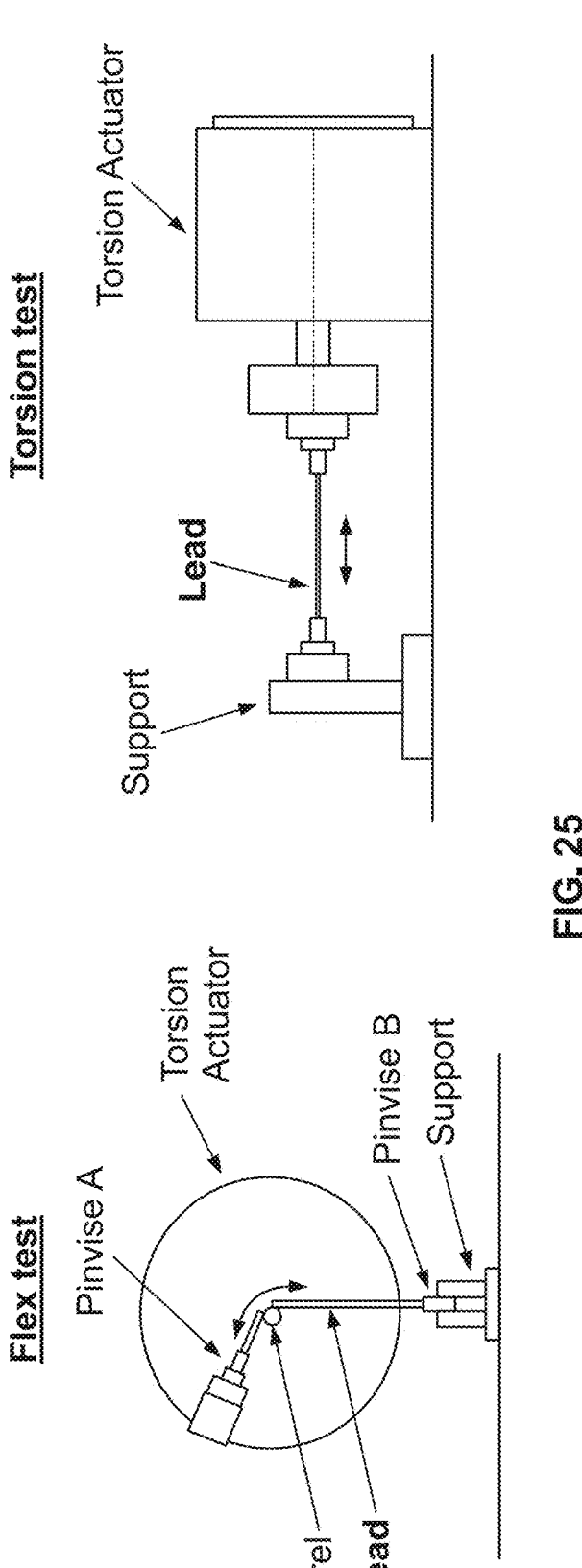
FIG. 25

Prior Art - Ductile Fracture at Lead Removal

Prior Art – Ductile Fracture at Lead Removal Replicated with Tensile Bench Testing Prior Art - Fatigue Fracture During Treatment Prior Art – Fatigue Fracture Replicated with Shear Bench Testing

FRACTURE RESISTANT STIMULATION LEAD

CROSS REFERENCE TO RELATED APPLICATIONS

This application is a continuation of U.S. Utility application Ser. No. 18/008,479, filed on Dec. 6, 2022, entitled "FRACTURE RESISTANT STIMULATION LEAD" which is a 35 U.S.C. § 371 national stage application of PCT Application No. PCT/US2022/037317 filed on Jul. 15, 2022 entitled "FRACTURE RESISTANT STIMULATION LEAD" which claims priority to U.S. Patent Application No. 63/222,279, filed on Jul. 15, 2021, entitled "Fracture Resistant Stimulation Lead," and claims priority to U.S. Patent Application No. 63/255,247, filed on Oct. 13, 2021, entitled "Fracture Resistant Stimulation Lead," which are incorporated herein by reference.

TECHNICAL FIELD

The present invention is generally related to stimulation leads configured for temporary implantation, and more specifically, a fracture resistant stimulation lead used for percutaneous electrical stimulation.

BACKGROUND

Neurostimulation can provide functional and/or therapeutic outcomes. Some stimulation therapies are designed to use stimulation leads that are temporarily implanted into a patient through non-surgical means, such as by being percutaneously inserted into the patient. Because these leads are implanted on a temporary basis, the considerations and design decisions for the configuration of the stimulation lead are substantially different than surgically implanted permanent anchored leads used in other stimulation-based therapies, such as spinal cord stimulation (SCS). For example, the leads implanted on a temporary basis are usually partially exposed to the environment (e.g., exterior to the patient) and need to be flexible enough to move as a patient moves, but rigid enough to remain in the target area without drifting or pistoning. Additionally, these leads need to be implantable and removable without surgical intervention such that the lead remains in place while implanted and can be removed without much discomfort to the patient.

There is a need, therefore, for a stimulation lead with these qualities that also has a greater resistance to fracturing during use and removal.

SUMMARY

A fracture resistant stimulation lead(s) is/are described below. The stimulation lead may be temporarily implanted to facilitate delivering stimulation to a nerve innervating a region. An example stimulation lead for temporary insertion into a patient includes a multiple filar wire. The multiple filar wire has an inner core, an inner layer, and an outer layer. The inner layer has a first number of filars and has a winding in a first orientation. The outer layer has a second number of filars and has a winding in a second orientation opposite the first orientation. The second number of filars is greater than the first number of filars. Insulation covers a portion of the multiple filar wire. The multiple filar wire and the insulation having a helical coil structure having the first orientation. Additionally, the example stimulation lead may include an anchor formed by the inner core extending from the multiple filar wire. While a portion of the lead advantageously has a helical coil structure, the anchor advantageously has no helical coil structure. Further still, a portion of the stimulation lead may comprise a de-insulated portion at a distal end that forms the electrode.

Alternatively, the stimulation lead may include all or a portion of the wire filars that are not coiled, e.g., has no wrapped or helical coil structure. Further, the example stimulation lead may include a deinsulated portion that is immediately adjacent to the anchor wherein the deinsulated portion forms an electrode through which the stimulation energy is transferred to the patient.

A lead may comprise a multiple filar wire comprising an inner core, an inner layer and an outer layer, where a portion of the inner layer is wound in a first orientation and the inner layer comprises a first number of filars of wire and where a portion of the outer layer is wound in a second orientation opposite the first orientation and the outer layer comprises a second number of filars of wire, the second number of filars of wire being greater than the first number of filars of wire. The lead may also comprise insulation covering a portion of the multiple filar wire, the portion of the multiple filar wire and the insulation comprising a helical coil structure wound in the first orientation and an anchor formed by the inner core, inner layer and outer layer extending away from the portion of the multiple filar wire, wherein the anchor comprises no helical coil structure.

The foregoing lead may comprise any of the following in any combination:

the anchor is bent relative to the portion of the multiple filar wire between about 40 degrees and 100 degrees.
  the anchor is bent relative to the portion of the multiple filar wire at about 90 degrees.
  the anchor is bent relative to the portion of the multiple filar wire between about 40 degrees and 90 degrees.
  the anchor is bent relative to the portion of the multiple filar wire at about 70 degrees.
  the first number of filars of wire comprises six filars of wire.
  the second number of filars of wire comprises twelve filars of wire.
  a ball attached to an end of the anchor, wherein the ball prevents the inner core, inner layer and the outer layer from coming apart.
  the first orientation comprises a left-hand lay.
  the first orientation comprises a right-hand lay.
  the multiple filar wire is formed from 316LVM stainless steel.
  a length of the multiple filar is free of insulation and comprises the helical coil structure wound in the first orientation and the length of the multiple filar comprises an electrode.

A lead may comprise an inner core, an inner layer comprising a first number of filars, where a portion of a length of the inner layer is wound in a first orientation and an outer layer comprising a second number of filars, where a portion of a length of the outer layer is wound in a second orientation opposite the first orientation, the second number of filars being greater than the first number of filars. The lead may also comprise insulation covering a second portion of the length of the outer layer, where the portion of the length of the outer layer, the portion of the length of the inner layer and the insulation comprise a helical coil structure wound in the first orientation, and an anchor formed by a portion of a length of the inner core, a third portion of the length of the inner layer and a third portion of the length of outer layer, where the anchor comprises no helical coil structure.

The foregoing lead may comprise any of the following in any combination:

a distance between the portion of the length of the outer layer and the third portion of the length of the outer layer is free of insulation and comprises the helical coil structure wound in the first orientation and the distance comprises an electrode.

the anchor is bent relative to the helical coil structure between about 40 degrees and 100 degrees.

the anchor is bent relative to the helical coil structure at about 90 degrees.

the anchor is bent relative to the helical coil structure between about 40 degrees and 90 degrees.

the anchor is bent relative to the helical coil structure at about 70 degrees.

the first number of filars comprises six filars.

the second number of filars comprises twelve filars.

a ball attached to an end of the anchor, wherein the ball prevents the inner core, inner layer and the outer layer from coming apart.

the first orientation comprises a left-hand lay.

the first orientation comprises a right-hand lay.

the inner core, inner layer and outer layer are formed from 316LVM stainless steel.

A lead may comprise an inner core comprising a single filar, an inner layer comprising a first number of filars a portion of a length of the inner layer is wound in a first orientation around the inner core, and an outer layer comprising a second number of filars a portion of a length of the outer layer is wound in a second orientation opposite the first orientation, the second number of filars being greater than the first number of filars. The lead may also comprise insulation covering a second portion of the length of the outer layer and inner layer and a portion of a length of the inner core, where the insulation the second portion of the length of the outer layer and inner layer and the portion of a length of the inner core comprise a helical coil structure wound in the first orientation, and an anchor formed by a third portion of the length of the inner core, a third portion of the length of the inner layer and a second portion of the length of outer layer, where the anchor comprises no helical coil structure.

The foregoing lead may comprise any of the following in any combination:

a distance between the portion of the length of the outer layer and the third portion of the length of the outer layer is free of insulation and comprises the helical coil structure wound in the first orientation and the distance comprises an electrode.

the anchor is bent relative to the helical coil structure between about 40 degrees and 100 degrees.

the anchor is bent relative to the helical coil structure at about 90 degrees.

the anchor is bent relative to the helical coil structure between about 40 degrees and 90 degrees.

the anchor is bent relative to the helical coil structure at about 70 degrees.

the first number of filars comprises six filars.

the second number of filars comprises twelve filars.

a ball attached to an end of the anchor, wherein the ball prevents the inner core, inner layer and the outer layer from coming apart.

the first orientation comprises a left-hand lay.

the first orientation comprises a right-hand lay.

the inner core, inner layer and outer layer are formed from 316LVM stainless steel.

BRIEF DESCRIPTION OF THE DRAWINGS

Operation of the present disclosure may be better understood by reference to the following detailed description taken in connection with the following illustrations, wherein:

FIGS. 4E, 4F, 4G, and 4H illustrate various aspects of a multi-filar wire used to form the stimulation lead, in accordance with the teachings of this disclosure.

FIG. 11 depicts a histology section of animal tissue with tissue ingrowth into an open coil, in accordance with the teachings of this disclosure.

FIG. 12 depicts a histology section of animal tissue with tissue ingrowth into an open coil, in accordance with the teachings of this disclosure.

FIG. 13 depicts an insulated multi-filar wire formed into an open coil configuration in accordance with the teachings of this disclosure.

FIG. 14 depicts fibrotic ingrowth into the open coils of an insulated multi-filar wire formed into an open coil configuration in accordance with the teachings of this disclosure.

FIG. 25 are exemplary side views of various testing apparatuses for performing a crush test, stretch test, flex test and torsion test on a stimulation lead of an embodiment of the present disclosure.

DETAILED DESCRIPTION

Figure 1:
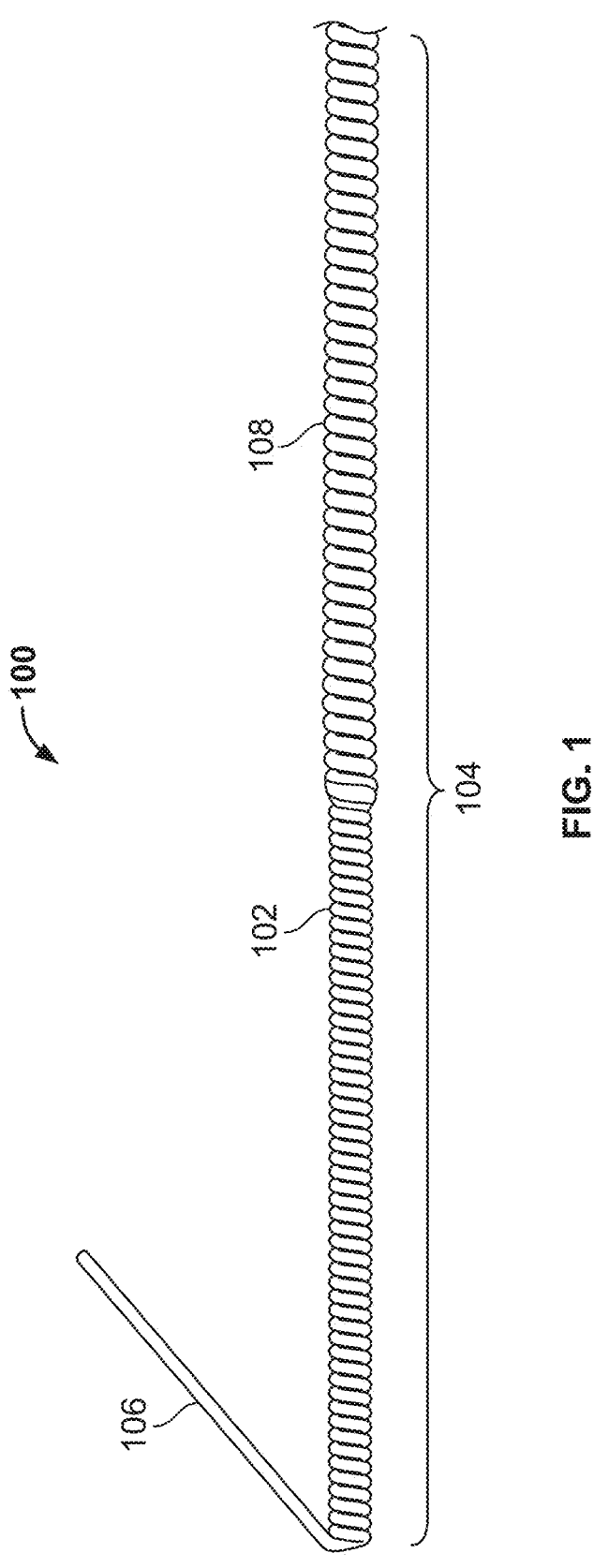
FIG. 1 illustrates a stimulation lead configured to be temporarily implanted into a patient for electrical nerve stimulation, in accordance with the teachings of this disclosure.

Reference will now be made in detail to exemplary embodiments of the present disclosure, examples of which are illustrated in the accompanying drawings. It is to be understood that other embodiments may be utilized, and structural and functional changes may be made without departing from the respective scope of the present disclosure. Moreover, features of the various embodiments may be combined or altered without departing from the scope of the present disclosure. As such, the following description is presented by way of illustration only and should not limit in any way the various alternatives and modifications that may be made to the illustrated embodiments and still be within the spirit and scope of the present disclosure.

As used herein, the words "example" and "exemplary" mean an instance, or illustration. The words "example" or "exemplary" do not indicate a key or preferred aspect or embodiment. The word "or" is intended to be inclusive rather an exclusive, unless context suggests otherwise. As an example, the phrase "A employs B or C," includes any inclusive permutation (e.g., A employs B; A employs C; or A employs both B and C). As another matter, the articles "a" and "an" are generally intended to mean "one or more" unless context suggests otherwise.

As disclosed below, a stimulation lead (sometimes referred to as a "micro-lead," a "fine-wire lead," or an "electrode") is formed of a multi-filar wire to facilitate being implanted (especially percutaneously) in a patient on a temporary basis (e.g., for one or more days, weeks, or months, such as for 14, 15, 30, and/or 60 days, etc.) or on a more permanent basis (e.g., multiple years). The stimulation lead of the present disclosure may be used in conjunction with a device, such as an electrical stimulation device, to deliver therapeutic electrical stimulation (e.g. peripheral nerve stimulation (PNS)) to a nerve (e.g., peripheral nerve) innervating the region of pain to provide pain relief, such as that disclosed in U.S. Pat. Nos. 10,166,384, 10,981,005 and 10,668,285, which are incorporated herein by reference. For example, the stimulation lead may be temporarily percutaneously implanted to facilitate delivering stimulation to a nerve innervating a region, where the region may be painful (e.g., with chronic, acute, post-surgical or another type of pain) or be anticipated to be painful due to a surgery (e.g., placement of a lead may facilitate delivering stimulation to a femoral nerve, sciatic nerve, or lumbar plexus innervating a region, such as a knee which may be undergoing knee replacement surgery) or otherwise.

Because the percutaneous stimulation lead described herein may be implanted on a temporary basis (e.g., via an introducer needle, etc.), the considerations and design decisions for the configuration of the stimulation lead are substantially different than surgically implanted permanent anchored leads used in other stimulation-based therapies, such as spinal cord stimulation (SCS). For example, the stimulation lead described herein is designed to be implanted and removed in an outpatient clinical setting without surgical intervention. This is distinguishable from implanted SCS and other PNS leads that are typically surgically inserted into a body and are removed via a surgical procedure. This means that the configurations of such SCS and PNS leads do not need to match those of the present stimulation lead, such as for example because such SCS and PNS leads are often require surgery to remove (e.g., are not non-surgically removed). Additionally, existing leads that can be removed without surgery do not have the multiple advantages of the present invention.

To be both optimally effective in delivering stimulation for the duration necessary to achieve the desired therapeutic effect and also able to be non-surgically removed, the stimulation lead needs to be (a) flexible enough to remain in place even as the patient moves about their everyday as a portion of the stimulation lead is external to the patient, and (b) not too flexible to cause fatigue to the lead caused by movement of the patient during stimulation. That is, a lead that is too stiff may break under certain use conditions and a lead that is too flexible may break under certain use conditions. For example, a lead that is too stiff but is forced to bend (e.g., while crossing a major muscle plane) may behave in a brittle fashion, resulting in formation of stress cracks in response to the bending action and leading to premature failure of the lead. Alternatively, a lead that is too flexible may be forced to bend to an extreme degree (e.g., while crossing a major muscle plane) and may be subject to stress crack formation in response to the extreme bending induced by movement of the muscles and/or it may be deformed such that it is no longer effective (e.g., because it is too flexible). In the case of a lead that is too flexible, the excess flexibility may also allow the path of the lead to be significantly changed by movement of the tissue, such that the path or route of the lead becomes tortuous. If the path or route of the lead becomes tortuous, it may bind, catch, and/or encourage undesired excess tissue ingrowth, all of which may make withdrawal of the lead difficult or impossible without causing a force that could fracture the lead or cause pain to the patient during removal.

Additionally, the simulation lead needs to have a withdraw or withdrawal force (e.g., the force required to pull the stimulation lead from the patient or the tissue and fully remove the lead without any other intervention) that is high enough to enable the lead to remain in the patient for the period that the lead is intended to be installed and/or used, but not too high as to be painful and difficult to remove (e.g., withdrawal forces may desirably be within a range or a prespecified range (e.g., the range may be >0.5 Newton (N), but <4 N)). Because these factors are inter-related, balancing these factors cannot be achieved by merely substituting one component for another.

Figure 2A:
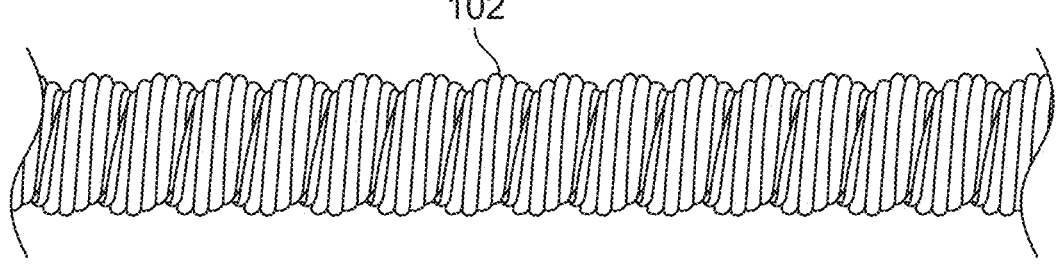
FIG. 2 illustrates an uninsulated portion of the stimulation lead forming an electrode, in accordance with the teachings of this disclosure.
FIG. 2B illustrates an uninsulated portion of the stimulation lead forming an electrode, in accordance with the teachings of this disclosure with a different pitch than that shown in FIG. 2.
FIG. 2C illustrates an uninsulated portion of the stimulation lead forming an electrode, in accordance with the teachings of this disclosure with a different pitch than that shown in FIG. 2.
Figure 3:
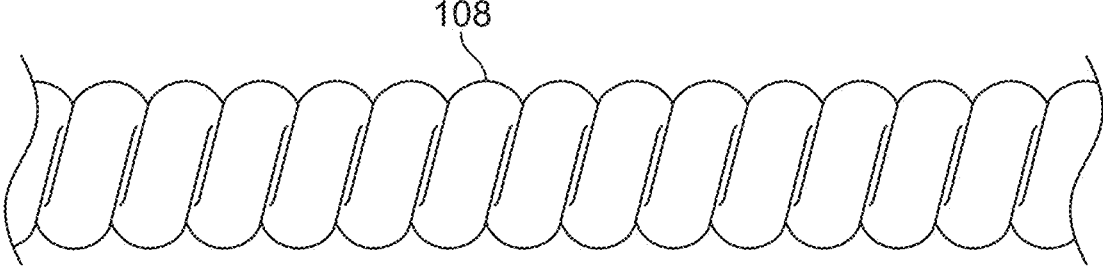
FIG. 3 illustrates an insulated portion of the stimulation lead, in accordance with the teachings of this disclosure.

FIGS. 1, 2, and 3 illustrate various aspects of a stimulation lead 100. As best illustrated in FIG. 1, the stimulation lead 100 includes a multi-filar wire 102 that is formed into a body 104 and an anchor 106. A portion of the body 104 is covered in insulation 108 such that the outer diameter of the stimulation lead is about 300 microns (or micrometers), e.g., within 10% larger or smaller of such target, or desirably 240 to 280 microns. The insulation portion may comprise about 70 microns, e.g., within 10% larger or smaller of such target, or desirably 50 to 70 microns. The anchor 106 is formed on a distal end of the stimulation lead 100. In some examples, the proximal end of the stimulation lead 100 is coupled to a connector (not shown) to electrically couple to a stimulation device. Example connectors are described in International Application No. PCT/US2021/022366, entitled "STIMU-LATION LEAD CONNECTION SYSTEM," filed Mar. 15, 2021, which is hereby incorporated by reference in its entirety.

The body 104 may be coiled, wrapped, wound, formed, shaped, bent, curved, turned, twisted, twined, entwined, curled, circled, rolled, whorled, looped, rotated, structured, molded, forged, fabricated, organized, contrived, fashioned, reworked, and/or spiraled into a helical coil structure. The helical coil structure promotes, for example, a desired level of flexibility and beneficial or desired tissue growth about or around the body 104 to (a) facilitate anchoring the stimulation lead 100, (b) prevent, minimize, and/or inhibit pistoning of the stimulation lead 100 within the patient, and/or (c) prevent, minimize, inhibit, and/or reduce the chance or probability of infection at the insertion site. All but the end of the helical coil structure may be covered in insulation 108. Desirably, the insulation material may be comprised of perfluoroalkoxy (PFA). PFA is a flexible material that is very biocompatible. For example, the last 1 centimeter (cm) of the coil may not be covered by the insulation 108. The helical coil structure is wound in a certain orientation (e.g., a right hand lay, a left hand lay, etc.). As described below, the orientation of the helical coil structure of the body 104 may be determined by the orientation of an inner layer of the multi-filar wire 102.

The anchor 106 extends from the helical coil structure of the body 104 and is or may function monolithically as part of the multi-filar wire 102, e.g., the anchor 106 is formed from the multi-filar wire 102 or more specifically, may be formed from one or more of the multi-filar wires 102. In other embodiments, the anchor 106 may be formed from two or more, e.g., 2-19, of the multi-filar wires 102. The multi-filar wires 102 may be of about 160 microns, e.g., 10% larger or smaller of such target. The anchor 106 may form part of or in some embodiments all of the electrode that delivers the stimulation to the target area and also facilitates maintaining the position of the stimulation lead 100 within the body of the patient. In some examples, the anchor 106 is about 0.5 cm long, e.g., 10% larger or smaller of such target. The anchor 106 may be generally straight (e.g., within 5-15 degrees of flat/horizontal) and does not have a helical coil structure but instead is formed from the wire(s), filar(s), and/or filament(s) or a single wire filar, and/or filament of the helical coil structure of the body 104 not being wrapped into a helical coil structure. This results in the generally straight anchor 106 or an anchor with a straight portion (e.g., the anchor may be formed from a wire that is composed of filars or multiple layers of filars that have been wound (e.g., in opposing directions or in the same direction) but while the wire is formed from wound filars the wire itself is straight or relatively straight, uncoiled, or not coiled). As described below, an anchor with a helical coil structure may cause the withdraw force of the stimulation lead 100 to be too high. The configuration of anchor 106 being straight makes withdrawal of the stimulation lead 100 easier than if the anchor comprises a helical coil end. The anchor 106 configuration provides enough force to keep the stimulation lead 100 in place during application of the therapy while being able to be withdrawn at the conclusion of the therapy in a manner that only requires a reasonable pulling force and does not cause the patient pain during removal.

As best illustrated in FIGS. 4A, 4B, 4C, and 4D, the stimulation lead 100 is constructed from the multi-filar wire 102. For illustrative purposes, the multi-filar wire 102 in FIGS. 4A, 4B, 4C, and 4D does not have the helical coil structure. In the illustrated example, the multiple filar wire 102 is a 1×19 multi-filar wire (i.e., it is formed from 19 separate filars, filaments, or units). In the illustrated example, the multiple filar wire 102 includes an inner core 402, an inner layer 404, and an outer layer 406. The inner layer 404 has a number of filars. For example, in a 1×19 multi-filar wire, the inner layer 404 may have six filars (although it is not limited to six filars but could be between two and ten filars). The winding of the inner layer 404 has an orientation (e.g., a right hand lay, a left hand lay, etc.). In some examples, to provide both flexibility and wear resistance, the orientation of the inner layer 404 is the same as the orientation of the wrapping of the helical coil structure of the body 104, e.g., if the orientation of the inner layer 404 is a right hand lay, the wrapping of the helical coil structure of the body 104 is a right hand coil. If the orientation of the inner layer 404 is a left-hand lay, the wrapping of the helical coil structure of the body 104 is a left hand coil. Alternatively, it may be desirable for the orientation of the inner 404 (or outer 406) layer to be a different (or opposite) orientation of the wrapping of the helical coil structure of the body 104, e.g., if the orientation of the inner 404 (or outer 406) layer is a right hand lay, the wrapping of the helical coil structure of the body 104 may be a left hand lay. As another alternative, it may be desirable for the orientation of the outer 406 (or inner 404) layer to be the same or a different (or opposite) orientation of the wrapping of the helical coil structure of the body 104, e.g., if the orientation of the outer 406 (or inner 404) layer is a right hand lay, the wrapping of the helical coil structure of the body 104 may be a right hand lay or a left hand lay, depending on the needs and desired performance goals and tradeoffs of the stimulation lead 100 and the mechanical requirements for it to function in a desired anatomical location. The outer layer 406 has a number of filars. For example, in a 1×19 multi-filar wire, the outer layer 406 may have twelve filars (although it is not limited to twelve filars but could be between seven and fifteen filars). The winding of the outer layer 406 may have an orientation that is the opposite the orientation of the winding of the inner layer 406.

Figure 24C:
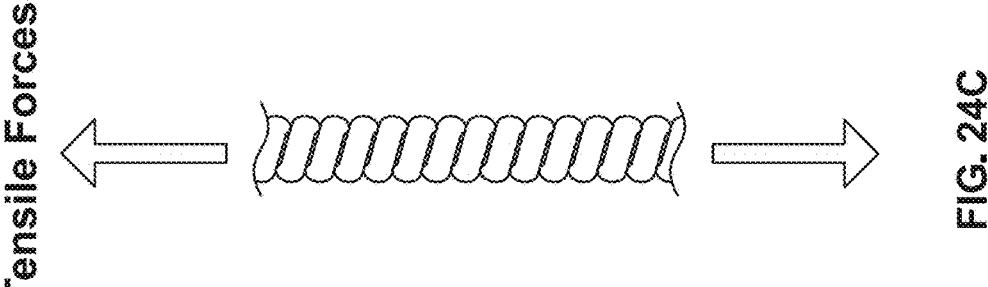
FIG. 24C is a graphical representation of a stimulation lead of an embodiment of the present disclosure under a tensile force.

The foregoing configuration of the stimulation lead 100 was compared against prior art designs through several different tests, which showed that the stimulation lead 100 has certain superior performance functionality. For example, in a shear force cycle bench test the average cycle to failure of the stimulation lead 100 increased by more than five times form that of the prior art design—see for example FIGS. 24A and 25. For example, in the bend force cycle bench test, the average cycles to failure increased by three times for the stimulation lead 100 from that of the prior art version. In the tensile strength bench test, the tensile testing to failure increased by more than two times for the stimulation lead 100 as opposed to the prior art design. Desirably, the lead was designed to enable the withdrawal force to remain in a suitable range to facilitate easy nonsurgical removal. This design goal was met and supported by the observation that the withdrawal force required to remove the lead remained desirably low (e.g., it was able to be maintained at the same desirably low level as that for the prior art design). The present invention enabled a lead design that avoided production of untoward or unwanted observed changes to the fibrotic ingrowth during animal testing (e.g., the tissue or fibrotic ingrowth that the lead produced was desired and facilitated resistance to unwanted movement of the lead while also enabling intact and easy removal of the lead as intended across a range of durations or therapy or treatment periods).

While the anchor 106 may be coiled or wound into a coil, the anchor 106 in an example embodiment, is not coiled or wound into a coil because, while the anchor 106 promotes stability of the stimulation lead 100 when implanted, a coiled structure would promote tissue growth on the anchor and would or could increasingly make the withdraw or withdrawal force of the stimulation lead higher than desired. This phenomenon may be demonstrated through testing of leads in animal models as shown by the results in FIGS. 5 and 6, wherein Design B demonstrates lower average withdrawal forces and no occurrence of fractures with a straight anchor design, while Design C demonstrates increased average withdrawal forces and the occurrence of fractures with a coiled anchor design.

The inner core 402 may comprise a single filar that extends from the body 104 to form the anchor 106. The anchor 106, and thus the inner core 402, is not wound into a coil as it extends from the body 104 because, while the anchor 106 promotes stability of the stimulation lead 100 when implanted, a coiled structure would promote tissue growth on the anchor and would increasingly make the withdraw force of the stimulation lead too high.

In another embodiment, inner core 402 may comprise a number of filars that extend from the body 104 to form the anchor 106. The number may comprise any appropriate number between one and 19 (e.g., 1, 2, 3, 4, 5, 6, 7, 8, 9, 10, 11, 12, 13, 14, 15, 16, 17, 18, and/or 19) or more. In one particular embodiment, the number of filars may comprise 19. The anchor 106, and thus the inner core 402, as with the embodiment disclosed above, is not wound as it extends from the body 104. In these embodiments, the anchor 106 promotes stability of the stimulation lead 100 when implanted but makes withdrawal thereof easier. A structure would promote tissue growth on the anchor that would increasingly make the withdraw force of the stimulation lead too high.

In an alternative, the inner core 402 may comprise a single filar. The anchor 106, however, may be formed from the inner core 402, the inner layer 404 and the outer layer 406 (e.g., all nineteen stands) that are free of insulation (e.g., deinsulated) and are not coiled. That is the anchor 106 is not coiled as is the rest of the stimulation lead 100. More specifically, the insulated portion of the stimulation lead 100 is coiled (as described above) and it transitions to a deinsulated portion that is also coiled as described above. This deinsulated portion may be approximately 1 cm in length (plus or minus up to 0.125, 0.25, 0.5, or 1 cm) and forms the electrode. Alternatively, the deinsulated portion may be approximately 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0 cm in length (plus or minus 10%, 20%, 25%, 30%, 40%, and/or 50%) to form the electrode and/or anchor, This may provide a sufficient surface area of the electrode (e.g., 1 cm$^2$) to provide the therapy described above to relieve pain in the patient while avoiding deleterious impacts possible due to a confined, small, or reduced surface area (e.g., avoiding stimulation induced degradation or corrosion of the stimulating surface in the environment within a body and/or avoiding damage to the tissue). The not-coiled (e.g., straight) anchor 106 extends from the electrode portion and is approximately 0.5 cm in length (plus or minus up to 0.125, 0.25, 0.5, or 1 cm).

Figure 2B:
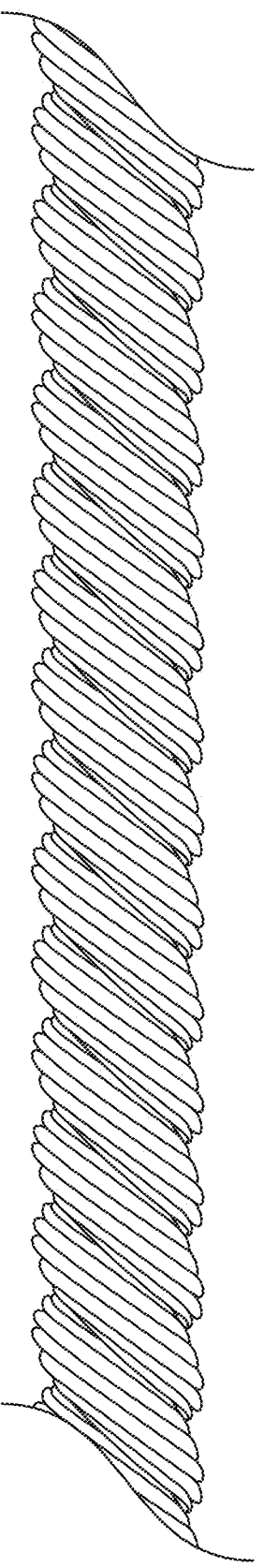
Figure 2C:
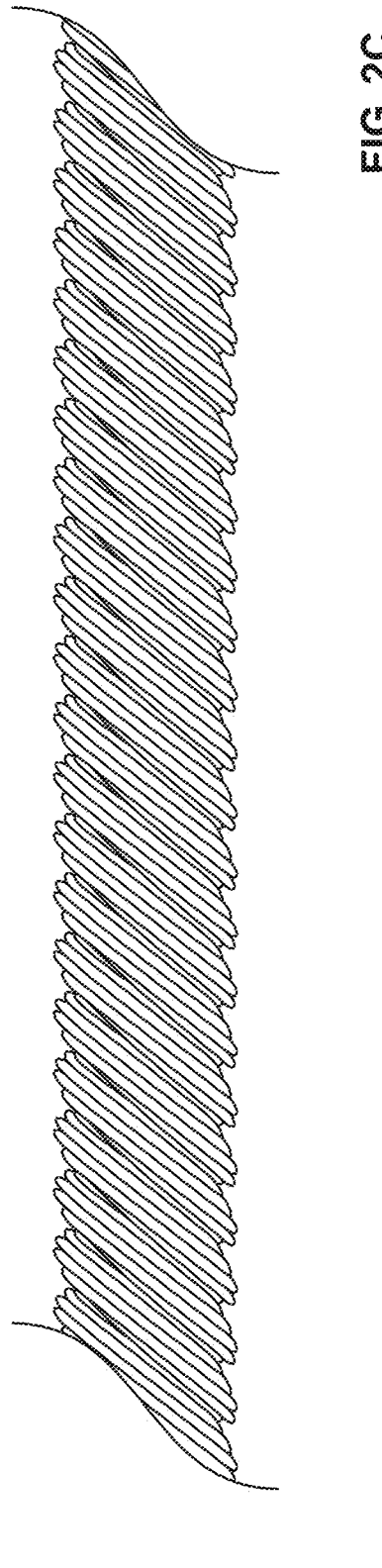
Figure 3B:
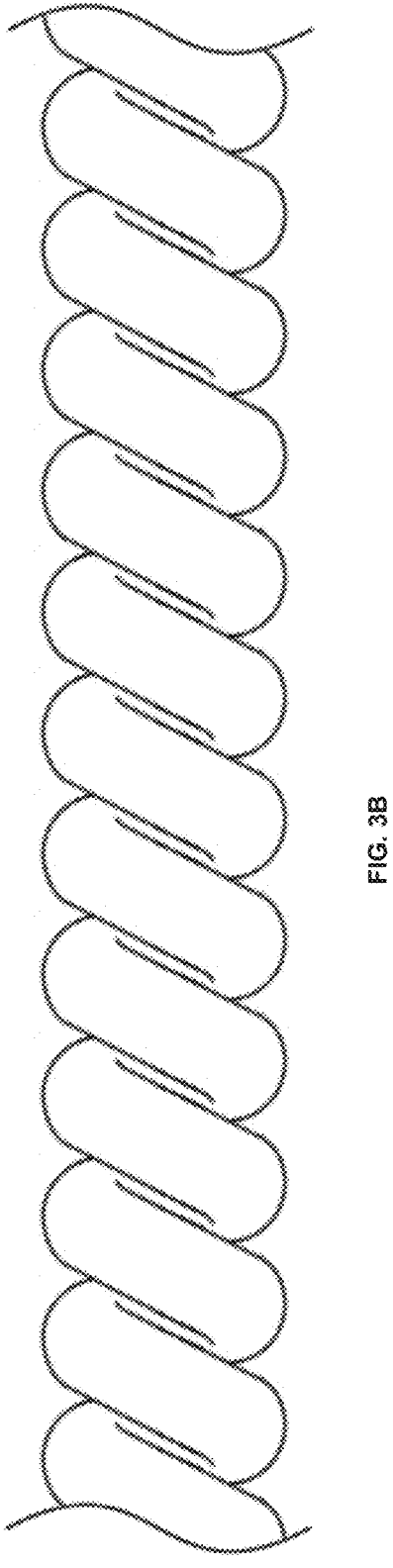
FIG. 3B illustrates an insulated portion of the stimulation lead, in accordance with the teachings of this disclosure with a different coiling pitch than what is shown in FIG. 3.
Figure 4A:
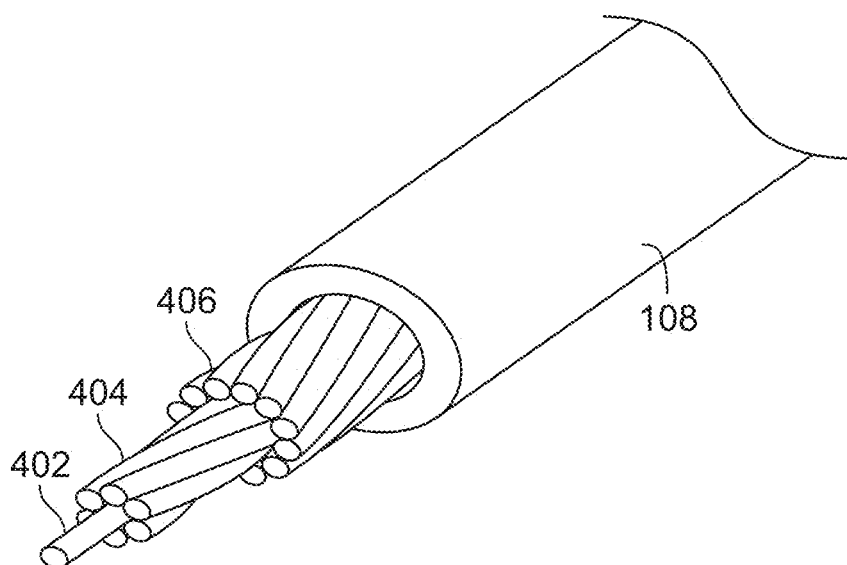
FIGS. 4A, 4B, 4C, and 4D illustrate various aspects of a multi-filar wire used to form the stimulation lead, in accordance with the teachings of this disclosure.
Figure 4B:
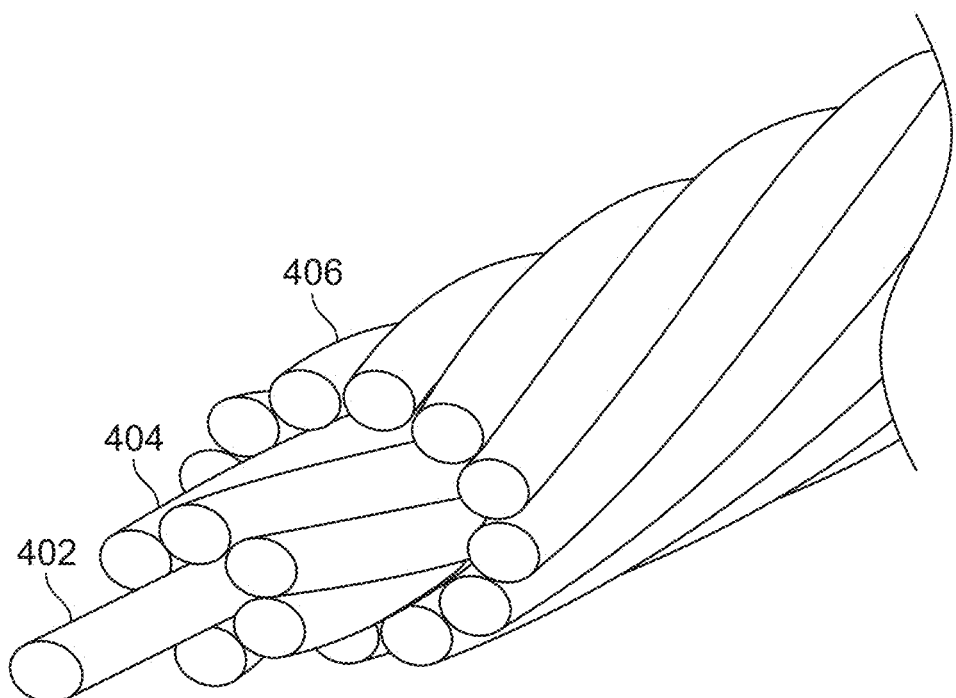
Figure 4C:
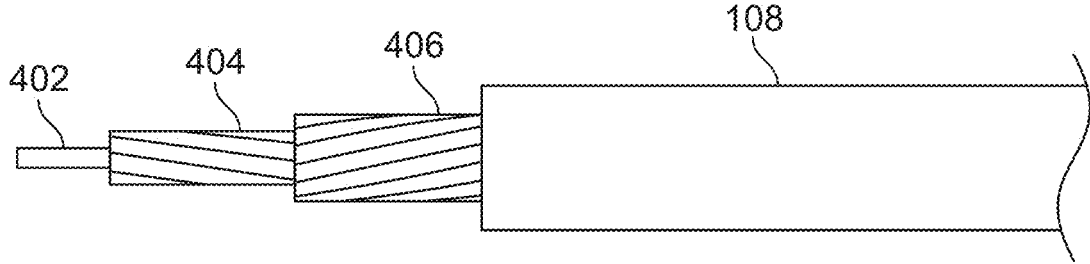
Figure 4D:
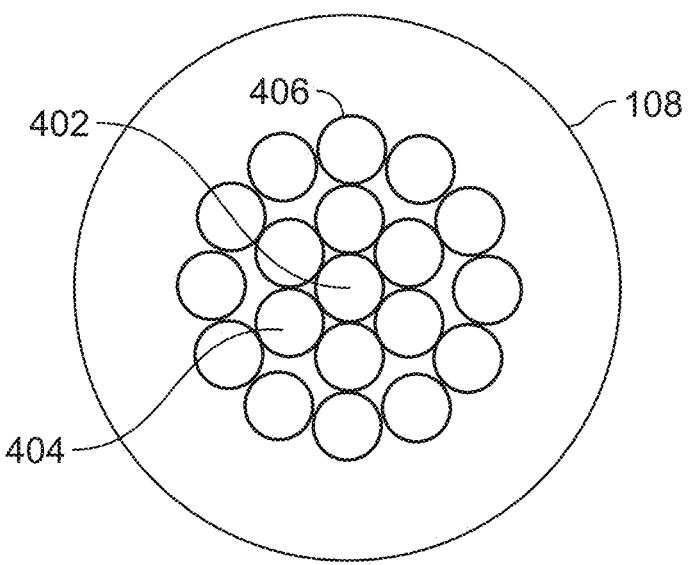
Figure 4H:
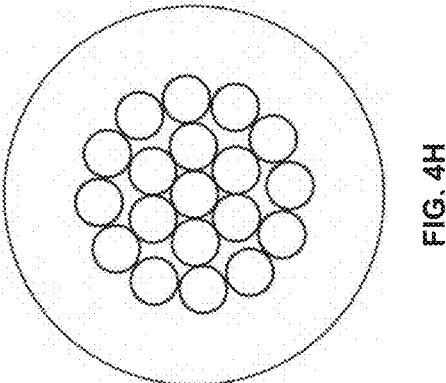
Figure 4G:
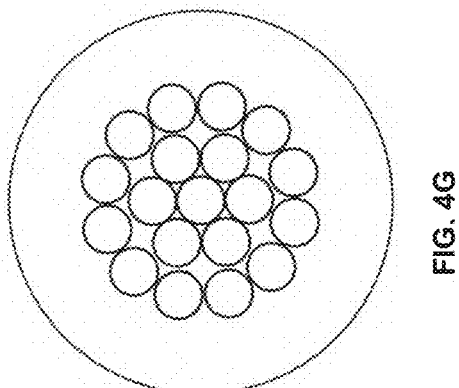

In some embodiments, a distal end 110 of the anchor 106 may include a weld such as a ball weld 114 that generally prevents the filars of wire forming the anchor 106 remain together—the ball weld 114 prevents wires (e.g., any and/or all of up to nineteen thereof) from fraying. This may make installation and removal, examination, evaluation, and/or inspection of the stimulation lead 100 easier. Other processes may successfully accomplish the goals of a ball weld as well, such as cutting the anchor to length with a laser such that the filars are simultaneously melted together in a fashion similar to a ball weld or a ball-type well (e.g., a partial or full ball weld). Further, the deinsultated portion of the stimulation lead 100 or as also referred to herein as the uninsulated portion of the multi-wire filar 102 of the stimulation lead 100 may comprise an electrode 120 through which electrical energy may be applied as described in more detail below. In these embodiments, the deinsulated portion of the stimulation lead 100 may comprise the electrode 120 of the present system. An example of the electrode 120 is shown in FIGS. 2, 2B and 2C. In each of these figures, the electrode 120 may comprise a different pitch. These pitches are merely exemplary and the present disclosure is not limited to the specific pitch shown.

In some embodiments, the multiple filar wire 102 may include an inner layer 404 and an outer layer 406. The inner layer 404 may comprise a number of filars. For example, in a 1×19 multi-filar wire, the inner layer 404 may have 6 filars. The winding of the inner layer 404 has an orientation (e.g., a right hand lay, a left hand lay, etc.). In some examples, to provide both flexibility and wear resistance, the orientation of the inner layer 404 is the same (or opposite) as the orientation of the wrapping of the helical coil structure of the body 104. The outer layer 406 has a number of filars. For example, in a 1×19 multi-filar wire, the outer layer 406 has 12 filars. The winding of the outer layer 406 has an orientation that is the opposite the orientation of the winding of the inner layer 406. In this embodiment, the multiple filar wire 102 may not include the inner core 402 as described above.

Fracture resistance is an important characteristic for a temporarily (e.g., up to 60 days) implanted stimulation lead (e.g., like the stimulation lead 100 above). The stimulation lead 100 should (a) stay anchored in the treatment location as treatment is provided and/or the patient moves, (b) be resilient/flexible when treatment is provided and/or the patient moves, (c) withstand the stress caused by the movement of the tissue, anatomy, and/or patient, (d) have a sufficiently high enough withdraw force to remain correctly located and oriented (e.g., stay) in the patient for the intended duration and/or a temporary period of time (e.g., 15 days, 30 days, 60 days, etc.), and (e) have a sufficiently low enough withdrawal force to be removed while avoiding (or without) surgical intervention, while avoiding or preventing tissue damage (or unnecessary tissue damage) without causing undue discomfort to the patient, and without damaging or fracturing the stimulation lead. For example, if the stimulation lead is too stiff, it will not move easily with the patient, putting stress on keeping the stimulation lead anchored. On the other hand, if the stimulation lead is not stiff enough, the over flexing of the stimulation lead can promote stress fracturing. Simply substituting one component in the stimulation lead for another cannot be expected to provide all these benefits. For example, a thicker wire and/or anchor is expected to cause a greater stiffness.

Figure 5:
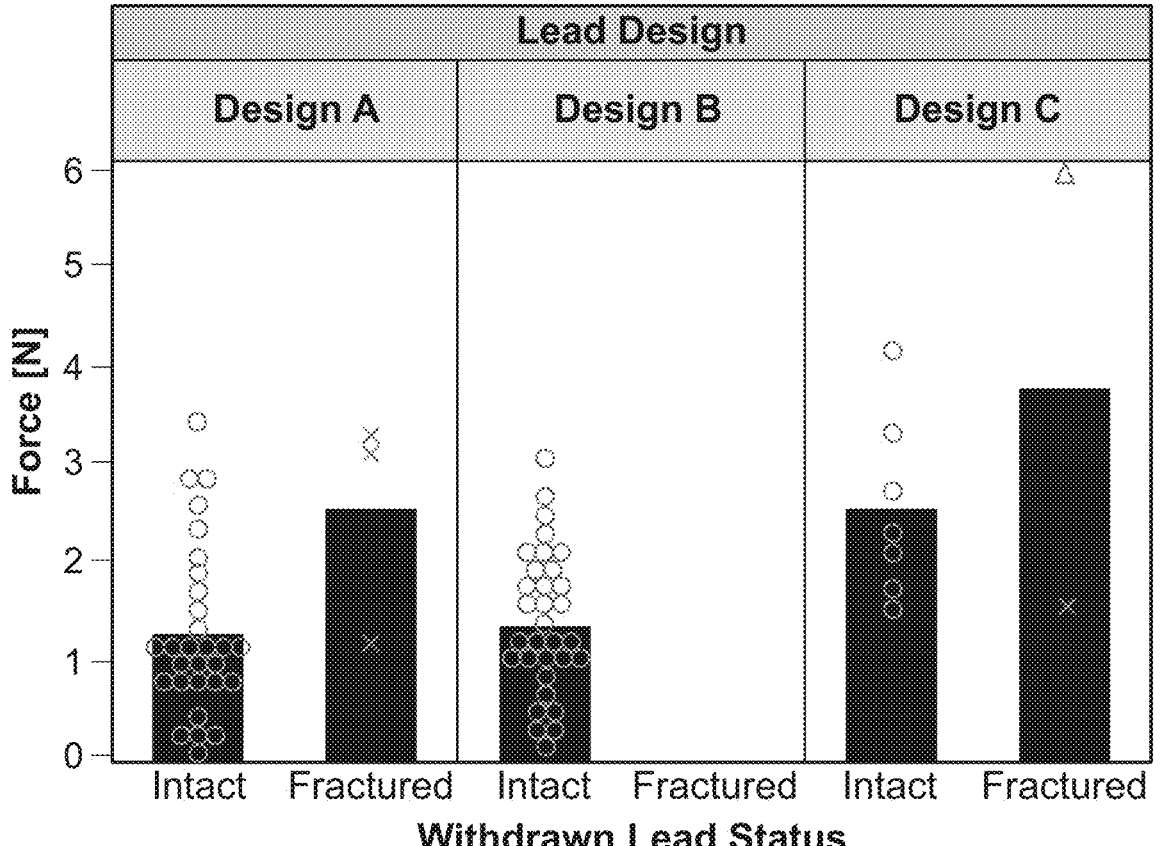
FIG. 5 depicts a comparative testing data that represents unexpected results obtained by the stimulation lead of FIG. 1, in accordance with the teachings of this disclosure
Figure 6:
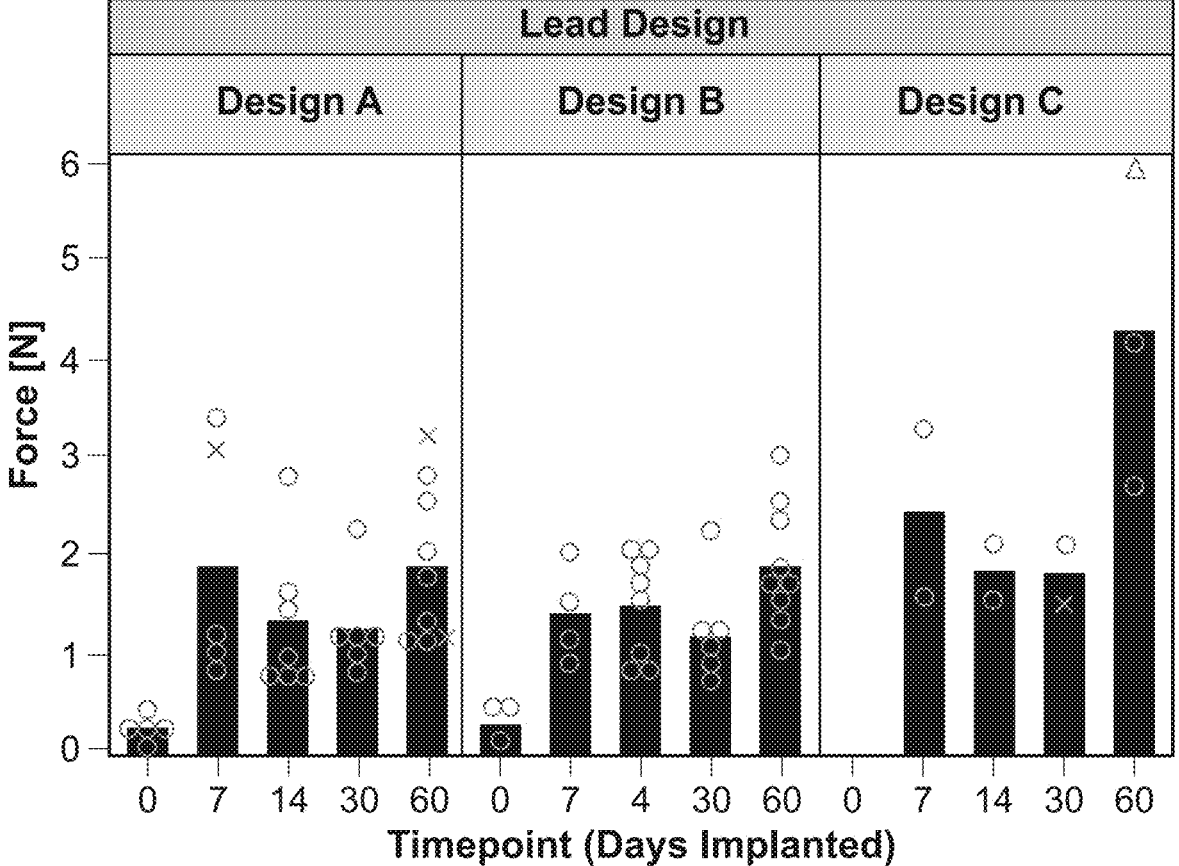
FIG. 6 depicts comparative testing data that represents unexpected results obtained by the stimulation lead of FIG. 1, in accordance with the teachings of this disclosure.
Figure 7:
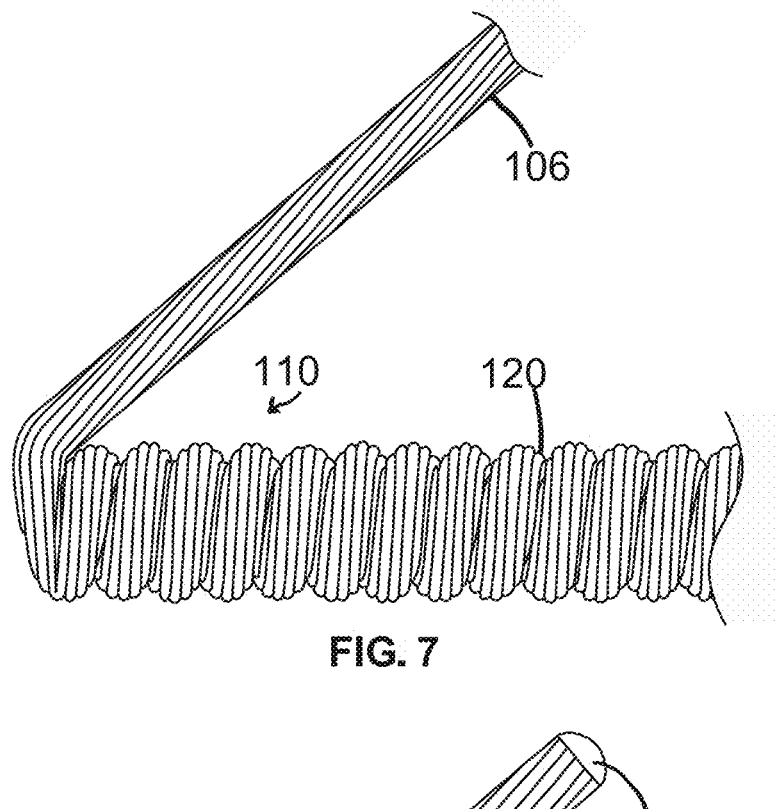
FIG. 7 illustrates a portion of a stimulation lead in accordance with the teachings of this disclosure.
Figure 8:
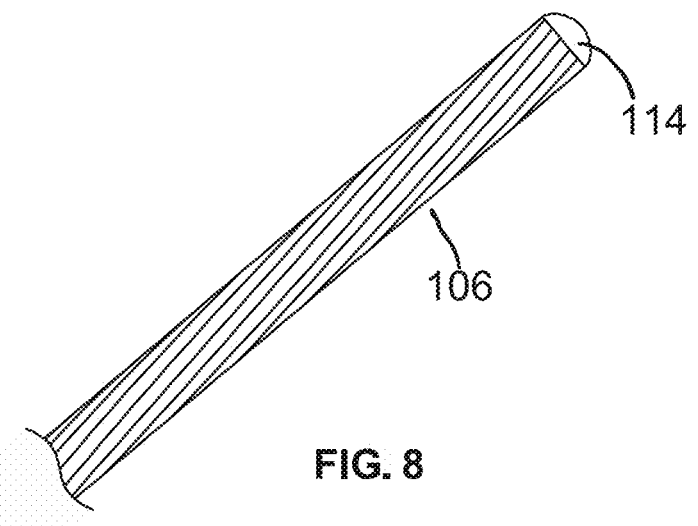
FIG. 8 illustrates an anchor portion of the stimulation lead of FIG. 7.
Figure 9:
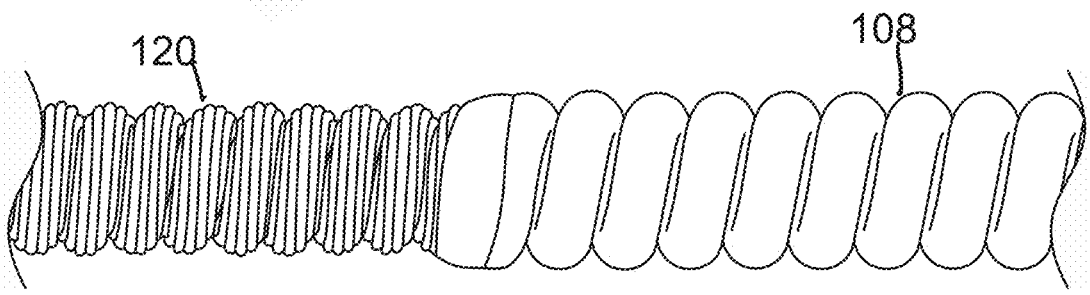
FIG. 9 illustrates a portion of a stimulation lead in accordance with the teachings of this disclosure depicting a transition from an insulated portion and a deinsulated portion.
Figure 10:
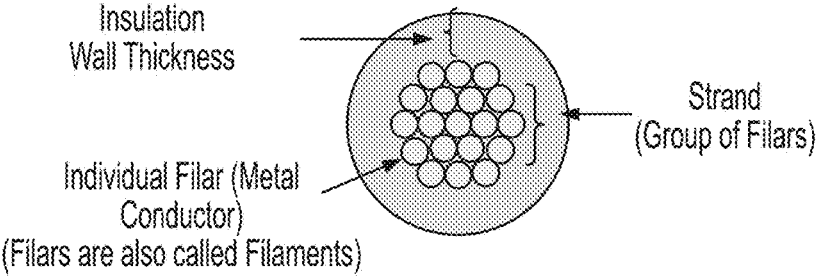
FIG. 10 illustrates a cross section of a multi-filar wire used to form a stimulation lead, in accordance with the teachings of this disclosure.
Figure 22B:
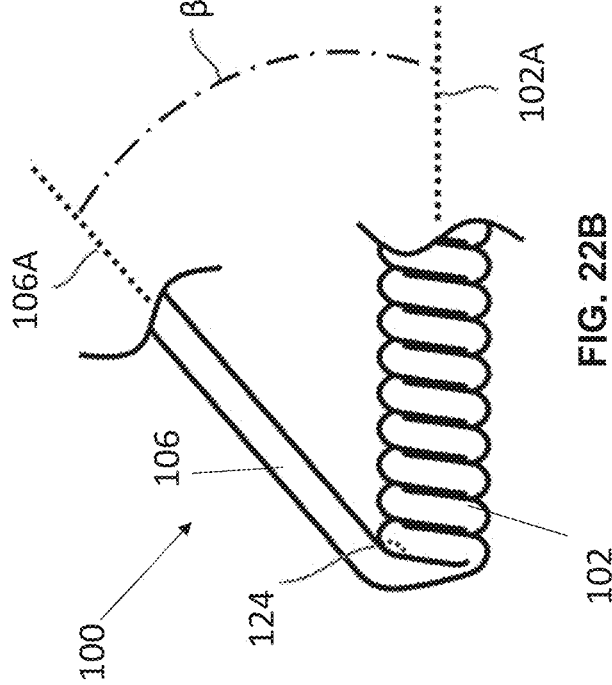
FIG. 22B is a side view of bending of a non-coiled portion of a stimulation lead of an embodiment of the present disclosure relative to a coiled portion thereof.
Figure 22A:
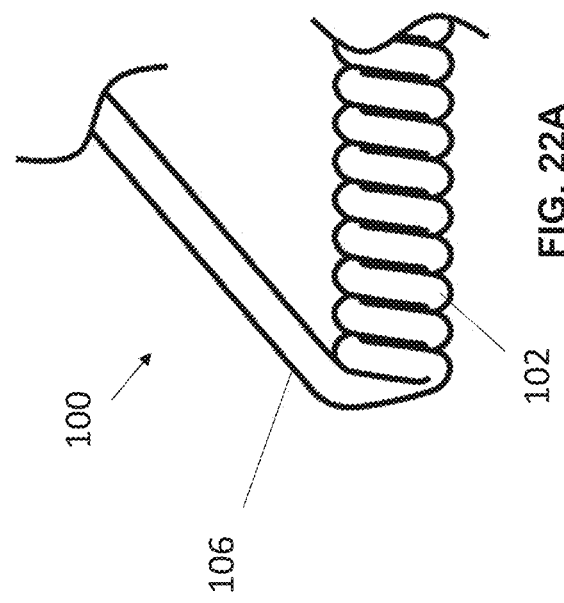
FIG. 22A is a side view of bending of a non-coiled portion of a stimulation lead of an embodiment of the present disclosure relative to a coiled portion thereof.
Figure 22D:
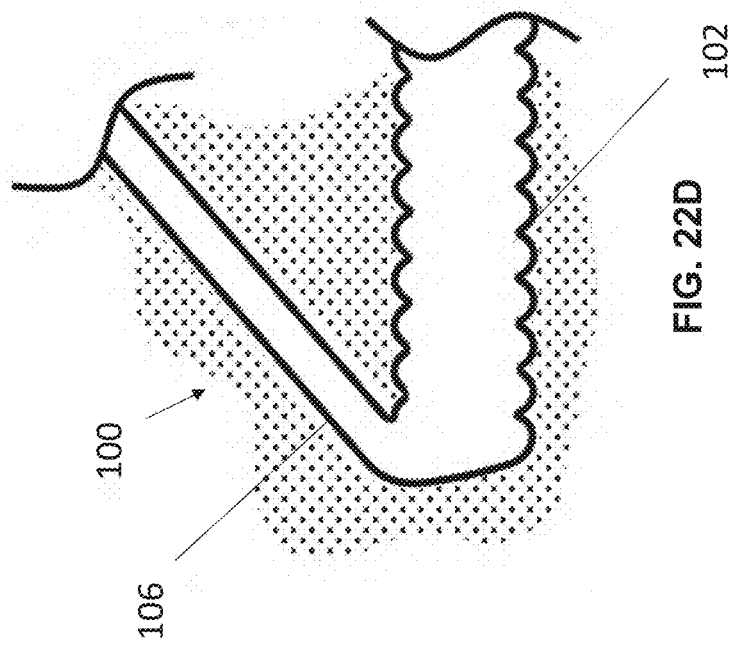
FIG. 22D is a side view of bending of a non-coiled portion of a stimulation lead of an embodiment of the present disclosure relative to a coiled portion thereof with tissue in-growth shown.
Figure 22C:
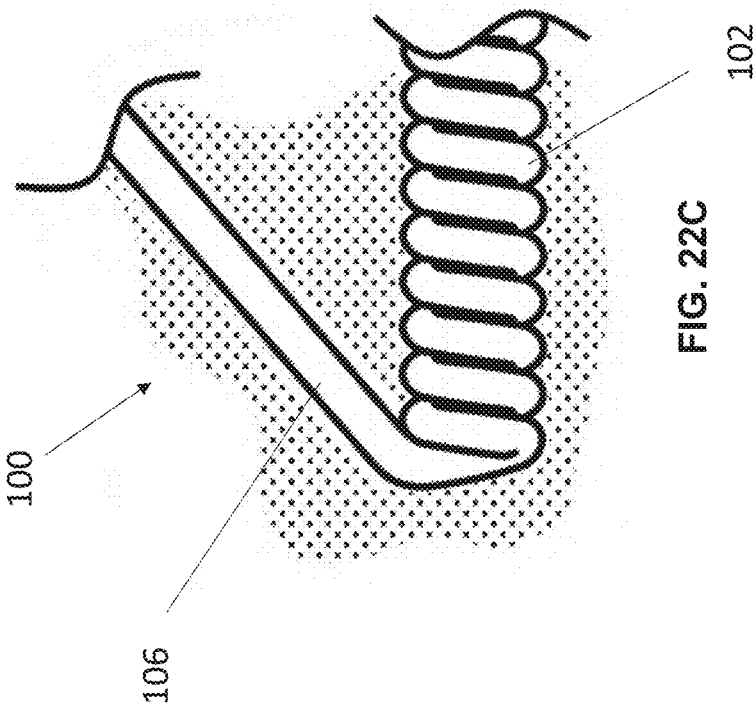
FIG. 22C is a side view of bending of a non-coiled portion of a stimulation lead of an embodiment of the present disclosure relative to a coiled portion thereof with tissue in-growth shown.

FIGS. 5 and 6 illustrate experimental results on stimulation leads with different characteristics. A first stimulation lead (sometimes referred to as "Design A") is a 1×7 multifilar wire stimulation lead made of 316L stainless steel with an anchor with a helical coil structure that is the same diameter as the helically coiled wire that makes up the helically coiled electrode portion, non-insulated portion, or deinsulated portion of the stimulation lead. The first stimulation lead is designed like a leading temporary stimulation lead on the market (e.g., an existing lead). A second stimulation lead (e.g., the stimulation lead 100 of FIG. 1 above) (sometimes referred to as "Design B") has a 1×19 multi-filar wire made of 316LVM stainless steel and is structured as described above. In the second stimulation lead, the angle between the body and the anchor is approximately 90 degrees or in some embodiments between 40 and 110 degrees. By way of a non-limiting example, the anchor 106 may be bent at 124 relative to the multi-filar wire portion 102 at an angle R. As shown in FIG. 22B, the portion 106A of the anchor 106 is at an angle R to the portion 102A of the multi-wire filar 102. The angle β can comprise any angle, including, without limitation between 20-110 degrees and/or as otherwise described herein. A third stimulation lead was designed with more improvements over the first and second stimulation leads that one would expect, through conventional experience, to confer greater benefits. The third stimulation lead (sometimes referred to as "Design C") has the same structure as the second stimulation lead except that the anchor has a helical coil structure, similar to the first stimulation lead. In the third stimulation lead, the angle between the body and the anchor is approximately 90 degrees or in some embodiments between 40 and 110 degrees.

Figure 23B:
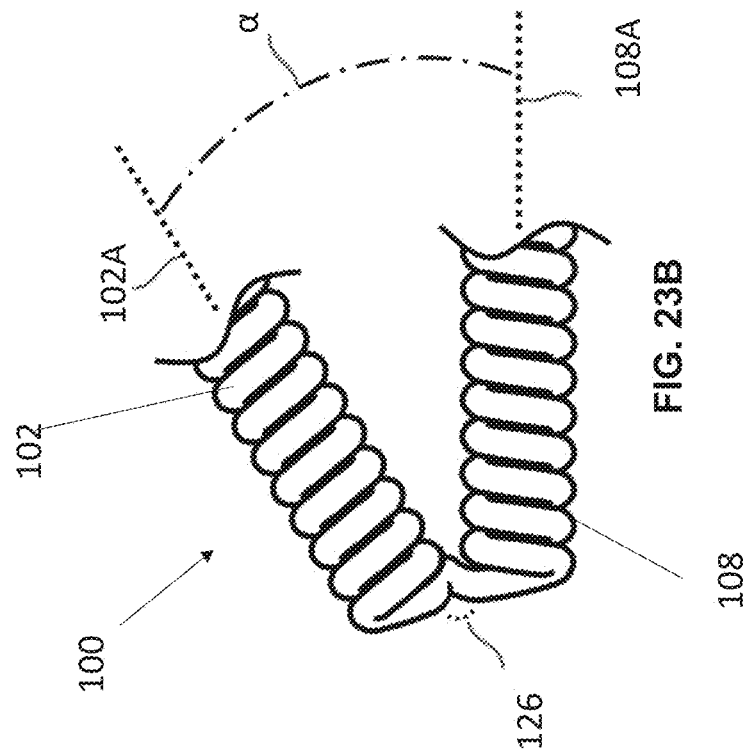
FIG. 23B is a side view of bending of a coiled portion of a stimulation lead of an embodiment of the present disclosure relative to another coiled portion thereof.
Figure 23A:
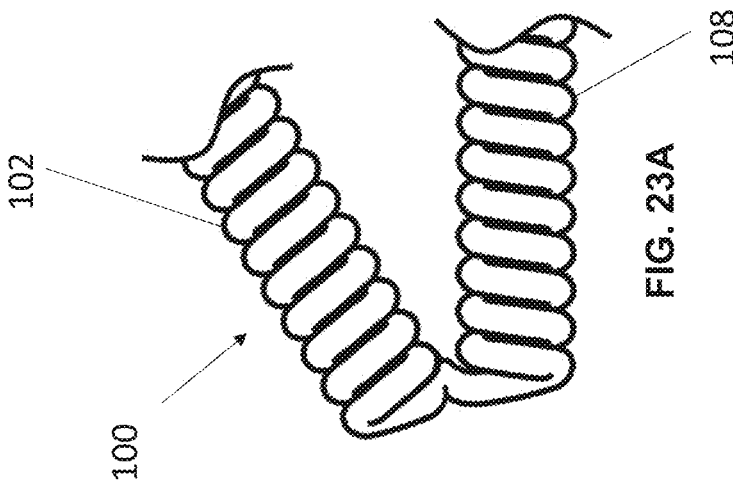
FIG. 23A is a side view of bending of a coiled portion of a stimulation lead of an embodiment of the present disclosure relative to another coiled portion thereof.
Figure 23D:
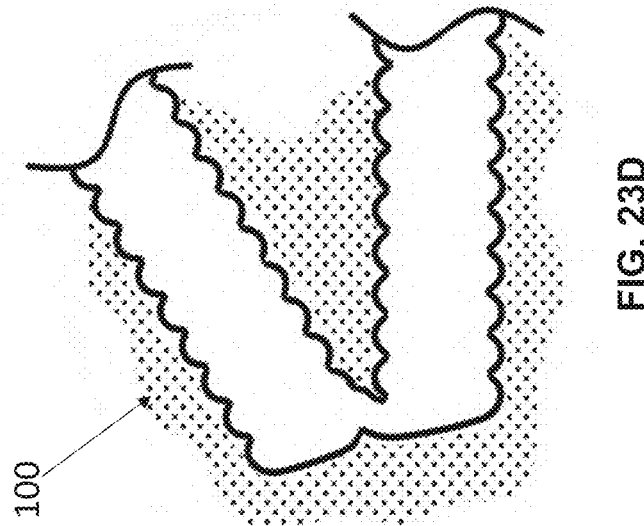
FIG. 23D is a side view of bending of a coiled portion of a stimulation lead of an embodiment of the present disclosure relative to another coiled portion thereof with tissue in-growth shown.
Figure 23C:
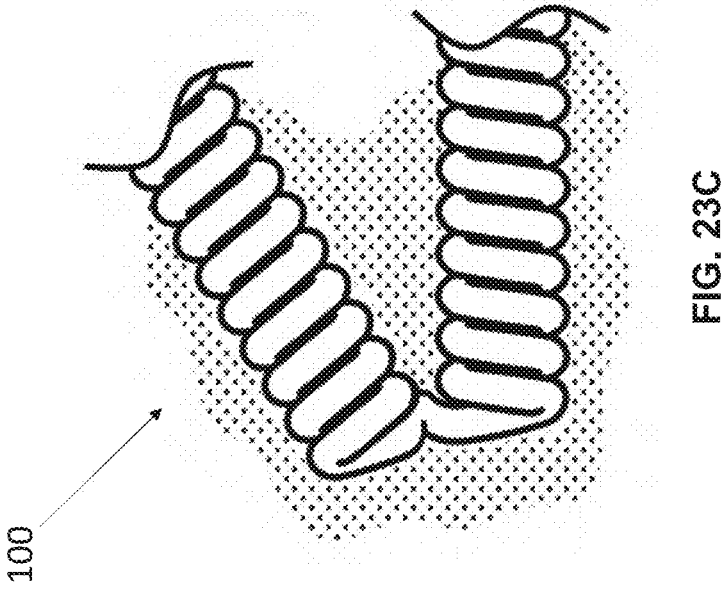
FIG. 23C is a side view of bending of a coiled portion of a stimulation lead of an embodiment of the present disclosure relative to another coiled portion thereof with tissue in-growth shown.

Further, as shown in FIG. 23B, the multi-wire filar 102 may bend relative to the insulated portion 108 of the stimulation lead 100. In particular, the mult-wire filar 102 may bend at bend 126 relative to the insulated portion 108 at an angle α. As shown in FIG. 23B, the portion 108A of the insulated portion is at an angle α to the portion 102A of the multi-wire filar 102. The angle α can comprise any angle, including, without limitation between 20-110 degrees and/or as otherwise described herein.

In experimentation, Design A had 3 fractures observed upon removal of the stimulation lead out of 27 implanted leads. One Design A stimulation lead that had been implanted for 7 days fractured and 2 Design A stimulation leads that had been implanted for 60 days fractured. Design B had no fractures upon removal. Design C stimulation lead had 2 fractures that appeared to occur during removal of the leads. One Design C stimulation lead that had been implanted for 30 days fractured and 1 Design C stimulation lead that had been implanted for 60 days fractured. Overall, Design B stimulation leads showed better fracture resistance than the other designs. The reason for such are as described above regarding stimulation lead 100.

However, unexpectedly, the average peak withdrawal force for Design A and Design B were substantially similar as to have the same or similar withdraw experience for the patient. However, Design C has a significantly higher average withdraw force. FIGS. 5 and 6 illustrate the withdraw forces. FIG. 5 illustrates the average withdraw forces (represented by the black bar) and individual withdraw forces (represented by various symbols) separated by leads that with withdrawn intact and leads that were fractured when withdrawn. FIG. 6 illustrates the average and individual withdraw forces separated by length that the stimulation lead was implanted. Design A and Design B has similar withdraw forces. This would translate to a similar withdraw experience for the patient. However, the withdraw forces for Design C were significantly higher and would lead to possible discomfort for the patient in some circumstances (e.g., the 60-day implant time).

These experimental results show, unexpectedly, that stimulation lead 100 (e.g., Design B) has a greater fracture resistance than the first stimulation lead while maintaining a similar withdraw force profile. Additionally, the experimental results show, unexpectedly, that designing a simulation lead with the features of the first stimulation lead but using a thicker wire (e.g., Design C) does not confer the same benefits as the first stimulation plus increased fracture resistance.

Methods, Results and Conclusions of the study of the open-coil percutaneous lead design are described further here:

Methods: The IACUC-approved study included nine Yucatan minipigs implanted with open-coil percutaneous PNS leads spaced at 5 cm intervals bilaterally along the dorsal paraspinal musculature. At Day 7 (n=2 minipigs), Day 14 (n=2), Day 30 (n=2), and Day 60 (n=3), a subset of leads from each minipig were withdrawn to measure the force required for removal and a different subset of leads were removed with the surrounding tissue en bloc and fixed by immersion in 10% formalin. Negative controls were implanted immediately before tissue harvest or lead withdrawal. Tissues were fixed, plastic embedded, sectioned, stained with hematoxylin and eosin (H&E), and evaluated via light microscopy. Gross and microscopic histological features including tissue fibrosis and ingrowth were evaluated qualitatively and quantitatively by an independent certified pathologist.

Results: Gross observation and quantitative scoring of histological sections identified extensive tissue ingrowth into the coiled structure of the implanted leads at all post-implant time points (Days 7, 14, 30, and 60). No ingrowth was detected in negative control samples. The force required for lead withdrawal increased at Day 7 compared to negative controls and remained relatively consistent at all remaining post-implant time points. Tissue ingrowth did not preclude withdrawal of the leads at any study time point, which is consistent with the present withdrawal force measurements remaining substantially below the tensile strength of the leads established in prior benchtop testing.

Conclusions: Histological and withdrawal force data demonstrated that open-coil PNS leads enabled significant tissue ingrowth into the lead structure as early as Day 7 following percutaneous implantation.

Although the embodiments of the present invention have been illustrated in the accompanying drawings and described in the foregoing detailed description, it is to be understood that the present disclosure is not to be limited to just the embodiments disclosed, but that the disclosure described herein is capable of numerous rearrangements, modifications and substitutions without departing from the scope of the claims hereafter. The terms "includes," "including," and "include" are inclusive and have the same scope as "comprises," "comprising," and "comprise" respectively.

One embodiment consists of increasing the strength of stimulation lead 100, for example by incorporating one or more filars of high tensile strength materials (such as but not limited to MP35N, nickel-chromium-molybdenum super alloy) into the stimulation lead 100. Adding such filar(s) and/or replacing current lead wire filar(s) with such filar(s) or wire(s) increases the fracture-resistant capabilities of the stimulation lead 100.

Another non-limiting embodiment consists of improving the strength of the stimulation lead 100 by adding a new filar(s) (or filament(s)) within the inner core 402, inner layer 404 and/or outer layer 406. In this non-limiting example, the new filar/filament would not completely fill the opening. There would remain a gap between the outside of the new filar/filament and the inside of the coiled wire that comprise the inner layer 404 and outer layer 406. Moreover, this new filar/filament would not extend the entire length of the stimulation lead 100. In this non-limiting example, these two provisions help the stimulation lead remain flexible with both axial and radial forces during normal use. When the stimulation lead is withdrawn, as the coiled wire straightens out, the inner diameter of the coils of the lead will reduce and the coiled wire becomes bound to the central filar/filament. Thus the stimulation lead has a higher tensile strength and reduced flexibility during the removal process. The new filar/filament in the core could be a metal (e.g., 316L or MP35N) or it might be a polymer (e.g., Aramid). Such an embodiment could advantageously be combined with other aspects of the disclosed herein (e.g., the use of stylet proximate to—or even as part of—the filar/filament).

The stimulation lead 100 of the present disclosure may also reduce the risk of accidental lead dislodgement. This is particularly useful during the initial period of time in which the stimulation lead is left in place within the desired tissue (e.g., in the time period prior to complete encapsulation of the lead within connective tissue). Other potential advantages (possibly in addition to others noted herein) include the ability to enable the duration of the lead placement and stimulation testing procedures to be minimized; a reduction in the number of percutaneous insertions required; a decrease risk to the patient by enabling efficient positioning and re-positioning of the stimulation lead for stimulation testing and correct/optimal lead deployment by clinicians with minimal or no additional training, as well as by decreasing the time required to form electrical connections for testing. Therapy may be delivered to patients by clinicians in settings/scenarios that were previously burdensome, not practical and/or not possible (e.g., to treat pre-operative, pen-operative, and/or post-operative pain).

In certain embodiments, accidental lead dislodgement is also avoided by relying on an anchoring mechanism made from a bioabsorbable material (e.g., Polyglycolic acid: Trimethylene carbonate, Polylactic acid, or other appropriate bioabsorbable material with sufficient mechanical properties to act as an anchoring mechanism) at least in portions of the lead/electrode. The use of such a bioabsorbable anchor(s) facilitates fixation of the lead in the tissue, avoiding accidental dislodgement. Use of such an anchor(s) can also be designed such that as the lead becomes encapsulated/secured by tissue growth, the anchor(s) become absorbed, thereby reducing the risk of fracturing the lead upon removal at the end of the active therapy. Over time, the biosorbable portions are then accommodated naturally by the body, leaving only the stimulation portions of the lead securely in place.

Monofilaments of material (e.g., similar to dissolving sutures) may supplement the distal anchor(s), along with any number of optional barbs, in order to help with short-term fixation. These filaments and/or barbs may have varying or consistent geometry, including various shapes and thicknesses that can be made using conventional molding. These tips may be attached by integrating mechanically with the stimulation lead 100 by a number of appropriate methods, examples of which include integration within the stimulation lead, by overmolding the stimulation lead, or by covering the existing insulation coating of the stimulation lead 100 with a secondary extruded layer of bioabsorbable material. Additionally, bioabsorbable tips may be attached to the stimulation lead through a hot melt approach (using an absorbable material as the adhesive). Such approaches allow the present system to enhance short-term fixation and avoid accidental dislodgement while using or placing a self-anchoring, migration and infection resistant stimulation lead. These biosorbable aspects may be used alone or, advantageously, in combination with one or more aspects of the present disclosure.

Figure 17:
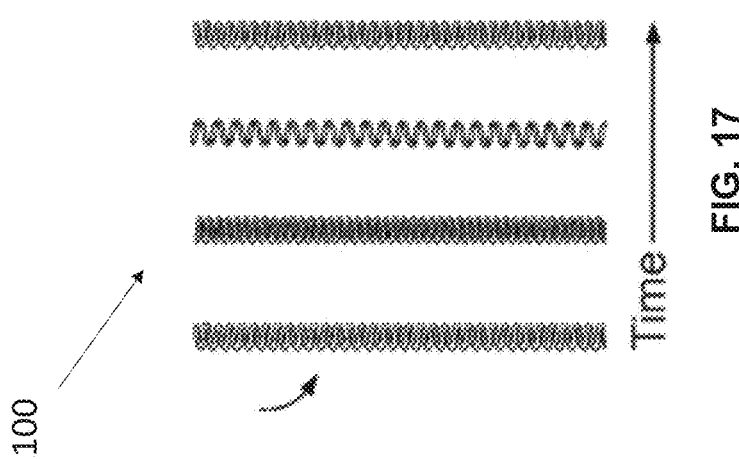
FIG. 17 are exemplary side views of a portion of stimulation leads as they might expand, contract, and flex within tissue.
Figure 16:
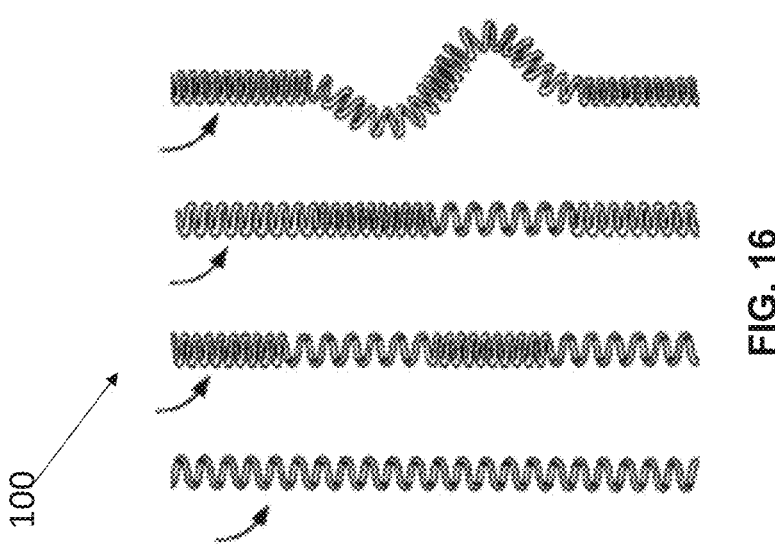
FIG. 16 are exemplary side views of a portion of stimulation leads according to certain disclosed aspects as they might expand, contract, and flex within tissue.
Figure 15:
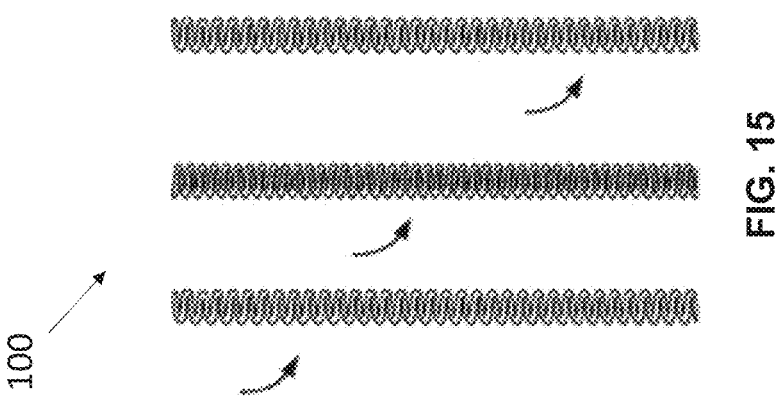
FIG. 15 are exemplary side views of a portion of stimulation leads according to certain disclosed aspects as they might expand, contract, and flex within tissue.

As shown in FIGS. 15-17, the stimulation lead 100 may be configured to bend, flex, stretch and/or distort forces applied thereto while inserted into a person. As shown, the stimulation lead 100 is configured to withstand such forces due to the helical coil structure of a portion of the stimulation lead 100. This allows the stimulation lead 100 to withstand forces that arise while being implanted in patient such that the stimulation lead 100 does not become withdrawn from the patient inadvertently.

Figure 20:
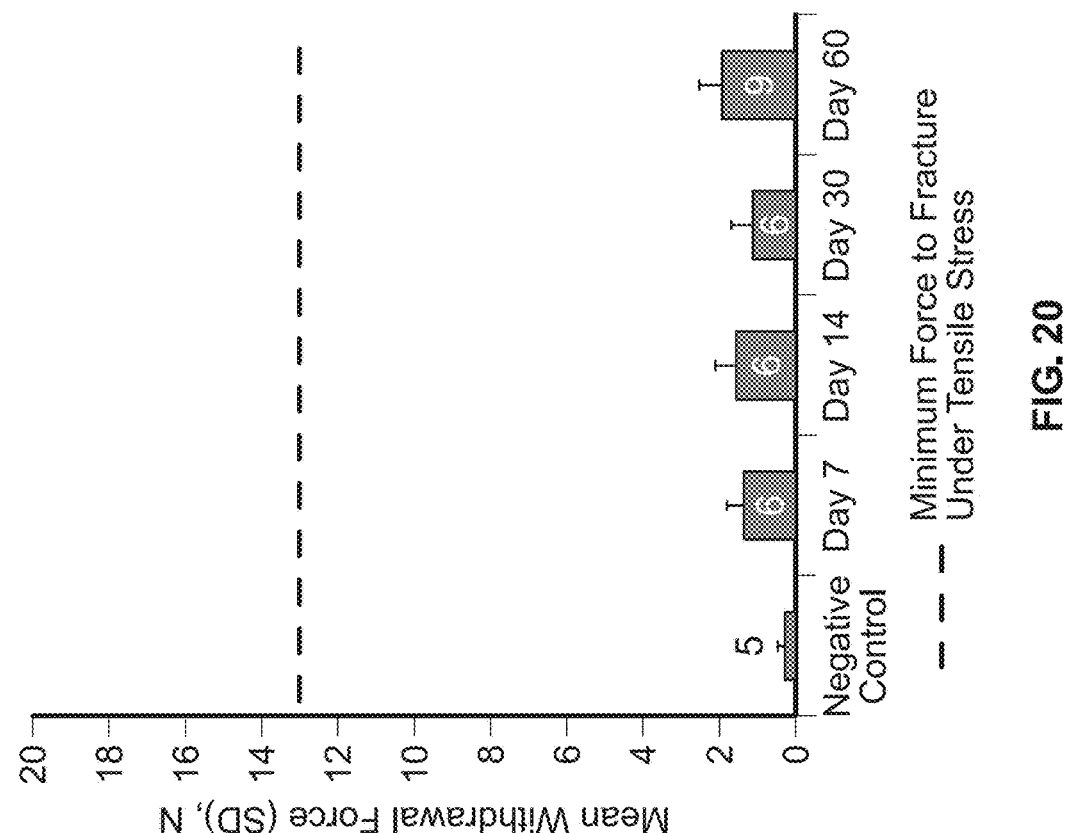
FIG. 20 is a graph showing the ultimate tensile strength of a stimulation lead of the present disclosure from an animal study.
Figure 19:
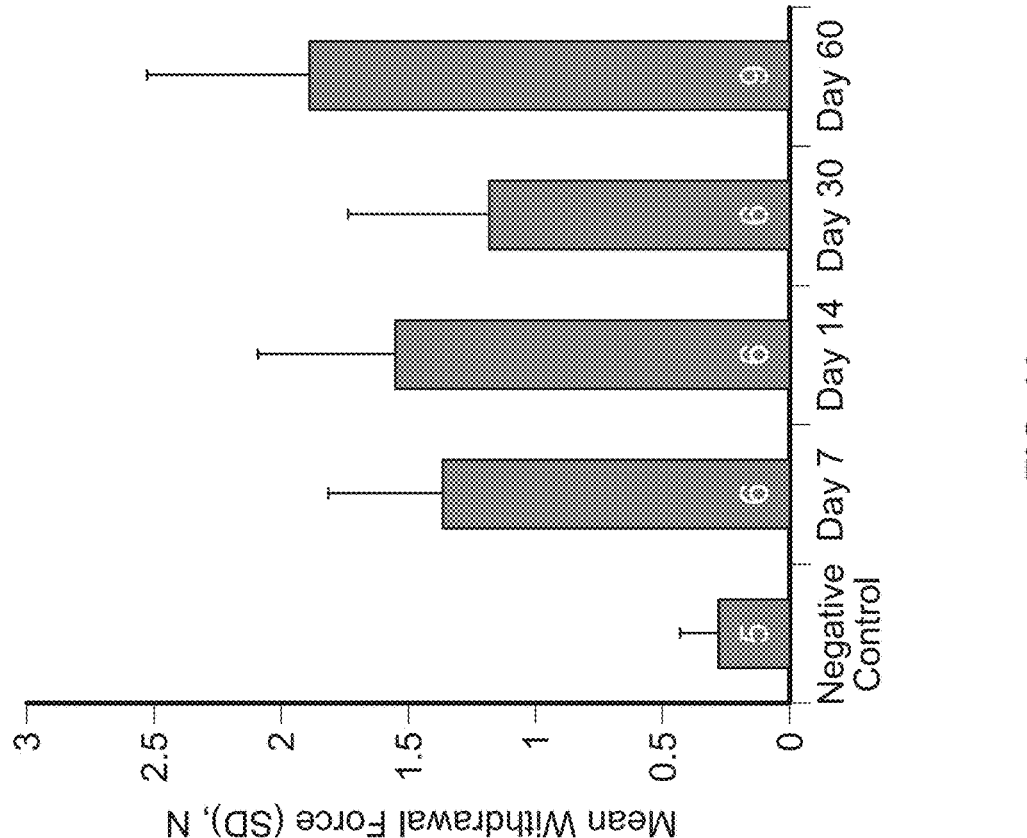
FIG. 19 is a graph showing beneficial tissue ingrowth of a stimulation lead of the present disclosure from an animal study.
Figures 21A, 21B:
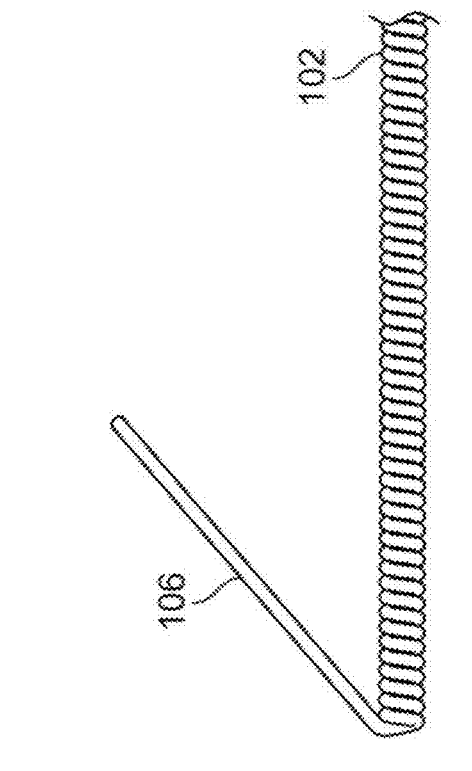
FIG. 21A is a side view of a bend of an anchor portion of an embodiment of a stimulation lead of the present disclosure.
FIG. 21B is a side view of a bend of an anchor portion of an embodiment of a stimulation lead of the present disclosure.
Figure 21D:
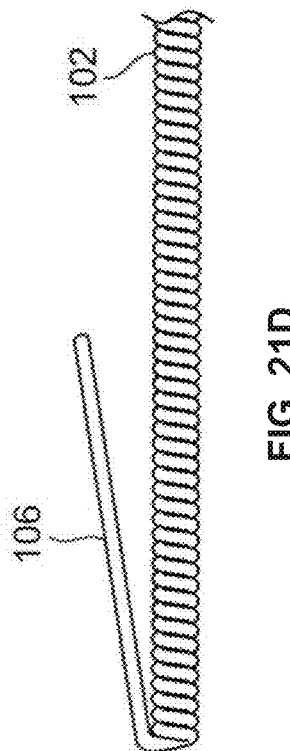
FIG. 21D is a side view of a bend of an anchor portion of an embodiment of a stimulation lead of the present disclosure.
Figure 21C:
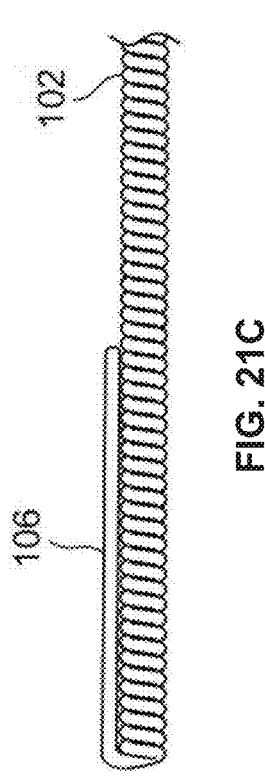
FIG. 21C is a side view of a bend of an anchor portion of an embodiment of a stimulation lead of the present disclosure.
Figures 21E, 21F:
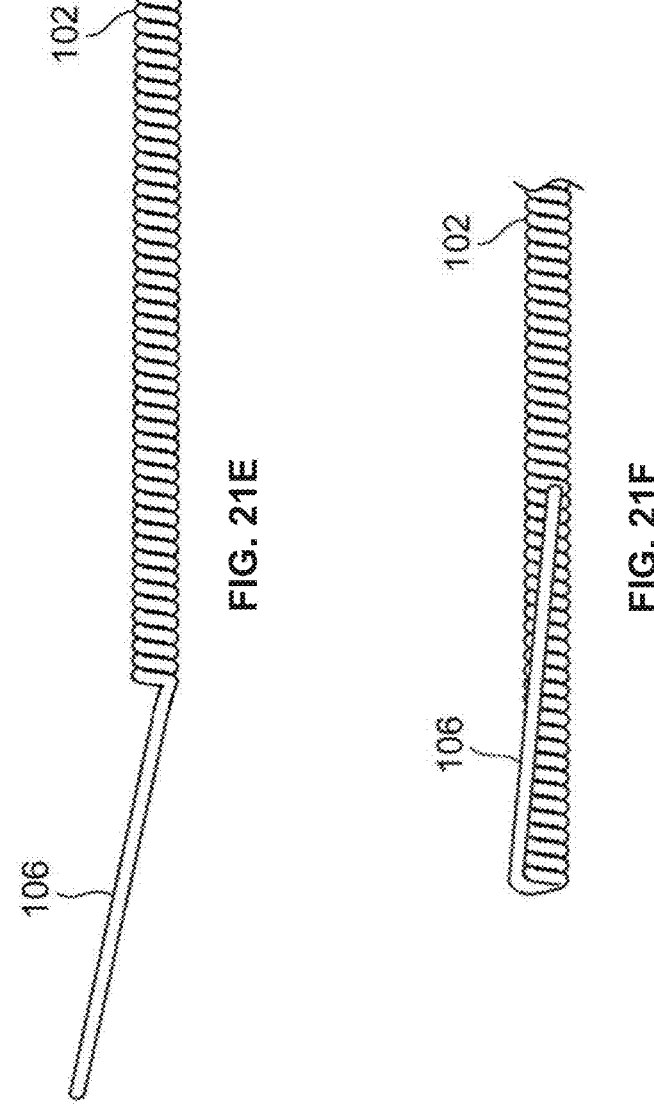
FIG. 21E is a side view of a bend of an anchor portion of an embodiment of a stimulation lead of the present disclosure.
FIG. 21F is a side view of a bend of an anchor portion of an embodiment of a stimulation lead of the present disclosure.
Figures 21G, 21H, 21I:
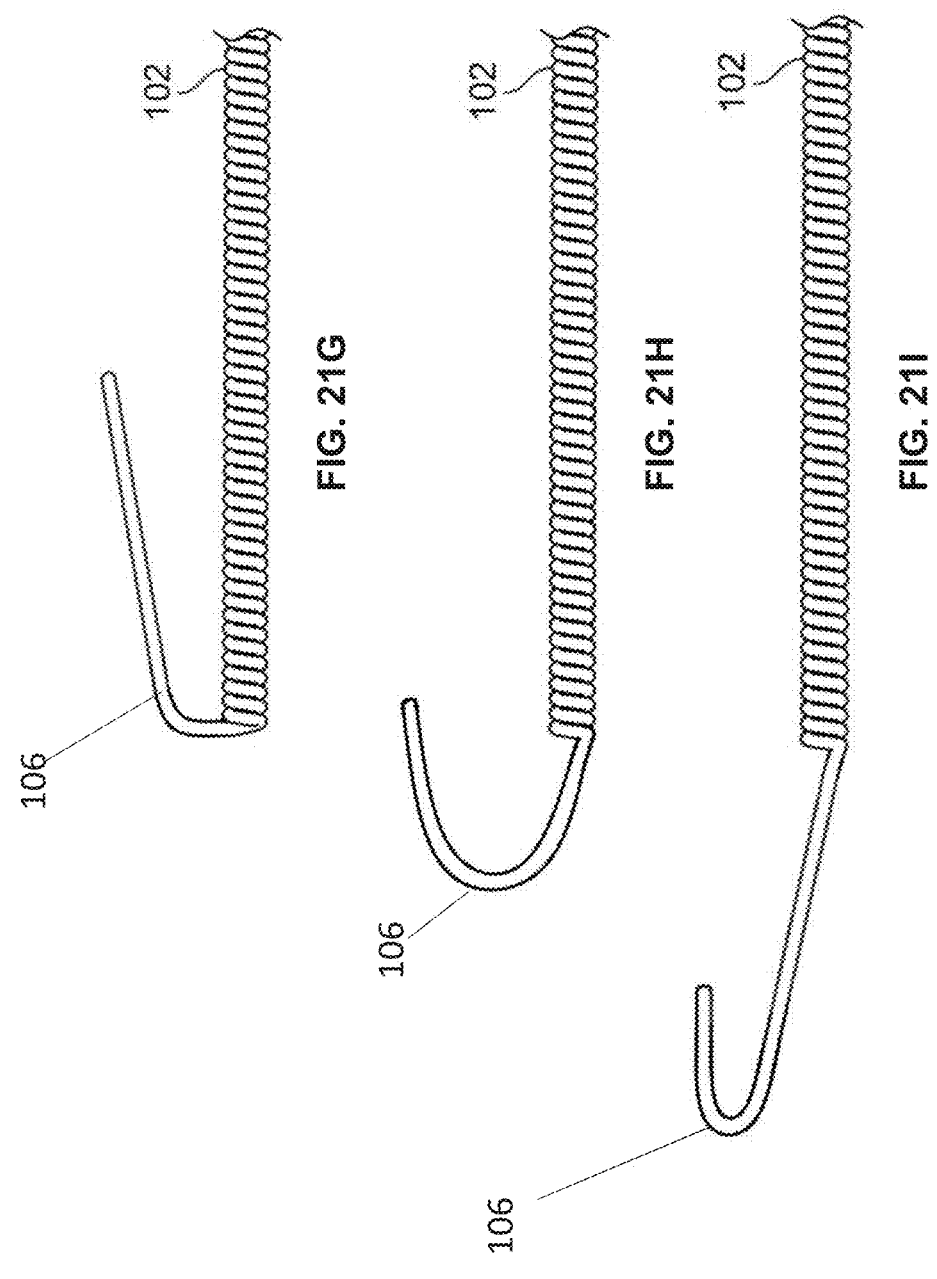
FIG. 21G is a side view of a bend of an anchor portion of an embodiment of a stimulation lead of the present disclosure.
FIG. 21H is a side view of a bend of an anchor portion of an embodiment of a stimulation lead of the present disclosure.
FIG. 21I is a side view of a bend of an anchor portion of an embodiment of a stimulation lead of the present disclosure.

FIGS. 19 and 20 further demonstration withdrawal force of the stimulation lead 100 resulting from an animal study data. FIG. 19 shows that beneficial tissue ingrowth occurs in the stimulation lead 100. FIG. 20 shows that the ultimate tensile strength (force required to fracture the stimulation lead 100 under tensile stress) is much higher than the force required to remove the stimulation lead 100 from the body despite the beneficial tissue ingrowth.

Figure 18:
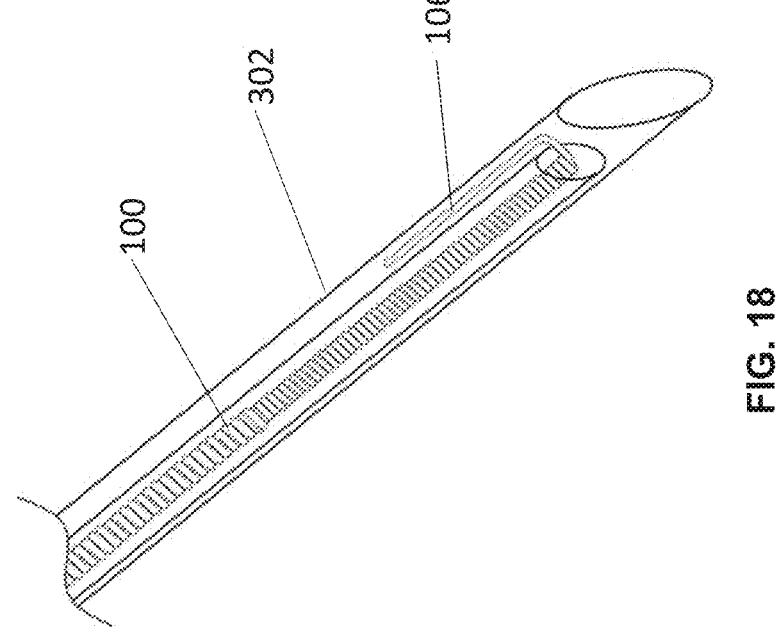
FIG. 18 is a perspective view of a portion of an introducer needle with a stimulation lead inserted therein.

As FIG. 18 shows, the stimulation lead 100 can be inserted via a needle introducer 302 or surgically implanted in proximity of a targeted nerve (e.g., a peripheral nerve) to deliver peripheral nerve stimulation (PNS) or stimulation of a named peripheral nerve or an unnamed peripheral nerve or stimulation of a part of the peripheral nervous system. Once proper placement is confirmed, the needle introducer 302 may be withdrawn, deploying the stimulation lead 100 and leaving it in place, allowing the lead (and/or electrode) placement to be minimally invasive, though surgical placement could also be utilized.

The stimulation lead 100 may comprise the configuration described above. For example, it may comprise one or more conductors or filars, e.g., one or more coiled metal components, disposed within an open or flexible elastomer core. The wire can be insulated, e.g., with a biocompatible polymer film, such as polyfluorocarbon, polyimide, or parylene. The lead may be desirably coated with a non-textured or textured, bacteriostatic material, which helps to stabilize the lead in a way that still permits easy removal at a later date and increases tolerance.

The lead may be electrically insulated everywhere except at one (monopolar), or two (bipolar), or three (tripolar) or more, for example, conduction locations near its distal tip (e.g., near the nerve or target). Each of the conduction locations may be connected to one or more conductors that run the length of the lead and lead extension, providing electrical continuity from the conduction location through the lead to an external pulse generator or stimulator or an implanted pulse generator or stimulator.

The conduction location or electrode or contact may comprise a de-insulated area of an otherwise insulated conductor that runs the length of an entirely insulated lead. The de-insulated conduction region of the conductor may be formed differently, e.g., it can be wound with a different or the same pitch, or wound with a larger or smaller diameter, or formed or molded to a different dimension. The conduction location or the electrode may comprise a separate material (e.g., metal or a conductive polymer) exposed to the body tissue to which the conductor of the wire is electrically coupled.

The lead is desirably provided with instructions (e.g., to instruct a physician, clinician, patient, and/or other user) and may be provided in a sterile package, and may be pre-loaded in the introducer needle or introducer device or system. The package can take various forms and the arrangement and contents of the package. The package can comprises a sterile, wrapped assembly. The package may includes an interior tray made, e.g., from die cut cardboard, plastic sheet, or thermo-formed plastic material, to hold the contents. The package may desirably include instructions for use for using the contents of the package to carry out the lead location and placement procedures, as is described in greater detail herein.

Figure 24B:
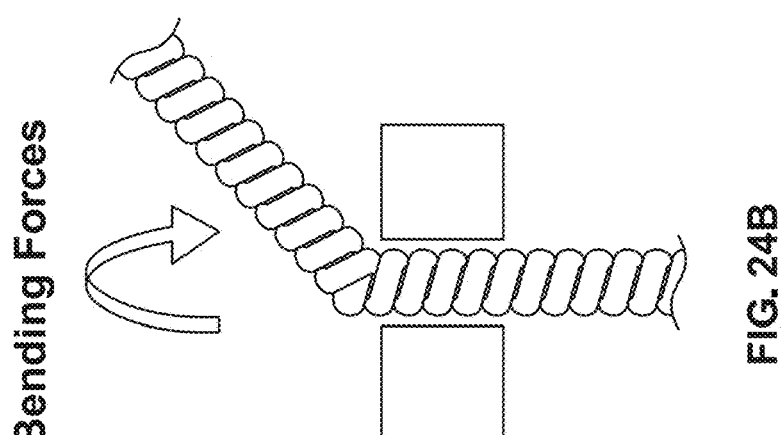
FIG. 24B is a graphical representation of a stimulation lead of an embodiment of the present disclosure under a bending force.
Figure 24A:
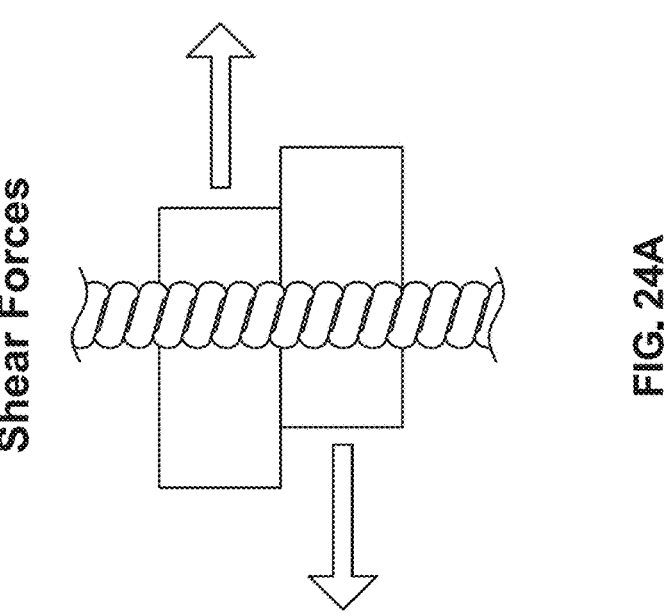
FIG. 24A is a graphical representation of a stimulation lead of an embodiment of the present disclosure under a shear force.
Figure 26C:
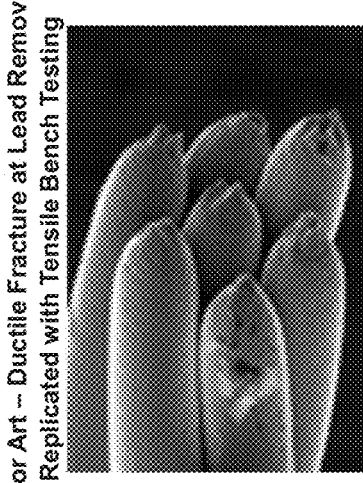
FIGS. 26A, 26B, 26C and 26D are microscope images of failures observed in the field and replicated on a bench test of prior art leads having a configuration different from that disclosed herein.
Figure 26D:
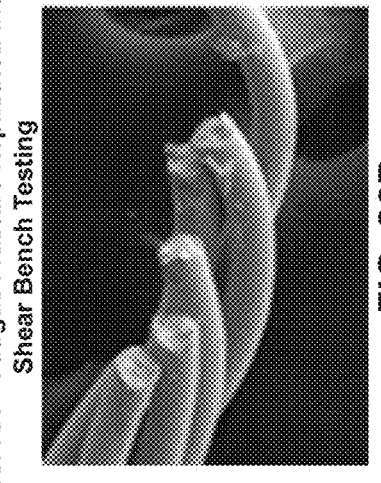
Figure 26A:
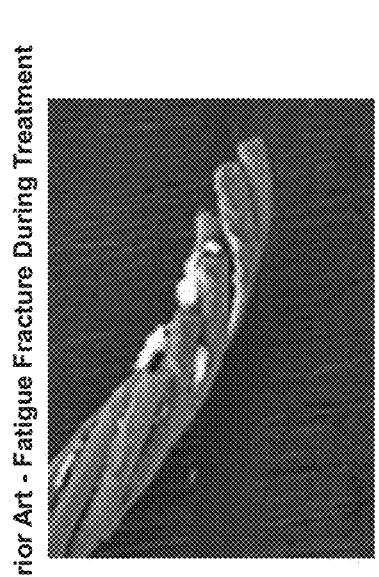
Figure 26B:

The stimulation lead 100 desirably possess mechanical properties in terms of flexibility and fatigue life that provide an operating life free of mechanical and/or electrical failure, taking into account the dynamics of the surrounding tissue (e.g., stretching, bending, pushing, pulling, crushing, etc.) as described above. An example of the bending force applied to the stimulation lead 100 is shown in FIG. 24B. This force can be tested on the device or devices shown in FIG. 25. The material of the lead desirably discourages excessive ingrowth of tissue (e.g., connective and/or fibrotic tissue) along its length, so as not to inhibit its withdrawal at the end of its use and/or when it is or will be removed (e.g., intentionally removed). However, the stimulation lead enables and encourages the growth or in-growth of sufficient tissue, to enhance its anchoring in tissue during use and reduce, minimize, and/or prevent pistoning of the lead in and out of the skin to prevent infection via ingress of contaminants.

One embodiment of the lead may comprise a minimally invasive coiled lead and electrode. The electrode may also include, at its distal tip, an anchoring element. The anchoring element is sized and configured so that it supports and enables correct deployment and when in contact with tissue, it takes purchase in tissue, to resist dislodgement, unwanted movement or migration of the electrode out of the correct location in the surrounding tissue. Desirably, the anchoring element is prevented from fully engaging body tissue until after the electrode has been correctly located and deployed.

The lead may exit through the skin and connect with one or more external stimulators, or the lead(s) may be routed subcutaneously to one or more implanted pulse generators, or they may be connected as needed to internal and external coils for RF (Radio Frequency) or inductively coupled wireless telemetry or communications or an inductively coupled power source or external pulse transmitter to control and/or power the implanted pulse generator. The implanted pulse generator may be located some distance (remote) from the lead.

The introducer may be insulated along the length of the shaft (e.g., along its length), except for those areas that correspond with the (to be exposed) conduction surfaces of the electrode housed inside the introducer. These surfaces on the outside of the introducer are electrically isolated from each other and from the shaft of the introducer. These surfaces may be electrically connected to a connector at the end of or connected to the introducer body. This allows connection to an external stimulator during the implantation process. Applying stimulating current through the outside surfaces of the introducer provides a close approximation to the response that the electrode will provide when it is deployed at the current location of the introducer.

The introducer may be sized and configured to be bent by hand prior to its insertion through the skin. This will allow the physician to place lead in a location that is not in an unobstructed straight line with the insertion site. The construction and materials of the introducer allow bending without interfering with the deployment of the lead and withdrawal of the introducer, leaving the lead in the tissue.

The lead may be placed or implanted in electrical proximity to a peripheral nerve. It may also be placed in electrical proximity to a target peripheral nerve but physically (and mechanically) spaced or located away or remote from the target peripheral nerve. This lead placement can make possible the stimulation of the targeted nerve with a single electrode or single contact to provide clinically significant pain relief and/or improvement of quality of life or resolution of other symptoms.

Instructions for use can direct use of system and method for the placement of a lead in tissue in electrical proximity and/or spaced away or remote from the nerve for improved recruitment of target nerves, e.g., with the placement of one or more leads. The instructions for use may include instructions for placing a lead for the activation of the targeted nerve in a system for the relief of pain, for example. The instructions for use may also include instructions for setting or recording stimulus parameters, including intensity associated with a first sensation of stimulation, a first noticeable muscle contraction or muscle tension, and/or a maximum tolerable contraction at multiple locations, which can be used to aid in determining desired stimulation parameters for optimal stimulation. The instructions can, of course vary. The instructions may be physically present in a kits holding the lead, but can also be supplied separately and/or electronically. The instructions can be embodied in separate instruction manuals. The instructions for use can also be available through an internet web page or other electronic means.

To determine the optimal placement for the lead, test stimulation may be delivered through needle electrodes (e.g., as part of and/or separate from the introducer or introducer system or device), and responses may be observed or recorded. Repositionable electrodes (e.g., on or separate from the introducer) may be used because they can be easily repositioned until the optimal location to deliver stimulation is determined.

At least one electrode may be placed in muscle tissue at a therapeutically effective distance spaced from a targeted nerve. By a "therapeutically effective distance" is meant that the electrode may not need to be placed against the targeted nerve, but rather spaced therefrom, electrically coupled to the nerve through other bodily tissue. The spacing is advantageous because it simplifies placement and stimulation procedures, reduces the risk of neurological injury to the patient (e.g., avoiding the need to be near or touching the nerve avoids the risk of nerve injury), shortens the procedure time, makes the method of pain relief more robust and durable and less likely to fail or lose effectiveness over time. Such placement also allows the electrode on the lead to be placed in tissue more resistant to electrode migration or unwanted movement and more tolerant of motion and short and/or long-term changes in electrode position relative to the targeted nerve. The lead may be inserted via the introducer in conventional fashion, which may be similar in size and shape to a hypodermic needle. The introducer may be any size. In a preferred embodiment, the introducer may range in size from 14, 15, 16, 17, or 18 gauge to 26 gauge. Prior to inserting the introducer, the insertion site may be cleaned with a disinfectant (e.g. Betadine, 2% Chlorhexidine/80% alcohol, 10% povidone-iodine, or similar agent). A local anesthetic (s) may be administered topically and/or subcutaneously to the area in which the electrode and/or introducer will be inserted.

The position of the lead or more specifically the electrodes may be checked by imaging techniques, such as ultrasound, fluoroscopy, or X-rays. Following placement of the lead(s), the portion of the leads which exit the skin may be secured to the skin using covering bandages and/or adhesives.

Electrical stimulation may be applied to the targeted peripheral nerve during and after placement of the lead to determine whether stimulation of the targeted nerve can generate comfortable sensations, paresthesias, muscles responses, or muscle tension or contraction that overlap partially or completely with the region of pain and/or reduce pain (or that are near the painful area). The pain may be perceived to be contained within a specific part(s) of the body and/or it may be perceived to be located outside of the body, as may be the case in persons with amputations who have phantom limb pain or pain in the amputated (or phantom) limb (s).

In a percutaneous system the lead may be percutaneously placed near the targeted nerve and exit at a skin puncture site. A trial or screening test may be conducted in a clinical setting (e.g. an office of a clinician, a laboratory, a procedure room, an operating room, etc.). During the trial, the lead is coupled to an external pulse generator and temporary percutaneous and/or surface return electrodes, to confirm the correct response (e.g., sensations, paresthesia coverage, muscle activation, and/or pain relief of the painful areas).

If the clinical screening test is successful, the patient may proceed to a home-trial or home-use with the lead coupled electrically to an external pulse generator with temporary percutaneous and/or surface return electrodes provided, to determine if pain relief can be sustained in the home environment. The trial, treatment, and/or therapy period may range from minutes to hours to days to weeks to months to years. The preferred trial period may be between 1 and 90 or 100 days, or up to 7, 14, 15, 21, 28, 20, 45, 60, 75, 90, or 100 days).

If either the screening test or home trial is unsuccessful, the lead may be quickly and easily removed intact.

However, if the screening test and/or home-trial are successful, the patient's percutaneous system may be converted into a fully implanted system if needed and/or desired by replacing the external pulse generator with an implantable pulse generator (the housing of which may serve as a return electrode)

Alternatively, it may be preferred to use a percutaneous system(s) as a therapy without proceeding to a fully implantable system. It is also to be appreciated that a home-trial is not a requirement for either the percutaneous system or a fully implanted system.

The duration of therapy or treatment for a percutaneous system may range from minutes to days to weeks to months to multiple years, and a preferred embodiment includes a duration ranging from 1 to 12 weeks. Another potential embodiment includes any duration or range of one or more days, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 days and/or more than 100 days, and the design of the present invention enables the parameters of the lead construction to be adjusted as needed to optimize the performance of the lead for the specific duration or potential range of duration of use of the lead in different scenarios.

Electrical stimulation may be applied between the lead and return electrode(s) (e.g., monopolar and/or uni-polar mode). Regulated current is the preferred type of stimulation, but other type(s) of stimulation (e.g. non-regulated current such as voltage-regulated) may also be used. Multiple combinations of types of electrodes may be used, such as surface, percutaneous, and/or implantable electrodes. The surface electrodes may be a standard shape or they may be tailored if needed to fit the contour of the skin.

In an embodiment of a percutaneous system, the surface electrode(s) may serve as the anode(s) (or return electrode(s)), but the surface electrode(s) may be used as the cathode (s) (active electrode (s)) if necessary. When serving as a return electrod(e), the location of the electrode(s) is not critical and may be positioned anywhere in the general vicinity, provided that the current path does not cross the heart.

The lead may be placed via multiple types of approaches. For example, if the targeted nerve includes nerves of the brachial plexus, the approach can include: (i) locate the site of skin puncture with appropriate landmarks, such as the clavicle, coracoid process, and axilla, as necessary; (ii) insert a sterile percutaneous stimulation lead preloaded in the introducer needle at a predetermined angle based on landmarks used; (iii) place a surface stimulation return electrode in proximity of the area in which the percutaneous lead has been placed. Test stimulation may be applied to the stimulation lead, with the surface electrode providing a return path. The surface electrode position may not be not critical to the therapy and it can be moved throughout the therapy to reduce the risk of skin irritation.

The stimulation lead may be coupled to the external pulse generator and to the return electrode. The desired stimulation parameters may be set. Test stimulation may be delivered using a current-regulated pulse generator, for example. The external pulse generator may be programmed to about 0.1 to about 10, 20, 30 or 40 milliamps (mA), a pulse duration or width of about five to about 200, 300, 400, or 500 microseconds (µs), a pulse frequency of about 1 to about 300 Hertz (Hz) o rup to 1,500 Hz or 10,000 Hz or 20,000 Hz or more, and a preferred on-off duty cycle of about 25 to about 100 percent (on vs. off), as a non-limiting example. Alternatively, rather than have an on-off duty cycle, the stimulation can be delivered constantly for a predetermined treatment time, such as about 1 to 8 or 9 weeks.

The introducer may be advanced slowly until the patient reports the first evoked sensation or a response is observed in the region experiencing pain. Progressively reducing the stimulus amplitude and advancing the introducer more slowly until the sensation can be evoked in the painful region at a predetermined stimulus amplitude. Stopping the advancement of the introducer, and increase the stimulus amplitude in small increments until the stimulation-evoked tingling sensation (paresthesia) or muscle or tissue response expands to overlay the entire region of pain.

Withdraw the introducer, leaving the percutaneous lead in proximity but away from the target nerve.

Cover the percutaneous exit site and lead with a bandage. A bandage may also be used to secure the external portion of the lead (or an extension cable used to couple the lead to the external pulse generator) to the skin. I Vary the stimulus amplitude in small steps (e.g., 0.1-0.5 mA, 0.5-1 mA, 1-2 mA, or larger steps) to determine the thresholds at which stimulation evokes first sensation (TsEN), sensation (paresthesia) superimposed on the region of pain (Tsup), muscle twitch (TMusl of the target muscle (innervated or not innervated by the target nerve), and/or maximum comfortable sensation (Tx). Query the patient at each stimulus intensity to determine sensation level, and visually monitor muscle response. Record the results.

If the desired response(s) cannot be evoked with the initial lead placement, redirect the introducer.

If sensations still cannot be evoked or are not desired to be evoked in a given patient, then the muscle twitch response of the muscle innervated or not innervated by the target nerve may be used to guide lead placement and then increase stimulus intensity until sufficient paresthesias are elicited in the painful region. Minimal muscle contraction may be acceptable if it is well tolerated by the patient in exchange for significant pain relief and if it does not lead to additional discomfort or fatigue.

If stimulation is successful, e.g., if the screening test and/or home-trial are successful, the patient's percutaneous system may or may not need to be converted into a fully implanted system by replacing the external pulse generator with an implantable pulse generator that is implanted in a convenient area (e.g., in a subcutaneous pocket over the hip or in the subclavicular area). In one embodiment, the stimulation lead used in the screening test and/or home use may be totally removed and discarded, and a new completely implantable stimulation lead may be tunneled subcutaneously and coupled to the implantable pulse generator.

Alternatively, when the targeted nerve includes one or more nerves of the lumbar plexus or sacral plexus, the approach may be either a posterior or an anterior approach For example, when the targeted nerve includes the sciatic nerve the introducer(s) and/or lead(s) may be directed towards the sciatic nerve using a posterior approach, such as a transgluteal approach or subgluteal approach. Alternatively, an adapted approach may also be used.

As an example, the introducer(s) and/or stimulation lead (s) may be inserted from a more lateral insertion site (or another site that is more desirable) than is typically used for regional anesthesiology because it has been found that a more lateral (or other) insertion site minimizes patient discomfort. The insertion site and/or path may be adapted or an alternative insertion site and/or path may be selected with an understanding of the type of tissue, muscle and other tissue planes, compartments, innervation of the tissue, muscle orientation, muscle fiber directionality, vascular and/or lymphatic vessels and structures, and other considerations below, surrounding, or near the insertion site or path. As non-limiting examples, it may be desirable to minimize the number of muscle planes that are transversed or crossed with the introducer(s) and/or stimulation lead(s), or it may be desirable to use an insertion site and/or insertion path that is not densely innervated by non-target sensory nerve fibers, maximizing the comfort of the placement procedure and the therapy following removal of the introducer, or it may be desirable to orient the direction of the introducer(s) and/or lead(s) relative to the directionality of the muscle fibers, placing the lead(s) in line with (e.g. parallel to) or orthogonal to the muscle fibers or any variation between parallel or orthogonal to the muscle fibers.

This approach allows stimulation lead placement near a targeted nerve with a quick (e.g. less than 10-15 minutes) outpatient procedure that may be performed in a standard community-based clinic. This makes possible widespread use and provides a minimally-invasive treatment, therapy, or test to determine if patients may benefit from the device and/or have the potential for long term relief and/or improvement.

The landmarks for the transgluteal approach may include the greater trochanter and the posterior superior iliac spine. The introducer may be inserted distal or proximal (e.g. approximately up to about 12-15 cm in a preferred embodiment) and/or medial or lateral (e.g. approximately up to about 12-15 cm in a preferred embodiment) to the midpoint between the greater trochanter and the posterior iliac spine. Alternatively, the introducer may be inserted at the midpoint between the greater trochanter and the posterior iliac spine. As a non-limiting example of patient positioning, the patient may be in a lateral decubitus position and tilted slightly forward in a preferred embodiment.

The landmarks for the subgluteal approach may include the greater trochanter and the ischial tuberosity. The introducer may be inserted distal or proximal (e.g. approximately up to about 10-15 cm in a preferred embodiment) and/or medialorlateral (e.g. approximately up to about 10-15 cm in a preferred embodiment) to the midpoint between the greater trochanter and the ischial tuberosity. Alternatively, the introducer may be inserted at the midpoint between the greater trochanter and the ischial tuberosity.

For any approach targeting the sciatic nerve (e.g. the transgluteal, subgluteal, and/or another or adapted approach), it may be beneficial to insert the introducer lateral to the midpoint between the relevant landmarks. A more lateral insertion point may maximize safety to the patient and/or the system, and it may increase patient comfort and minimize risk of damage to the lead or migration of the lead. As a non-limiting example of lateral placement, the introducer may be inserted lateral to the midpoint between the greater trochanter and the ischial tuberosity. The introducer may be inserted anywhere between the midpoint and the greater trochanter. The introducer may be inserted proximal or distal to the line between the greater trochanter and ischial tuberosity. It may be beneficial to insert the introducer distal to this line.

For example, when the targeted nerve includes the femoral nerve, the simulation lead may be directed towards the femoral nerve using an anterior approach. The landmarks may include the inguinal ligament, inguinal crease, and femoral artery. The patient may be in the supine position with ipsilateral extremity slightly (approximately 10 to 20 degrees) abducted. The introducer may be inserted near or below the femoral or inguinal crease and approximately 1 cm or more lateral to the pulse of the femoral artery.

The size and shape of tissues, such as the buttocks, surrounding the target nerves may vary across patients, and the approach may be modified as needed to accommodate various body sizes and shapes to access the target nerve.

Introducer placement may be often guided by muscle response to electrical stimulation.

As mentioned above, if the stimulation lead (or more specifically the electrode portion thereof) is too far away from the targeted nerve, then stimulation may be unable to evoke the desired response (e.g. muscle contraction(s), comfortable sensation(s) (or paresthesia(s)), and/or pain relief) in the desired region(s) at the desired stimulus intensity(ies). If the stimulation lead (or more specifically the electrode portion thereof) is too close to the targeted nerve, then stimulation may be unable to evoke the desired response(s) (e.g. muscle contraction(s), comfortable sensation (s) (or paresthesia (s)), and/or pain relief) in the desired region(s) at the desired stimulus intensity (ies) without evoking undesirable response (s) (e.g. unwanted and/or painful muscle contraction(s), sensation(s) (or paresthesia(s)), increase in pain, and/or generation of additional pain in related or unrelated area (s)). In some cases, it may difficult to locate the optimal lead placement (or distance from the targeted nerve and/or it may be desirable to increase the range stimulus intensities that evoke the desired response (s) without evoking the undesired response(s) so alternative stimulus waveforms and/or combinations of leads and/or electrode contacts may be used. A non-limiting example of alternative stimulus waveforms may include the use of a pre-pulse to increase the excitability of the target fiber(s) and/or decrease the excitability of the non-target fiber(s).

The stimulation lead described may be used percutaneously, e.g. introduced and operatively extending through the epidermis of an animal, thus providing an insulated, electrically conductive path through such epidermis. To accomplish such introduction, a lead introducer may be used.

At the distal end, the needle may be shaped or ground to a three-face lancet formation, including a point, a bevel portion, and a non-coring heel portion.

The stimulation lead may be insulated with a perfluoroalkoxy alkane (PFA) or a fluoropolymer and preloaded in an introducer.

PNS offers the potential to deliver therapeutic stimulation to the nerve innervating the region of pain and limit the distribution of sensation, paresthesia, and or muscle response to the area in which it is needed.

The present system provides the ability to generate significant paresthesia coverage and pain relief with a single lead, and indeed a single electrode even, inserted percutaneously and disposed remotely from a target nerve while also being removed fully or wholly intact and the end of the stimulation period or treatment period.

With the present system, the lead may be placed in tissue (e.g. muscle, adipose, connective, or other connective tissue) near a targeted peripheral nerve innervating a region of pain to deliver stimulation to relieve the pain and provide short term (e.g., temporary) and/or long term (e.g., sustained, lasting and/or permanent) pain relief.

Imaging (e.g., ultrasound or an alternate imaging technique, e.g. fluoroscopy) may be used to improve lead placement near nerves. Imaging such as ultrasound and/or fluoroscopy may improve lead placement in the form of increasing the total speed of the procedure (shortening the procedure's duration) and minimizing risk and/or avoiding injury or damage to the patient during placement of the lead (by avoiding blood vessels, organs, bones, ligaments, tendons, lymphatic vessels, &/or other structures) that may be damaged. One reason that imaging may be useful is that some nerves are (but do not have to be) located relatively deeply. Imaging may help but it may not be required.

There may be multiple components of one or more electrical stimulation systems that may utilize the present system. An electrical stimulation system according to the present disclosure includes a mounting patch assembly, an electrical stimulator, one or more electrical cables or connectors or means of connecting, and one or more stimulating electrodes that may be part of or carried on a percutaneous electrical lead. Embodiments according to the present disclosure may also include electrical connectors and connector mounting structure.

As used herein, the term "percutaneous" is to be understood to describe an electrical stimulation that is provided to animal and/or human tissue, where the source of the stimulation (e.g. device/tissue interface) is an electrode that is positioned subepidermally (e.g., in tissue at some depth below the skin). Percutaneous stimulation may be provided a number of ways, such as by an electrical conductor (e.g., wire) configured to be utilized while protruding through the epidermis of the animal. Alternatively, percutaneous stimulation may be provided by an implanted electrode that is wirelessly controlled and/or powered by a control unit positioned outside of the animal or human body.

While a percutaneous system is herein described, it is to be understood that applicable treatments may be provided initially by such percutaneous system and, if desirable, treatments may be continued through the use of an implantable electrical stimulator, where such stimulator and stimulation is contained entirely under the skin or epidermis of the animal.

The stimulation lead described may be used percutaneously, e.g. introduced through the skin or epidermis of an animal. To accomplish such introduction, a lead introducer may be used. The introducer may extends from a proximal end to a distal end, with a lumen extending therethrough. A plurality of depth markings are preferably provided along the length of the needle and/or introducer. The markings may be formed, e.g., by laser etching.

The percutaneous lead may be inserted, loaded, placed, or preloaded into the introducer for use. It may be desirable to provide a protective plastic tubular member disposed over the introducer needle for packaging and safety purposes. Lead and/or needle advancement is preferably to be stopped approximately 0-3 cm, 0.5-1 cm, and or 0.1-2.0 cm before or proximal to the target nerve.

The stimulator may be programmed to deliver a test stimulation to or via the introducer, probe and/or needle electrode. With the stimulus amplitude and frequency set to desired levels and the pulse duration set to a desired minimum or floor value, stimulation may be initiated by pressing and releasing the Start/Stop button. While stimulation is being delivered, the intensity of stimulation may be slowly increased by slowly until a desired response to the stimulation is obtained. A desired response may include a desired sensation, pain relief, paresthetic effect and/or comfortable muscle contraction in the target area. If a desired response to the stimulation is not obtained, the introducer, probe and/or needle electrode may be repositioned as necessary, to a location that provides the desired response at a comfortable stimulus intensity. The location of the needle may be identified and/or logged.

If desired, a local anesthetic may be administered subcutaneously, topically, or both at the insertion site for the electrode lead. It is preferable to refrain from administering a local anesthetic too close to the target electrode site because doing so could affect the response to stimulation. With the electrode lead situated within its introducer both may be introduced through the patient's skin towards the target stimulation site. Once a desired response is obtained, the introducer may be removed from the patient. It may or may not be helpful to apply gentle manual pressure towards the location of the electrode during withdrawal of the introducer and/or deployment of the lead.

Control of the stimulator and stimulation parameters may be provided by one or more external controllers. In the case of an external stimulator, the controller may be integrated with the external stimulator. The implanted pulse generator external controller (e.g., clinical programmer) may be a remote unit that uses RF (Radio Frequency) wireless telemetry communications (rather than an inductively coupled telemetry) to control the implanted pulse generator. The external or implantable pulse generator may use passive charge recovery to generate the stimulation waveform, regulated voltage (e.g., 10 mV to 20 V), and/or regulated current (e.g., about 10 pA to about 50 mA). Passive charge recovery is one method of generating a biphasic, charge-balanced pulse as desired for tissue stimulation without severe side effects due to a DC component of the current.

The neurostimulation pulse may by monophasic, biphasic, and/or multi-phasic. In the case of the biphasic or multi-phasic pulse, the pulse may be symmetrical or asymmetrical. Its shape may be rectangular or exponential or a combination of rectangular and exponential waveforms. The pulse width of each phase may range between e.g., about 0.1 μsec. to about 1.0 sec., as non-limiting examples.

Pulses may be applied in continuous or intermittent trains (i.e., the stimulus frequency changes as a function of time). In the case of intermittent pulses, the on/off duty cycle of pulses may be symmetrical or asymmetrical, and the duty cycle may be regular and repeatable from one intermittent burst to the next or the duty cycle of each set of bursts may vary in a random (or pseudo random) fashion. Varying the stimulus frequency and/or duty cycle may assist in warding off habituation because of the stimulus modulation.

The stimulating frequency may range from e.g., below or about 1 Hz to about 300 Hz or higher up to 1,000 Hz, 1,400 Hz, 1,500 Hz, 5,000 Hz, 10,000 Hz, 20,000 Hz, and/or 100,000 Hz or higher, and the frequency of stimulation may be constant or varying. In the case of applying stimulation with varying frequencies, the frequencies may vary in a consistent and repeatable pattern or in a random (or pseudo random) fashion or a combination of repeatable and random patterns.

The various devices and components just described can be consolidated for use in one or more functional kit(s). The kits can take various forms and the arrangement and contents of the kits can vary. Each kit can comprise a sterile, wrapped and/or sealed assembly. Each kit includes an interior tray made, e.g., from die cut cardboard, plastic sheet, or thermo-formed plastic material, which hold the contents. Kits also desirably include instructions for use for using the contents of the kit to carry out the procedures described above, including the systems and methods incorporating the percutaneous system and/or the implanted system.

The stimulation lead is desirably provided in a sterile package and may be pre-loaded in the introducer needle. The package can take various forms and arrangement of contents of the package.

The position of the electrodes may be checked by imaging techniques, such as ultrasound, fluoroscopy, or X-rays. Following placement of the lead(s), the portion of the leads which exit the skin may be secured to the skin using covering bandages and/or adhesives.

While stimulation is being applied, the stimulation lead (non-limiting examples of the lead could include a single or multi-contact electrode that is designed for temporary (percutaneous) or long-term (implant) use or a needle electrode (used for in-office testing only)) may be advanced (e.g., slowly advanced) towards the targeted peripheral nerve until the desired indicator response (e.g., patient sensation, and/or pain relief) is obtained. The intensity may then be decreased (e.g., gradually decreased) as the lead is advanced (e.g., advanced slowly) closer to the targeted nerve until the desired indicator response(s) may be obtained at smaller intensity(ies) within a target range (e.g., 0.1-1.0 mA (or 0.09-39 mA, or 0.009-199 mA), 100-300 us (or 10-1000 us, or 1-10,000 us)).

In the present teachings, the electrode of the stimulation lead may be placed and anchored at about 1 millimeter (mm) to about 100 millimeters spaced from the target nerve, more preferably from approximately at least 1, 2, 3, 4, 5, 6, 7, 8, 9, and/or 10 millimeters to about 5, 6, 7, 8, 9, 10, 15, 20, 25, 30, 40, and/or 50 millimeters spaced from the target nerve. The electrode spacing from a targeted nerve may depend on various factors, and similar stimulation settings may invoke different responses even if spaced at similar distances. Thus, electrode spacing from the nerve may be about 10 to about 20 millimeters for one target nerve at a given stimulation intensity while the spacing may be about 20 to about 40 millimeters for a second target nerve at the same stimulation intensity.

The stimulus intensities are a function of many variables, are meant to serve as non-limiting examples only, and may need to be scaled accordingly. As an example, if electrode shape, geometry, or surface area were to change, then the stimulus intensities may need to change appropriately. For example, if the intensities were calculated for a lead with an electrode surface area of approximately 20 mm$^2$, then they may need to be scaled down accordingly to be used with a lead with an electrode surface area of 0.2 mm$^2$ because a decrease in stimulating surface area may increase the current density, increasing the potential to activate excitable tissue (e.g. target and non-target nerve(s) and/or fiber(s)). Alternatively, if the intensities were calculated for a lead with an electrode surface area of approximately 0.2 mm$^2$, then the intensities may need to be scaled up accordingly to be used with a lead with an electrode surface area of 20 mm$^2$. Alternatively, stimulus intensities may need to be scaled to account for variations in electrode shape or geometry (between or among electrodes) to compensate for any resulting variations in current density. In a non-limiting example, the electrode contact surface area may be 0.1-20 mm$^2$, 0.01-40 mm$^2$, or 0.001-200 mm$^2$. In a non-limiting example, the electrode contact configuration may include one or more of the following characteristics: cylindrical, conical, spherical, hemispherical, circular, triangular, trapezoidal, raised (or elevated), depressed (or recessed), flat, and/or borders and/or contours that are continuous, intermittent (or interrupted), and/or undulating.

The present system may utilize a peripheral nerve system and method that incorporates features of the present teachings. The system and method may identify a region where there is a local manifestation of pain. The region of pain may comprise any appropriate portion of the body, e.g., tissue, skin, bone, a joint, adipose, or muscle. The system and method may identify one or more peripheral nerves (e.g., part of the peripheral nervous system) located distant from the region where pain is manifested, through which neural impulses comprising the pain pass. A given nerve that is identified may comprise a nerve trunk located in a nerve plexus, or a division and/or a cord of a nerve trunk, or a nerve branch, or a nerve plexus provided that it is upstream, proximal, superior, or cranial of where the nerve innervates the region affected by the pain. The given nerve may be identified by medical professionals using textbooks of human anatomy along with their knowledge of the site and the nature of the pain or injury, as well as by physical manipulation and/or imaging, e.g., by ultrasound, fluoroscopy, or X-ray examination, of the region where pain is manifested. A desired criteria of the selection may include identifying the location of tissue in a therapeutically effective distance from the nerve, which tissue may be accessed by placement of one or more stimulation electrodes, aided if necessary by imaging or electro-location techniques. A therapeutically effective distance may be defined to mean the placement of a lead either in contact with, or more preferably adjacent to a nerve. The nerve identified may comprise a targeted peripheral nerve. The tissue identified may comprise the "targeted tissue."

The electrodes of the electrical stimulation device may be percutaneously inserted using percutaneous leads. The system and method may place the one or more leads with its electrode in the targeted tissue in electrical proximity to but spaced away from the targeted peripheral nerve. The system and method may apply electrical stimulation through the one or more stimulation electrodes to electrically activate or recruit the targeted peripheral nerve that conveys the neural impulses to the central nervous system.

The system and method may apply electrical stimulation to peripheral nerves throughout the body. By way of a non-limiting example, the peripheral nerves may comprise one or more spinal nerves in the brachial plexus, to treat pain in the shoulders, arms and hands; and/or one or more spinal nerves in the lumbar plexus, to treat pain in the thighs, knees, and calves; and/or one or more spinal nerves in the sacral plexus, to treat pain in the thighs, calves, and feet; and/or one or more spinal nerves in the cervical plexus, to treat pain in the shoulders.

For example, if the pinky finger is the location of pain following a limb joint replacement surgery, the system and method may identify and stimulate the ulnar nerve at a location superior, proximal to, upstream, or cranial of where the nerve innervates the muscle or skin of the pinky finger, e.g., in the palm of the hand, forearm, and/or upper arm. If electrical stimulation activates the target peripheral nerve sufficiently at the correct intensity, then the patient may feel a comfortable tingling sensation called paresthesia in the same region as their pain, which overlaps with the region of pain and/or otherwise reduce pain.

It is to be appreciated that the sensation could be described with other words such as buzzing, thumping, etc. Evoking paresthesia in the region of pain confirms correct lead placement and indicates stimulus intensity is sufficient to reduce pain. Inserting a lead percutaneously may allow the lead to be placed quickly and easily.

Placing the stimulation lead 100 percutaneously in tissue in electrical proximity to but spaced away from the targeted peripheral nerve may also minimize complications related to lead placement and movement. In a percutaneous system, the stimulation lead 100 may be used because it is minimally-invasive and well suited for placement in proximity to a peripheral nerve. The lead may be sized and configured to withstand mechanical forces and resist migration during long-term use, particularly in flexible regions of the body, such as the shoulder, elbow, and knee. The lead may be sized and configured to withstand mechanical forces and resist migration during use in specific anatomical locations and/or a range of locations, such as near or in the torso, back, extremities, leg, arm, foot, neck, head, face, hand, finger, shoulder, elbow, wrist, finger joint, hip, knee, ankle, toe, pelvis, etc.

The lead may be sized and configured to withstand mechanical forces and resist migration during use in specific anatomical locations and/or to target or stimulated a specific nerve (or named peripheral nerve), such as the lumbar medial nerve and/or the lumbar medial (nerve) branch, the medial branch of the dorsal ramus, the femoral nerve and/or its branches, the sciatic nerve and/or its branches, the suprascapular nerve and/or its branches, axillary nerve and/or its branches, median nerve and/or its branches, radial nerve and/or its branches, ulnar nerve and/or its branches, musculocutaneous nerve, intercostal nerve(s) and/or its branches, lateral femoral cutaneous nerve and/or its branches, thoracic medial nerve or nerve branch, cervical medial nerve or nerve branch, occipital nerve(s) and/or its/their branches, pudendal nerve and/or its branches, ilio-inguinal nerve and/or its branches, iliohypogastric nerve and/or its branches, genitofemoral nerve and/or its branches, cranial neve(s), and/or any of the additional branches or roots of these or other nerves including other named nerves.

The conduction location or electrode may comprise a de-insulated area of an otherwise insulated conductor that may run the length of an entirely insulated electrode or a portion thereof. The de-insulated conduction region of the conductor may be formed differently, e.g., it may be wound with a different pitch, or wound with a larger or smaller diameter, or molded to a different dimension or it may not be wound at all. The conduction location or the electrode may include a separate material (e.g., metal or a conductive polymer) exposed to the body tissue to which the conductor of the wire is bonded.

The neurostimulation pulse may by monophasic (anodic or cathodic), biphasic, and/or multi-phasic. In the case of the biphasic or multi-phasic pulse, the pulse may be symmetri-cal or asymmetrical. Its shape may be rectangular or expo-nential or a combination of rectangular and exponential waveforms. The pulse width of each phase may range between e.g., about 0.1 μsec. to about 1.0 sec., as non-limiting examples.

Pulses may be applied in continuous or intermittent trains (i.e., the stimulus frequency changes as a function of time). In the case of intermittent pulses, the on/off duty cycle of pulses may be symmetrical or asymmetrical, and the duty cycle may be regular and repeatable from one intermittent burst to the next or the duty cycle of each set of bursts may vary in a random (or pseudo random) fashion. Varying the stimulus frequency and/or duty cycle may assist in warding off habituation because of the stimulus modulation.

An embodiment of a method according to the present disclosure may comprise a step of stimulating afferent and/or efferent nerve fibers in a predetermined manner to generate an action potential in the nerve fibers in an animal, such as a human, to reduce a perception of pain by the animal. According to one aspect of a method according to the present teaching, the stimulating step may comprise electrically stimulating the afferent nerve fibers. The afferent nerve fibers may also be located outside a neural receptor and outside a central nervous system of the human. The afferent nerve fibers may also be located between a neural receptor and the central nervous system of the human. The afferent nerve fibers may also innervate neural receptors, such as proprioceptors. The afferent nerve fibers may also be in neural communication with neural receptors, such as proprioceptors, and stimulated at a location that may be between the neural receptors and a central nervous system of the animal. The afferent nerve fibers may also be one or more of a plurality of types of axons, including Au axons, such as Ia and Ib axons, Aβ axons, Aδ axons, and/or C axons.

A method according to the present disclosure may further include activating efferent nerve fibers and/or stimulating efferent nerve fibers to cause a contraction of a muscle to cause a series of responsive action potentials to be generated by afferent nerve fibers. Such responsive action potentials may be sensed, and the predetermined manner of stimulation of the afferent nerve fibers is derived at least partially by approximating a characteristic of the responsive action potentials. Such characteristic of the responsive action potentials may be selected from the group consisting of: an average frequency of two or more of the responsive action potentials, an instantaneous frequency of two of the respon-sive action potentials, and a pattern of two or more of the responsive action potentials.

Another method according to the present disclosure is a method of reducing a perception of pain by an animal of a hypersensitized portion of the animal nervous system, including the step of applying electrical stimulation to at least a portion of the nervous system to cause a reduction of perception of pain by the animal, the portion including afferent nerve fibers and the stimulation may cause action potentials to be generated by or along the afferent nerve fibers. The afferent nerve fibers may be located neurologi-cally between and outside a neural receptor and a central nervous system of the human.

According to another aspect of a method according to the present disclosure, the applying step is performed for a predetermined treatment time, and the reduction of percep-tion of pain occurs at least partially during the treatment time and at least a portion of the reduction of perception of pain is maintained after the end of the predetermined treatment time.

To position an electrode in vivo, preferably while stimu-lation is being applied, the stimulation lead may be advanced (e.g. slowly advanced) towards the targeted nerve until a desired indicator response (e.g. muscle twitch, muscle con-traction, patient sensation, and/or some combination) is obtained, thereby defining an optimal placement position. The intensity may then be decreased (e.g. gradually decreased) as the stimulation lead is advanced (e.g. advanced slowly) closer to the targeted nerve until the desired indicator response(s) may be obtained at smaller intensity(ies) within the target range (e.g. 0.1-1.0 mA (or 0.09-39 mA, or 0.009-199 mA), 100-300 us (or 40-1000 us, or 1-10,000 us)) at some distance (e.g. X2 mm, where X2<X1, and (as a non-limiting example) X1 may be mul-tiple times larger than X2, such as $X1 \geq 2 \cdot X2$, or $X1 \geq 5 \cdot X2$, or $X1 \geq 20 \cdot X2$) from the target nerve. If specific response(s) (e.g. desired response(s) and/or undesired response(s)) can be obtained at a range of intensities that are too low, then the lead may be located in a non-optimal location (e.g. too close to the target nerve(s)). Non-limiting examples of ranges of intensities that may be considered too low include those that are a fraction (e.g. $<2/3$, or $<1/5$, or $<1/10$) of the intensities that obtained the desired response(s) at X1. In a non-limiting example, the electrode contact configuration may include one or more of the following characteristics: cylindrical, conical, spherical, hemispherical, circular, triangular, trap-ezoidal, raised (or elevated), depressed (or recessed), flat, and/or borders and/or contours that are continuous, inter-mittent (or interrupted), and/or undulating.

An introducer system may comprise an electrical stimulus generator, the stimulation lead 100 having a conductive distal anchor and a proximal end in communication with the stimulus generator and a needle assembly comprising a first needle comprising an outer sheath having an outer circum-ference and defining a bore wherein the outer circumference is not continuous, a second needle carried within the bore during positioning and testing of the open-coiled stimulation lead, and at least one test electrode positioned along the outer circumference and in electrically communication with the stimulus generator. The introducer system may also comprise a third needle comprising a third needle sheath having a third needle outer circumference and defining a third needle bore wherein the open-coiled stimulation lead is carried within the third needle sheath, whereby the open-coiled stimulation lead and the third needle sheath replace the second needle in preparation for deployment of the open-coiled stimulation lead.

An introducer system may comprise an electrical stimulus generator, the stimulation lead 100 having a conductive distal anchor and a proximal end in communication with the stimulus generator and a needle assembly comprising an outer sheath having an outer circumference and defining a bore, an inner needle carried within the bore during positioning and testing of the stimulation lead, and at least one test electrode positioned along the outer circumference and electrically communicating with the stimulus generator. The introducer system may also comprise a lead needle comprising a sheath having a sheath outer circumference and defining a sheath bore wherein the stimulation lead 100 may be carried within the sheath and the stimulation lead and the sheath replace the inner needle in preparation for deployment of the stimulation lead 100.

Described herein are systems, apparatuses, and methods that may conveniently provide and/or facilitate a single deployment device to incorporate implantation of the stimulation lead 100. The stimulation lead 100 may possess a generally small diameter in comparison to previous systems to enable deployment through a minimally-invasive introducer device. In an aspect, embodiments described herein may conveniently provide a single device that may locate a desired tissue region, test stimulation of the tissue region, position (or reposition) a testing signal, deploy the lead and enable its use as needed for the duration of treatment without interruption (e.g., avoiding the interruption of therapy and treatment by avoiding damage to or fracture of the lead), and enable fuller removal of the intact lead when treatment is complete. The example embodiments may also enable repositioning of the device and lead within human or animal tissue without deploying the electrode or lead until its deployment is desired by the user (e.g., the clinician). Embodiments may provide an easy to use and safe systems, apparatuses, and/or methods.

The introducing device may enable a lead to be percutaneously placed a safe distance from a surgical site, which may increase safety, minimize risk to the anatomy that is the focus of the surgery, minimize the risk of infection, and minimize the potential impact of any infection should it occur. As a non-limiting example, the device may enable placement of the lead to deliver stimulation to a nerve innervating a region, where the region may be painful or be anticipated to be painful due to a surgery (e.g., the device may enable placement of a lead to deliver stimulation to a femoral nerve, sciatic nerve, or lumbar plexus innervating a region, such as a knee which may be undergoing knee replacement surgery), and the device desirably enables the lead to be placed a safe distance (e.g., in the upper thigh, upper leg, or lower back) away from the surgical site (e.g., the knee) and/or outside of the surgical field.

The introducing device may enable a target nerve to be identified prior to lead placement and prior to lead deployment as part of a non-surgical procedure.

The introducing device can reduce lead placement and testing procedure duration when placing one or more stimulation leads. Specifically, placement and testing times are reduced in comparison to prior art systems by reducing the number of percutaneous insertions required (e.g., the insertion of a needle for test stimulation and a separate needle for lead deployment or a system in which multiple percutaneous needles/tubes/catheters are inserted to increase the size of the percutaneous entrance and allow the lead to be inserted). Thus, in contrast to prior systems requiring multiple insertions and/or separate leads to deliver stimulation, the present system allows for greater manipulation of the introducer system, particularly along its axial length (e.g., the depth to which the needle is inserted and repositioned without deploying the lead anchor. Also, the present system the stimulation lead 100 from stress and metal fatigue during the insertion procedure.

An introducing and testing system may be utilized that reduces the number of percutaneous insertions required and/or enables the goals of introducing, testing, and/or lead deployment to be achieved with a minimal number of insertions (e.g., as few as one (a single) insertion). Specifically, the stimulation testing and lead insertion/deployment may all be incorporated into a system which may require as few as one (a single) percutaneous insertion, injection, or placement.

The stimulation lead 100 may be disposed within at least the interior of outer sheath. The electrode itself may be deployed through the cavity. The lead may extend from a distal lead anchor and couples to (e.g., removably or irremovably) a stimulation signal generator or stimulator. The anchor may deliver stimulation signals both during and after it has been positioned and deployed. Further, the electrode-including the stimulation lead and anchor—may have any combination of the following on part or all of the components: a monopolar nature; a helical and/or open-coiled structure and/or closed-coiled structure with a central void that could receive a stylet; and/or multiple filars of an electrically conductive material wound together and electrically in parallel relative to one another, and the anchor may be relatively straight while the remainder of the lead is coiled.

While the particular disclosure of implantable electrode contemplates a subcomponent including a lead and anchor, the more general term "lead" can refer to the stimulation apparatus from its distal anchor all the way to its proximal connection to a stimulus generating unit, including portions that may be jacketed, covered, or coated by insulating material. In contrast, the general term "electrode" or "contact" may refer to the exposed, electrically conductive portion of the lead that is inserted into the body to deliver stimulation.

When the anchor is not deployed, a portion of the anchor may be disposed in an area between the inner sheath and the outer sheath (e.g., within the introducer device or system). The anchor may be comprised of any appropriate material, including, but not limited to a polymer, a metal, stainless steel, or a combination or two or more thereof. In one aspect, the anchor may be electrically and mechanically integral with the electrode through which stimulation is delivered.

The characteristics of the electrode contact may be designed to represent, predict, or otherwise provide information regarding the performance of the stimulation lead prior to lead deployment, particularly with respect to size, shape, material, and surface area. For example, by selecting mechanical and/or electrical properties similar to or representative of the lead electrode contact (e.g., similar impedance, contact materials such as stainless steel, and/or similar surface area such as 10 $mm^2$ or smaller or greater)), the characteristics of the test electrode contact will represent the anticipated performance of the stimulation lead. The test electrode position should be at or near the distal end (or tip) of the introducer needle such that, when the self-anchoring lead is deployed, the lead remains in close proximity to the location occupied by the test stimulation electrode. Alternatively, multiple electrode contacts may be advantageously spaced along the needle/sheath (e.g., 1 mm-30 mm intervals, preferably 1, 2, 3, 4, or 5 mm) such that test stimulation can be delivered from one or more different test electrode contacts on the same needle, thereby allowing the optimal location for stimulation to be identified while minimizing or eliminating the need to move and reposition the lead introducing system during the test stimulation/optimal location identification procedure. In such multiple test electrode configurations, test stimulation is delivered from multiple locations from one percutaneous insertion to determine the optimal deployment location for a self-anchoring, infection and migration resistant stimulation lead with a distal anchor/electrode.

In an embodiment, the anchor may fold over the inner sheath, e.g., at the distal end of the inner sheath, so the anchor may be contained in the area between the inner sheath and the outer sheath prior to deployment of the anchor, e.g., during testing and/or the locating a target tissue region. This containment of the anchor may allow for testing of tissue stimulation and reposition of a location of delivery prior to deployment of the anchor, among other potential uses.

Test stimulation used for lead deployment may be accomplished by passing electrical current into the surrounding tissue through the needles and/or sheaths or test electrode(s) situated on an exterior surface(s) thereof. The test electrodes could be formed via openings in an insulating polymeric jacket situated around the outer sheath (or, in some embodiments, the inner sheath) with current passing through the sheath itself for stimulation, or the electrodes could be discretely formed elements (possibly including discrete wiring for stimulation signals). Other arrangements contemplate the use of a conductive coating (making appropriate contact with a pulse generator/signal source) disposed along selected exterior surfaces of one or both sheaths. Alternatively, test stimulation can be accomplished through an exposed portion of the electrode itself. In this arrangement, a portion of the distal end of the lead protrudes through cavity (and, in some embodiments, cavity), while the lead itself remains in a non-deployed state (e.g., in some embodiments, the anchor portion is still held firmly within area). In either instance, after insertion of the introducer device into the tissue, test stimulation is delivered prior to the deployment and anchoring of the lead in that tissue.

In an example, the exposed exterior portion or portions of the needle include multiple test electrodes. Test electrodes may be positioned at intervals along the length of the needle and/or radially at different locations around the circumference of the needle. While some embodiments may include only a single test electrode, the use of multiple electrodes is advantageous because it enables test stimulation at multiple locations in the tissue with as few as possible (e.g., single) insertions and/or injections and/or movements of the needle, ensuring the procedure is simple and time efficient, while avoiding the need to reposition the introducer or lead to evaluate other potential electrode locations. While the outer sheath is described, the inner sheath (if used) may incorporate similar test electrodes. In this arrangement, it will be understood that the inner sheath should be sufficiently expelled through the cavity in order to expose the test electrodes to tissue intended for test stimulation, although in this arrangement the inner sheath should not be expelled so far outside of the outer sheath as to cause the anchoring system to become embedded in the tissue. Electrodes may be positioned in regular or irregular intervals, along a straight linear line or around portions or the entirety of the circumference of the needle.

Applying test stimulation (e.g., stimulation performed prior to or during lead deployment and/or repositioning) that is representative of stimulation by the lead itself is advantageous because it allows clinicians to quickly and simply identify the desired location for lead deployment through a minimal number of needle insertions, avoiding the need to reposition the needle(s) and/or lead. Minimizing needle insertions minimizes the risks and discomfort for the patient and, generally, provides a more reliable method for lead deployment in comparison to previous systems.

The position, orientation, and/or trajectory of the introducer and/or lead is important for successful lead placement by the clinician, for example under x-ray imaging, such as fluoroscope, x-ray or CT. Modifications to the existing introducer system and/or lead through the addition of radiopaque markers can simplify the lead placement procedure, reduce risk for the patient, and improve reliability of lead placement, allowing visualization of lead placement and avoiding improper or premature deployment of the self-anchoring lead. Additionally, the lead tip or needle may be coated with a radiopaque or radiodense substance (e.g., barium, radiopaque polymer) to improve visualization under x-ray imaging (e.g., fluoroscopy, x-ray, CT). Radiodense metals, e.g., platinum, gold, tantalum, or for example, a radiopaque conductive polymer, may be applied to the lead tip permitting visualization under x-ray imaging, while still enabling current flow for stimulation. As a non-limiting example, a portion of the lead, including the uninsulated or insulated wire/portion, may be coated or manufactured with a radiopaque material, such as with a titanium, tungsten, barium sulfate, and zirconium oxide, to enable better detection under fluoroscopy or x-ray. In one embodiment, the coating may be sprayed or electroplated on the lead tip. In another non-limiting example, radiodense markers may also be applied in bands or segments along the length of the needle and/or lead to be used for identification of position and depth of lead or needle in the tissue under x-ray imaging. In another embodiment, the radiopaque markers along the length of the lead could be used to assess lead depth and track lead migration during therapy, making it easier to confirm lead placement stability for continuous therapy. As another non-limiting example, the inner and/or outer sheaths may be labeled or marked with radiopaque materials to assist with lead placement under fluoroscopy and visualization of needle depth, monitoring the respective location of needles or sheaths, and proper deployment and anchoring of the lead.

The introducing device may also enable selectively self-anchoring lead and insertion system that may place a selectively self-anchoring lead in anatomical locations that are capable of movement, including but not limited to limbs, joints, back, neck, head, abdomen, torso, face, and extremities, foster tissue ingrowth that seals the skin exit site, and prevent the lead from positioning in and out of the skin, which can further minimize infection risk.

The present system may reduce lead placement procedure discomfort by limiting the diameter of the percutaneous system. Resistance to insertion through skin or tissue skin may cause additional pressure to be placed on a patient's skin and/or the device, leading to potential discomfort (e.g., pain or bruising from the pressure of insertion or from multiple failed attempts to insert needles) and/or damage or strain on the device (e.g., damage to lead or introducer, lead deployment mechanism failure). Reducing the resistance to insertion may be accomplished by limiting the diameter of the introducer system, designing or manufacturing the needle to be sharper (e.g., sharper edges of heel and/or additional bevels), or coating the surface (e.g., exterior shaft) of the needle(s). Modifying the bevel shape or sharpness of the needle(s) in the introducer system (e.g. by the addition of multiple bevels during needle manufacture or grinding or shaping the needles) may make insertion easier (e.g., requiring less force) and ensure that the lead placement procedure is more comfortable for the patient. Multiple bevels and increased needle sharpness minimize risk to patient, enable reliable insertion, and enable insertion that avoids unnecessary pressure on the lead or device. In another embodiment, a coating may be partially or completely applied along surfaces of the introducer needle(s) to reduce resistance to insertion through tissue (e.g., polymeric coating that glides through tissue easier). In one embodiment, the coating may be hydrophobic (e.g., polytetrafluoroethylene, silicon rubber), hydrophilic (e.g., polyvinylpyrolidone, polyurethanes, polyacrylic acid, polyethylene oxide), or liquid-impregnated to improve ease of insertion and maneuverability within tissue by reducing friction between skin or tissue and the needle. Modifications of the exterior of the needles that minimize insertion force required by clinicians (e.g., enabling lead placement by clinicians) and that do not produce a substantial increase in outer diameter will ensure that selective lead deployment may be performed through minimally invasive approach, using a minimal number of insertions and further minimizing risk and discomfort for the patient.

Another example is to use a plastic inner tube that is stiff enough to allow for deployment, but flexible enough that the outer anchor hook (not shown) can press in the plastic sheath's end, allowing the outer needle to be just larger than the inner tube and to completely contain the un-deployed lead. The flexible plastic sheath would also have to be flexible enough that it could be withdrawn over the lead without catching. Avoiding having the lead catch within an inner tube would be an important issue in these diameter limiting solutions where the inner needle may lead little space around the lead, which could lead to an excess of friction. A non-limiting example of a solution for this would be the use of a biocompatible lubricant applied between the parts that must move relative to each other, such as a silicon based (or other appropriate) lubricant.

Reducing the outer diameter of the system is desirable as this limits the discomfort experienced by the patient during the procedure. In the example in which a sheath over a needle is used to secure the anchor of the self-anchoring stimulation lead in place during placement/testing/repositioning, a tight fit of the outer sheath over the inner needle, which would both limit the outer diameter and better secure the anchor, could be accomplished by using a sheath material that could be shrunk, for example by application of heat or other means of causing the sheath tubing diameter to contract. This can also ease the manufacturing and assembly burden of this system, as a tightly fitting sheath would not have to be threaded over the inner needle and the anchor. The larger diameter outer sheath could easily be slid into position and then shrunk to provide a tight fit.

The introducer system described herein may also reduce the risk of problems following lead placement by reducing the risk of lead fracture. This risk reduction results from the shape of the electrode itself, both in terms of its self-anchoring, migration-and-infection-resistant small diameter helix/coils and its distal anchoring system, and from the reduced levels of stress imposed upon the lead during the insertion and test stimulation process by way of being able to retract and protect the electrode during insertion and repositioning.

Other advantages include the ability to enable the duration of the lead placement and stimulation testing procedures to be minimized. The system also limits the number of percutaneous insertions required, decreases risk to the patient, enables efficient positioning and re-positioning of the lead for stimulation testing and lead deployment, enables clinicians to position and deploy the lead correctly and optimally with minimal or no additional training, and decreases the time required to form electrical connections for testing. As a result, the therapy can be delivered to patients by clinicians in settings/scenarios that were previously burdensome, not practical and/or not possible (e.g., to treat pre-operative, pen-operative, and/or post-operative pain). This introducer also overcomes limitations of previous systems by minimizing or eliminating the need for: a) the insertion via multiple percutaneous devices; b) re-positioning of the lead; and/or c) extended periods of time required for test stimulation and/or lead placement procedures.

Manufacturing the introducer system, and particularly the outer sheath and/or stimulation lead, to incorporate easily visualized/identified indicia simplifies the lead placement procedure, reduces risk for the patient, improves reliability of lead placement, and avoids improper or premature deployment of the self-anchoring lead. The tip of the lead and/or other sections or lengths of the lead may be manufactured (e.g., coated, labeled, textured, etc.) with alternative materials that are easily detected under medical imaging, as this is important to improve ease of lead placement and detection of the device with imaging. As a non-limiting example, the lead tip or portions or segments of the lead may be textured to increase echogenicity, improving visualization under ultrasound. In another embodiment, the tightly coiled and twisted structure of the multi-filared lead wire may be braided, coiled or woven at the tip to increase reflectivity and echogenicity. Further, texturizing smooth metal or the addition of a textured conductive coating would enable better detection under ultrasound while enabling electrical stimulation. In another embodiment, the lead tip may be textured to improve echogenicity, but coated with a conductive material that results in a smooth surface that reduces potential for tissue damage, patient discomfort and enables easier removal from tissue. Alternatively, in another non-limiting example, the needle or a length of the tip may be coated, textured or marked to improve visualization under ultrasound. Modifications to the tip to increase echogenicity that increase surface area may also reduce the electrode impedance of the needle tip, enabling selective stimulation of the desired neural targets.

In another embodiment, the two introducer needles or sheaths may be labeled, coated or etched in banded pattern to mark length along the shaft. In such an embodiment, the bands or labels may be used to assist in deployment of the stimulation lead at the desired depth, used to guide movement of the needles or sheaths in relation to the other, and used to differentiate these and facilitate lead placement under ultrasound imaging. Further, the markings of the sheaths or needles could be used as a scale for distance and depth during lead placement procedures that is important for estimating distances e.g., the distance of a nearby target or non-target structure and depth of insertion. In another embodiment, the introducer needle(s) or sheath(s) may be composed of materials which to enable magnetization (e.g., ferritic stainless steel, or non-metallic magnet) for detection with advanced ultrasound needle localization systems.

The present system may comprise an electrical stimulation device having at least one stimulation lead 100 adapted for insertion within tissue of an animal body (e.g., human patient) and a pulse generator operatively coupled with the at least one lead, wherein the pulse generator is configured to stimulate at least one nerve innervating a region of pain (e.g., following development of pain that may be acute, chronic, sub-acute, persistent, post-traumatic, post-surgical, or following surgery or trauma, including limb joint replacement surgery).

The present system may further include a kit for treatment of pain following limb joint replacement surgery comprising a needle insertable into an animal body tissue, at least one stimulation lead 100 operatively inserted into the needle, wherein the needle and at least one stimulation lead 100 are inserted into an insertion point of the animal body, whereby the needle is removable from the animal body tissue and the at least one stimulation lead 100 is retained within the animal body, and a pulse generator operatively coupled with the at least one stimulation lead 100, wherein the pulse generator is configured to stimulate at least one nerve innervating a region of pain following a limb joint replacement surgery.

As non-limiting example, the target nerve may be the peripheral branches of the axillary nerve located in the deltoid muscle. Needle electrodes may be used to locate the motor point(s) of the deltoid muscle using standard locations for clinical electromyography. For example, it may be desirable to contract both the middle and posterior heads of the deltoid muscle, and thus, two needle electrodes would be used to identify the middle and posterior deltoid motor points. The motor point of the middle deltoid is identified at the midpoint between the humeral tubercle and the deltoid tuberosity. With the shoulder fully adducted and in neutral rotation, this location corresponds to approximately 3-4 cm distal to the most anterior portion of the acromion. The motor point of the posterior deltoid is identified approximately 3-4 cm posterior to the motor point of the middle deltoid. Once these motor points are located (as evidenced by strong but comfortable muscle contractions and/or comfortable paresthesia sensation evoked during test stimulation), test stimulation may be delivered between the motor points using a third needle electrode to evoke contractions in both heads simultaneously. If necessary, the needle electrode can be repositioned toward the muscle with the weaker response until both heads contract strongly. The stimulation lead 100 should be placed in a preferred location, as described above. In this location, the patch assembly may be placed on the insertion of the deltoid muscle at the deltoid tubercle or in an alternative location.

The present system provides a method of activation of nerves that enables changes in central nervous system processing in such a way that can outlast the duration of therapy (e.g., on short term and/or long term). Modulation of central spinal processing brought about by activation of paraspinal muscles, which may be activated by peripheral nerve stimulation and can outlast stimulation of the nerves that produced contraction of the muscles on the short term (e.g., second, minutes and/or days) or long term (e.g., days, weeks, months and/or years) after stimulation stops being applied to nerves. This sustained therapeutic benefit offers an advantage over the prior art and existing therapies, where continuous or long-term intermittent stimulation is required to produce pain relief, and/or sustained, lasting benefit (e.g., relief of pain or improvement in function) cannot be achieved after terminating the therapy. Furthermore, the present system may provide long-lasting modulation of central pain processing with a system that is minimally-invasive (e.g., percutaneous electrode insertion), temporary (e.g., short-term therapy administered over a period of weeks), safe (e.g., coiled lead design has negligible risk of infection or device-related adverse events) and reliable (e.g., self-anchoring lead prevents lead migration, ensuring comfortable, uninterrupted therapy). As a further example, the present system may enable a short-term therapy (e.g., a temporary percutaneous system using a percutaneous lead coupled to an external stimulator) to provide long-term pain relief (e.g., by modulation of central pain processing).

The insulated wire may be formed into a spiral or helix as has been found to accommodate high dynamic stress upon muscle flexion and extension, while simultaneously retaining low susceptibility to fatigue. The outer diameter of the helically formed electrode lead may be approximately 500, 550, 560, 570, 580, 590, 600, 610, 620, 630, 640, 650, 660, 670, 680, 690, and/or 700 μm and it may be encased or filled with silicone or the like. Alternatively, the lead may have additional or fewer filars, may be made out of a different material (e.g., another metal, conducting polymer), may be insulated with another material, or may not be insulated.

As mentioned above, a proximal end of each of the lead may be located exterior to the patient's body when in use. The proximal end may include a deinsulated length for connection to an electrical connector in combination with the remainder of the electrode leads. The deinsulated portion may be located on any portion of the proximal portion of the lead located outside of the body. In some embodiments, the distal end of each lead which may be inserted directly into tissue, may also include a deinsulated length. The deinsulated length may act as the stimulation electrode. At least a portion of the deinsulated length may be bent or otherwise deformed into a barb or anchor. This may anchor the electrode in the selected tissue. A taper, made from silicone adhesive or the like, may be formed between the deinsulated distal end and the insulated portion of the lead to reduce stress concentration. The electrode may be placed anywhere along the length of the lead; the present teachings are not limited to the aforementioned locations. The electrode may be a conductive contact connected (e.g., welded, via adhesive) to the lead. Alternatively, the lead may be threaded (e.g., like a screw), and may be inserted into the tissue (e.g., pushed, deployed, screwed, etc.), which may mechanically secure the lead in the tissue.

The associated lead may exit the patient percutaneously, i.e., through the skin, for connection to the stimulation pulse generator. Each of the electrodes may be implanted or otherwise inserted into the select tissues by use of a needle. The needle may be straight or may be hooked. Alternatively, the lead may be inserted using other hollow tubes (e.g., cannula, catheter). Once the lead is implanted as desired, its proximal end may be crimped into a common connector that may mate with the cable assembly. The cable assembly may be, in turn, connected to the pulse generator through the connection socket. Alternatively, the electrodes may be connected directly to the stimulator. Alternatively, each electrode may be connected to an individual connector. Alternative means of securing the leads to the connector may also be used (e.g., magnetic, adhesive).

The present percutaneous stimulation system may allow for precise selection of nerve stimulation and use of two or more stimulation electrodes and channels. Alternatively, a system may use one stimulation electrode. The system in accordance with the present technology may use two or more electrodes, each connected to an independent electrode stimulation channel, and a single reference electrode that may be a percutaneous, surface electrode, the case of the stimulator (if implanted), or an implanted electrode. Alternatively, there may be more than one reference electrode, and each stimulation channel may have its own reference electrode. The electrode stimulation channels may not be independent, i.e., the same stimulation may be delivered to multiple channels at once.

According to one method of treatment according to the present teachings, the stimulation lead(s) 100 may be placed to target the nerve(s) innervating paraspinal musculature (e.g., dorsal ramus, spinal nerve, distal branches, etc.) in the regions of back pain, although this approach may be generalized to any muscle in the back, including, but not limited to, multifidus, longissimus, iliocostalis, spinalis, latissimus dorsi, rhomboid, serratus posterior, oblique external, oblique internal, quadratus lumborum, psoas major, psoas minor, trapezius, levator scapulae, splenius capitis, splenius cervicis, semispinalis muscles, rotatores muscles, rectus capitis posterior muscles, interspinales, levatores costarum, obliquus capitis inferior muscle, obliquus capitis superior, rectus capitus posterior major, and rectus capitus posterior minor, and the leads may be placed in any tissue.

According to an exemplary method associated with the present stimulation system, in accordance with various embodiments described here, the order of procedures and/or interventions used for lead placement and treatment may be predefined. As a non-limiting example, the clinician may initiate the lead placement procedure by identifying the regions of back pain and/or reviewing anatomy of paraspinal muscles and spine with medical imaging, as may be needed to sufficiently plan needle insertion and lead deployment. Insertion of the test needle and test stimulation may be used to activate nerve and produce contractions in paraspinal muscle(s), which may then be used to evaluate the extent and selectivity of nerve activation and may be used to inform the need to reposition needle location. The test needle may then be removed. In this non-limiting example, following identification of a location that produces desired neural and muscular response to stimulation, the introducer and lead may be inserted in the same trajectory (e.g., insertion location, angle, depth, etc.), testing may be conducted, and nerve activation and muscle contractions evaluated. The introducer and lead may be repositioned as needed to generate desired activation of selected nerve(s) and paraspinal muscles and/or additional leads inserted to achieve desired total effect of stimulation. Following deployment of the lead(s), the introducer(s) may be removed and the leads connected to the external pulse generator for use at home for a prescribed, temporary period of time (e.g., four weeks). At the end of the temporary therapy, the leads may be easily removed through an appropriate approach (e.g., through gentle traction) and the therapy discontinued. In the event of the need for an increase in therapy duration, the patient may undergo implantation with an implanted lead and/or pulse generator to enable sustained pain relief with long-term use of the therapy.

Leads with stimulating electrodes may be placed (e.g., in any tissue, at any distance from the nerve and/or muscle) to target the dorsal (posterior) ramus and/or branches of the spinal nerves to yield activation of paraspinal muscle(s) and this approach may be generalized to produce activation and/or sensation in any nerve branch and/or muscle in the back, including, but not limited to, multifidus, erector spinae, longissimus, iliocostalis, spinalis, latissimus dorsi, rhomboid, serratus posterior, oblique external, oblique internal, quadratus lumborum, psoas major, psoas minor, trapezius, levator scapulae, splenius capitis, splenius cervicis, semispinalis muscles, rotatores muscles, rectus capitis posterior muscles, interspinales, levatores costarum, obliquus capitis inferior muscle, obliquus capitis superior, rectus capitus posterior major, and rectus capitus posterior minor.

An embodiment contemplates a system to alleviate pain following surgical amputation or removal of an extremity, limb, body part, or body tissue including any combination of the following features:

The electrical stimulation includes a first parameter selected from a group consisting of: frequency, pulse duration, amplitude, duty cycle, pattern of stimulus pulses, polarity, a predetermined number of phases, and waveform shape; and the electrical stimulation includes a second parameter selected from a group consisting of: frequency, pulse duration, amplitude, duty cycle, pattern of stimulus pulses, polarity, a predetermined number of phases, and waveform shape;

The distance between the targeted nerve and the lead/electrode must be sufficient to activate the targeted nerve (as noted above, preferably falling between 5.0 to 30 mm but also including any combination of numbers taken to the hundredths decimal place between 0.001 and 100.00 millimeters) away from the targeted peripheral nerve. As non-limiting examples, the lead could be placed at 1, 2, 3, 4, 5 to 10, 15, 20, 25, 30, 35, 40, or 50 mm away from the targeted nerve, so long as the nerve is activated and the lead avoids physical contact of any portion of the electrode (i.e., the exposed, stimulating surface) with the targeted nerve. As noted throughout, and particularly in this paragraph, any disclosed range or combination of ranges may display inherent advantages in comparison to the previous teachings in this field.

Any combination of stimulus parameters that evoke sensation(s) may be used. The stimulation parameters may include, but are not limited to frequency, pulse duration, amplitude, duty cycle, patterns of stimulus pulses, and waveform shapes. Some stimulus parameters may evoke a more desirable response (e.g., more comfortable sensation, or a sensation that may be correlated with or specific to the specific target nerve fiber(s) within the targeted peripheral nerve.

Specific embodiments of the present teachings may include any combination of the following features: (i) a helical, wire electrode, carried within an introducer (e.g., a disposable hypodermic needle or sheath); (ii) an adhesive patch at least partially securing a proximal end of the electrode protruding from the body; (iii) a lead connector, fixed to the proximal end of the electrode; (iv) a patient cable detachably connected to the lead connector; (v) a stimulator pod, including a power source and a return electrode, detachably connected to the patient cable and forming an electrical connection between the pod and the electrode to deliver therapeutic stimulation; (vi) a controller pod in communication with the stimulator pod; (vii) a programmer unit in communication in the controller pod and/or stimulator pod wherein the programmer unit selectively delivers instructions to inform the therapeutic stimulation; (viii) the electrode, the lead connector, patient cable and stimulator pod form a series of detachable connections having tension and, in response to a disconnection force, at least one of the following occurs: the tension is temporarily reduced and the patient cable detaches from the lead connector; (ix) at least one of the detachable connections is established by way of at least one selected from: a magnet and a releasable, spring-loaded connection, a connector having a predefined holding strength; (x) the programmer unit communicates with the controller pod by way of a wireless connection; (xi) the needle includes at least one test stimulation electrodes, controlled by the controller pod to aid in the positioning of the electrode; (xii) the needle includes at least one test stimulation electrodes, controlled by at least one of the controller pod and the programmer pod to aid in the positioning of the electrode; (xiii) the lead connector is bifurcated to enable connection of a plurality of electrodes; (xiv) the patient cable comprises a plurality of segments in which each segment is detachably connected; (xv) a plurality of stimulator pods may be provided in combination with a plurality of electrodes and the controller pod coordinates stimulation among the stimulator pods; (xvi) the stimulator pods communicate wirelessly with the controller pod; (xvii) the lead connection further comprises a mechanical connector that receives and holds the proximal end while maintaining an electrical connection between the electrode and the patient cable; (xviii) the mechanical connector releasably and resettably moves in response to the force; (xix) the lead connector mechanically secures the lead and electrically connects to it in response to a force applied by the user; (xx) the mechanical connector comprises a rotating element; (xxi) the mechanical connector comprises a funnel that may have a controllably collapsible segment and wherein the proximal end of the lead received through said funnel and said controllably collapsible segment engages a portion of the electrode close to the proximal end; (xxii) the rotating element of the lead connector is electrically connected to the lead and to the series of detachable connections ending at the stimulator pod; (xxiii) at least one of the stimulator pod and the controller pod provide a user alert when a predetermined amount of force is applied, e.g., an amount to dislodge the patient cable; (xxiv) the user alert includes at least one of the following: a visual cue and an auditory cue; (xxv) the magnet comprises at least one insert molded neodymium magnet; (xxvi) the magnet is shielded to reduce unintended magnetic fields and concentrate or focus the filed between the two ends of the breakaway mechanism; (xxvii) the tension is reduced to a predetermined level and, upon the force exceeding the predetermined level, the patient cable detaches; (xxviii) the predetermined level is less than or equal to a fraction (e.g., one half, 90%, 80%, 70% etc.) of a force required to change position of the lead connector on the body; (xxix) at least one end of the patient cable includes a connection member that is mated to a corresponding connection member on at least one of the lead connector and the stimulator pod; and/or (xxx) there may be a plurality of mated connection members and each set of mated members has a unique shape to avoid improper connections.

A percutaneous electrical stimulator system may include an electrode percutaneously insertable into a patient, an adhesive bandage at least partially securing a proximal end of the electrode protruding from the patient, a lead connector, fixed to the proximal end of the electrode, a patient cable detachably connected to the lead connector, and a stimulator connected to the patient cable and forming an electrical connection between the stimulator and the electrode to deliver therapeutic stimulation.

The percutaneous electrical stimulator system described may include any combination of the following: (i) the electrode, the lead connector and the patient cable form a series of detachable connections having tension and, in response to a disconnection force, at least one of the following occurs: the tension is temporarily reduced and the patient cable detaches; (ii) at least one of the detachable connections is established by way of at least one selected from: a magnet and a releasable, spring-loaded connection, a mechanical connection; (iii) a portion of the series of detachable connections is engaged via a rotating element, said rotating element adjusting the tension in response to the disconnection force; (iv) a controller in communication with the stimulator; (v) the stimulator communicates wirelessly with the controller; (vi) a programmer unit in communication with the controller wherein the programmer unit selectively delivers instructions to inform the therapeutic stimulation; (vii) the programmer unit communicates with the controller by way of a wireless connection; (viii) at least one of the stimulator and the controller provide a user alert when the response to the force occurs; (ix) the user alert includes at least one of the following: a visual cue, tactile cue and an auditory cue; (x) a programmer unit in communication with the stimulator, wherein the programmer unit selectively delivers instructions to inform the therapeutic stimulation; (xi) the lead connector is plurally split to enable connection of a plurality of electrodes; (xii) the patient cable comprises a plurality of segments in which each segment is detachably connected; (xiii) a plurality of stimulators are provided in combination with a plurality of electrodes and wherein the controller coordinates stimulation among the stimulator; (xiv) the stimulators communicate wirelessly with the controller; (xv) the lead connection further comprises a mechanical connector that receives and holds the proximal end while maintaining an electrical connection between the electrode and the patient cable; (xvi) the mechanical connector releasably and resettably moves in response to the disconnection force; (xvii) the mechanical connector comprises a rotating element; (xviii) the mechanical connector comprises a funnel with a controllably collapsible segment and wherein the proximal end received through said funnel and said controllably collapsible segment engages a portion of the electrode proximate to the proximal end; (xix) the magnet comprises at least one insert molded magnet formed from at least one of neodymium, samarium cobalt, alnico, and ferrite; (xx) the magnet is shielded to reduce unintended magnetic fields and/or to concentrate intended magnetic fields from the magnet; (xxii) the tension is reduced to a predetermined level and, upon the disconnection force exceeding the predetermined level, the patient cable detaches; (xxiii) the predetermined level is less than or equal to a percentage of force required to change position of the electrode within the patient; (xxiv) at least one end of the patient cable includes a connection member that is mated to a corresponding connection member on at least one of the lead connector and the stimulator; (xxv) there are a plurality of mated connection members and each set of mated members has a unique shape to avoid improper connections.

A percutaneous electrical stimulator system may include an electrode percutaneously insertable into a patient, a lead extending from the electrode, a lead connector, fixed to the lead, a patient cable detachably connected to the lead connector, and a stimulator connected to the patient cable and forming an electrical connection between the stimulator and the electrode to deliver therapeutic stimulation. The percutaneous electrical stimulator system describe above may include a lead that is a helical wire lead with the electrode integrally formed at an end thereof.

A percutaneous electrical stimulator system may include a wire electrode percutaneously insertable into a patient, the electrode having a proximal end extending from the patient when inserted therein, a lead connector, fixed to the proximal end of the electrode, a patient cable detachably connected to the lead connector, a stimulator connected to the patient cable and forming an electrical connection between stimulator and the electrode to deliver therapeutic stimulation. The percutaneous electrical stimulator system describe above may comprise any combination of the following: a controller in communication with the stimulator wherein the electrode, lead connector and patient cable form a series of detachable connections having tension and, in response to a disconnection force, at least one of the following occurs: the tension is temporarily reduced and the patient cable detaches; at least one of the detachable connections is established by way of at least one selected from: a magnet and a releasable, spring-loaded connection; the electrode is covered by an electrical insulation except at a distal end thereof; and the mechanical connector comprises a rotating element providing motion and force to cut or pierce the electrical insulation and to mechanically secure the lead.

The percutaneous stimulation system may include a stimulation lead that may be initially introduced to the body by way of a hypodermic needle or introducer or any other method of insertion. The present teachings are not limited to a specified type of insertion method or apparatus. Any appropriate system may be utilized without departing from the present teachings. The electrode may include a lead extending therefrom. The lead may possess a generally small diameter in comparison to previous systems.

The properties of the coiled structure, wire(s) or lead(s) are designed to match the tissue sufficiently closely to ensure that the device does not fracture or break while indwelling in the tissue. It is also to be appreciated that the properties of the coiled structure, wire(s) or lead(s) are can also be designed (e.g., intentionally) to produce the appropriate mismatch with the properties of the tissue to ensure that the device produces a response in the tissue that produces pain relief. The stiffness of a coiled wire lead or spring-like device is directly affected by parameters including, but not limited to, the thickness of the wire, the number of filars in the wire (e.g., if a multi-filared wire), the thickness of coating(s) on the wire, the density or turn rate or spacing or number of coils, and/or the outer diameter of the coils. As a non-limiting example, increasing the diameter of the wire in a coiled lead will lead to corresponding changes in the stiffness of the spring, coiled lead, and/or cable (or spring-like or cable-like structure). Increasing the stiffness can correspondingly increase the forces generated by the spring, coiled lead, and/or cable (or spring-like or cable-like structure) upon bending, compression, or stretching, and/or the forces required to bend, compress, or stretch the spring, and can cause, enable, produce, elicit, evoke, facilitate, or promote tissue response(s) (e.g., in muscle and/or muscle tissue, adipose and/or adipose tissue, nerve and/or nervous tissue, connective tissue, skin and/or skin tissue, etc.) that lead to reduction of pain and/or other desirable responses. As another non-limiting example, the stiffness of the coiled lead may fall within an optimal range of stiffness that produces a therapeutic window for the desirable effects (e.g., pain relief) of the present system. As another non-limiting example, the properties of the structure may be designed, made, or created such that it matches or approximately matches or approximates the properties of the tissue and healthy tissue response (e.g., fibrotic growth or ingrowth) is prompted, which can include tissue growth around the structure as well as growth in between the coils of the structure because the structure is sufficiently flexible to allow such growth and the tissue that the structure causes, enables, produces, elicits, evokes, facilitates, promotes growth of which, to grow, and/or that grows in, on, around, and/or near the structure is desirably connected to tissue.

One embodiment of the device and system utilizes an electrode that is designed to anchor in tissue, such as tissue other than that of the peripheral nerve (e.g., muscle, adipose, connective, or other tissue) and deliver electrical current that can affect non-neuronal or neuronal cell function and/or activity and produce pain relief.

The lead is flexible, self-anchoring, migration resistant, fracture resistant, multi-fault tolerant, and infection resistant. The flexible coiled leads are designed specifically for PNS to reduce migration and fracture. Both the temporary percutaneous lead and fully implantable lead have a coiled structure, allowing the lead to flex and bend when subjected to forces rather than migrate or fracture. There may be one or more coils, with the coils composed of bundles of conductive wires. Each of the conductive wires, as well as the coils, are wired in parallel to the electrical stimulation/pulse generator to ensure that a fracture sustained in a single wire does not inhibit therapeutic pulses delivered by the lead as a whole. The interstices of the coils may allow tissue ingrowth to better secure the lead within the patient's body, thereby reducing lead migration.

Also, the leads may have anchors at their terminal stimulating ends to secure the lead in the tissue, increasing resistance to lead migration. These anchors are designed to flex avoid damaging tissue during removal. To the extent distal or other anchors are provided on the lead, additional migration protection can be realized.

The migration-resistant leads have been placed in and near mobile anatomical structures (e.g., joints in the arms, legs, and torso) and have been proven effective for peripheral nerve stimulation and generating comfortable sensations covering the regions of pain to relieve chronic pain.

The temporary lead used during the stimulation trial (preliminary treatment) is a single, helical coil wound from a multiple-filar stainless steel wire. The plurality of filars in the wire core of the lead is independently connected to the stimulator and gives rise to its multi-fault tolerant traits. Specifically, the multiplicity of filars and filaments enables the lead to continue to function and deliver therapy reliably via a single point of contact proximate to the nerve(s) even if a potential fracture (e.g., fault) occurs in one or more of the conductive or filars. For example, because the conductors are wired (connected) in parallel to the same pulse generator, one or more can break and yet the system as a whole can continue to function as designed, continuing to provide pain relief to the patient.

The coiled implantable lead may also be used for long-term pain relief.

The use of two or more layers of filars within the lead enables the lead to sustain multiple local failures along the length of the lead (either in the filars of wire comprising the coils or even in the entirety of one of the coils) while continuing to deliver effective therapy because the wires and the coils are electrically coupled to the same stimulation source.

The percutaneous lead reduces the risk of infection by limiting both pistoning and the size of the exit site through the skin. The coiled design reduces pistoning by allowing the lead to stretch and compress, minimizing movements in or out of the skin.

Additional shielding may be provided to allow the pulsed signals delivered by the electrode to be directionally transmitted toward a desired portion of the body and away from the surface of the skin and towards the nerves. In practice, the electrode portion of the lead necessarily comprises two exposed ends, with a middle section disposed between the ends.

When current is delivered to the lead, the pulses generated by the electrode (and delivered as therapeutic signals to the patient) tend to have their greatest current density at the two exposed ends. In contrast, the middle section tends to have significantly reduced current.

In any event, by positioning the terminal ends of the electrode, the treatment can be delivered with a single electrode. This approach enables a smaller lead and allows for more versatility in terms of its placement, particularly in view of the mobility patients expect and need to retain in order to conduct daily activities. Notably, the length of the exposed portion of electrode may be adjusted to better coincide with the targeted area or areas such as those of the occipital nerve.

Multiple leads having the construction described above may also be used. However, in this case, only one lead and one electrode is required to target one or more of the nerves. In this manner, the overall size of the system required to deliver the therapy is once again minimized The leads may be placed be placed in the transverse plane, or parallel to at least one of the sagittal and coronal planes, depending upon the findings established during the verification step. As above, this may enable treatment of multiple locations and/or multiple occipital nerves by only one lead.

For purposes of this present disclosure, the transverse plane (also called the horizontal plane, or transaxial plane) is an imaginary plane that divides the patient's body into superior and inferior parts. The sagittal plane is an imaginary plane parallel to the sagittal suture so as to divide the patient's body into left and right. The coronal plane (or frontal plane) divides the body into dorsal and ventral (e.g., back and front or posterior and anterior) portions. In a non-limiting example, leads may be placed intramuscularly near the occipital nerves. This may increase the stability of the lead (e.g., increasing resistance to migration) and allow the lead to be placed farther from cutaneous fibers to avoid cutaneous discomfort. In another non-limiting example, stimulation parameters may be delivered such that the activation of motor fibers may be avoided (e.g., through use of low pulse durations). Placing leads deeper (e.g., farther away from the skin surface) minimizes skin erosion, as can occur with larger more rigid leads. In a non-limiting example, the intramuscular placement may be at a level before or after nerves emerge from muscles (e.g., in the neck) and become superficial (i.e., subcutaneous). In another non-limiting example, leads could be placed intramuscularly closer to nerve roots to stimulate more than one occipital nerve (e.g., greater, lesser, third) simultaneously. In another non-limiting example, intramuscular placement of the lead may enable the insertion of the lead below the hairline in the back of the head, which does not require the hair to be shaved or removed for insertion.

It is to be appreciated that the present system enables an optimal lead to be designed, configured, and/or manufactured to maximize its utility, ease of use by the user, such as the patient, caregiver, physician, and/or (other) clinician. Because the stimulation lead needs to have a withdraw or withdrawal force (e.g., the force required to pull the stimulation lead from the patient or the tissue (e.g., and fully remove the lead) without any other intervention, incision, treatment, or surgery) that is high enough to enable the lead to remain in the patient for the period that the lead is in use or intended to be in use to deliver stimulation (e.g., diagnostic or therapeutic stimulation) but not so high as to be painful and difficult to remove, the present system enables the lead to be designed, configured, and/or manufactured to produce withdrawal forces within a desirable range or a prespecified range that enables or causes the lead to retain the correct or optimal location in which it is placed (e.g., for the duration of its intended use) and also enables or causes the lead to be able to be removed when and how it is desired or needs to be removed (e.g., with simple tension applied by the patient, caregiver, physician, and/or other clinician (e.g., by hand and with a single hand or a single finger (or with two hands or multiple fingers if desired) without any adverse or unwanted events or effects. The present system enables the stimulation lead 100 to be retain its position when the tension or tensile force is less than a specified or prespecified amount (e.g., less than approximately or within the range of 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.2, 2.4, 2.6, 2.8, 3.0, 3.2, 3.4, 3.6, 3.8, 4.0, 4.5, 5, 6, 7, 8, 9, 10, 11, 12, 13, 14, 15, 16, 17, 18, 19, 20 N, or more) and enables the lead to be easily removed or withdrawn (e.g., without surgery) when the tension or tensile force is more than a specified or prespecified amount (e.g., more than approximately or within the range of 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.2, 2.4, 2.6, 2.8, 3.0, 3.2, 3.4, 3.6, 3.8, 4.0, 4.5, 5, 6, 7, 8, 9, 10, 11, 12, 13, 14, 15, 16, 17, 18, 19, 20, 25, 30, 40N, or more). An example of the application of the tensile forces is shown in FIG. 24C. Examples of the testing device or devices utilized in testing such tensile forces are shown in FIG. 25.

As a nonlimiting example, the last (or first) portion (e.g., the distal or proximal end) of the lead may not be covered by the insulation or may have the insulation removed (partially or completely during the manufacturing process and/or during use after manufacturing). For example, the end of the lead may have the insulation not present or removed (e.g., by any method, such as thermally, such as via ablation and/or heat, mechanically, such as via stripping, chemically, such as by a peel or by chemicals, electrically, or otherwise). The present system enables the dimensions of the lead that will form an electrical contact, conducting surface or area, and/or electrode to be tuned and/or selected from a range, such as a length of approximately 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.2, 2.4, 2.6, 2.8, 3.0, 3.2, 3.4, 3.6, 3.8, 4.0, 4.5, 5, 6, 7, 8, 9, 10, 11, 12, 13, 14, 15, 16, 17, 18, 19, 20, 25, 30, 35, 40, 45, and/or 50 mm or more.

A portion of the body of the lead may be covered in insulation such that the outer diameter of the stimulation lead is about 300 microns (or micrometers), e.g., within 10% larger or smaller of such target, or desirably 240 to 280 microns. The insulation portion may comprise about 70 microns, e.g., within 10% larger or smaller of such target, or desirably 50 to 70 microns.

The present system overcomes multiple challenges and limitations of the prior art. Existing leads (e.g., in the prior art) have shown a risk of failure, fracture, or breakage at, near, on, or around the anchor(s), such as at the bend, juncture, or junction between the anchor(s) and the body of the lead (or lead body), including at the location on the lead where the anchor bends since this may be a part of the lead (in the prior art) that is weaker than the rest of the lead (or one of the weakest parts of the lead). The present invention has overcome the multiple challenges (e.g., simultaneously) that have conventionally caused this to be a weak spot and location for failure (in the prior art).

The present system may prevent the different and multiple types of mechanical stresses and strains that are placed on the lead (or to which the lead is subjected) from causing unwanted damage to the lead, such as preventing the lead anchor from being weakened during the manufacturing process (e.g., avoiding a kink in the lead, electrode, contact, anchor and/or the bend, junction, or junction between them (e.g., between anchor and the rest of the lead). The present system may incorporate the benefits of a living hinge design while avoiding the disadvantages of a living hinge (such as the thinness, risk of fracture and failure) and while incorporating additional advantages (such as enabling the anchor angle, orientation, and shaped to be reversibly adjusted and/or positioned as needed for each stage or phase of use of the lead)

The stimulation lead 100 may have more than one angle that needs to be designed and/or optimized to tune and/or optimize the overall performance while reducing or avoiding undesirable outcomes of the device, patient, and/or user. There may be a first angle between the anchor or the axis of the anchor (e.g., the central or longitudinal axis along the midline or long axis of the anchor) and the lead body and/or the uninsulated (or remainder of) the uninsulated portion, electrode, or contact of the lead (e.g., excluding or not including the anchor) or the axis of the lead body and/or the uninsulated (or remainder of) the uninsulated portion, electrode, or contact of the lead. The first angle may be defined by the intersection of two lines drawn from a first axis (e.g., of the anchor) and a second axis (e.g., of the lead body. The stimulation lead 100 enables the first angle to be selectively or reversibly changed, held constant or stabilize, held or stabilized within a range, to perform or enable the performance of multiple desirable functions throughout the life and use of the lead (e.g., in multiple phases of use of the lead). There may also be a second angle or secondary angle that is defined differently. The second angle may be defined by two tangent lines of two nearby points on a filar, layer, strand, wire, coil, or other part of the lead. The first angle may also be considered a macro angle or large scale angle while the second angle may be considered a micro angle or a small scale angle because the first angle can be used to measure the angle, degrees, bend, curve, and/or curvature over a large or larger portion, length, area, part, or scope of the lead while the second angle can be used to measure the angle, degrees, bend, curve, and/or curvature over a small or smaller portion, length, area, part, or scope of the lead. Optimizing the multiple angles (e.g., the macro and micro angles) of the stimulation lead 100 in absolute terms and/or relative to each other can be important to facilitating reliable manufacturing, function, and performance of the lead and portions of the lead while avoiding unwanted effects or results. It can enable the lead to fit within the introducer, remain correctly positioned in the introducer prior to deployment, deploy correctly when desired by the user, anchor (reversibly) in tissue in the patient in the correct location (e.g., as determined during a placement procedure and/or testing, such as stimulation testing), facilitate the correct or optimal level of tissue growth at, around, near, surrounding, and/or against the anchor (e.g., generating or enabling sufficient tissue growth or ingrowth to minimize, inhibit, or prevent unwanted movement of the electrode, contact, anchor, and/or lead while the lead is intended to be or remain implanted, while stimulation is being delivered, and/or during treatment of a patient) while preventing excessive or too much tissue growth or level or tissue growth at, around, near, surrounding, and/or against the anchor (e.g., avoiding or preventing the generation of too much tissue growth that could undesirably require the withdrawal force (force needed to intentionally remove, extract or withdraw the lead (such as at the end of treatment or therapy)) to exceed the tensile strength of the lead and/or any part or portion of the lead), enabling the lead to function as needed during the treatment period and also be removed intact without fracturing or failing at the end of the treatment period.

At least one embodiment of the stimulation lead 100 overcomes limitations of previously existing lead designs in which the anchor(s) was or were not formed into a single wire or strand and was instead only a single filar or filament or multiple filars, filaments, or wires (where each wire was formed by or from only a single filar or filament). The stimulation lead 100 provides more strength; tensile strength; resistance to fracture; desirable resistance, tolerance, or durability to withstand bend and/or shear forces, especially repeated application of one or more forces. The stimulation lead 100 overcomes limitations of the prior art and existing designs by reducing the potential for unwanted drag or resistance of the tissue to intentional withdrawal of the lead. While previous existing designs for anchors could create a splayed formation in which the tips of the multiple filars at the end of the leads (in the prior are) which may serve as an anchor or to anchor the lead such that the profile of the leads (of the prior art) were (or could be) wider at the far or distal end of tip of the lead (e.g., the end closest to the target location and farthest from the skin) than other parts of the lead, meaning that removal would either need to be surgical or upon attempted nonsurgical removal of the lead, the distal most part of the lead could undesirably function like a parachute, net, or other structure that creates drag when being pulled through a medium, such as tissue. The stimulation lead 100 overcomes the challenges of drag or unwanted mechanical resistance created by the prior art through at least one or more (e.g., multiple) design features simultaneously.

The stimulation lead 100 helps ensure that no distal part of the lead creates a profile or footprint that is larger than any portion of the lead that is more proximal (e.g., meaning that the tunnel in the tissue through which the lead may be intentionally withdrawn or removed with optimal or minimal traction, tension, or tensile force is always sufficiently large enough to permit nonsurgical removal of the entire lead and/or no part of the lead becomes undesirably retained or no part of the lead gets stuck because each subsequent part of the lead is at least as small in profile or cross-sectional footprint as the prior part of the lead (that is in front of the lead during removal in the direction that it is being removed or withdrawn or pulled out).

Additionally, the anchor 106 can be formed by a straight or relatively or approximately straight portion of the lead that is not coiled (or non-coiled) that provides further advantages on their own merit and when combined with other features of the lead. The anchor 106 can be formed in such a way that it is not coiled (e.g., not coiled as the other part of the lead is coiled or not formed into either a closed or open coil and not formed into a helix) but is still composed of multiple layers of filars which may be wound (e.g., wound in opposing directions or lays relative to each other and around the innermost filar). The anchor 106 has a straight or approximately straight portion overcomes multiple limitations of the prior art (e.g., that used coiled anchors that may have been formed by bending the coiled portion of the uninsulated section of lead). This prevents unwanted and unnecessary tissue ingrowth into, at, and/or around the anchor 106 and prevents the creation of normal forces (or forces perpendicular to the longitudinal axis of the anchor upon intentional withdrawal. This feature enables the amount of force required to withdraw the lead to be tuned, specified, or prespecified by only enabling or allowing the tissue to create an anticipated and calculated amount of force against the anchor (e.g., caused by friction of the tissue against the straight anchor and/or by the tissue pushing against the anchor while it remains in the acute angle formation, meaning that the anchor can be designed to bend (e.g., bend such that the axis of the anchor becomes aligned with the axis of the lead body and the first angle desirably changes (or is caused to change) from an acute angle or from 90 degrees or less to an obtuse angel or to more than 90 degrees at a prespecified force or level of tension (e.g., withdrawal force or range of tension to withdraw the lead) to enable the anchor to slide out through the tissue.

The anchor 106 overcomes limitations of the prior art by ensuring it is not weaker and/or is at least as strong or stronger than the body or the lead and/or other parts and/or all other parts of the lead. While prior art or existing leads struggled and/or failed to sufficiently and/or correctly anchor the lead or otherwise retain its location in the tissue in the patient without risking or causing the potential for the lead to fracture and leave unwanted or undesired fragments of the lead behind (e.g., leaving pieces of the lead and/or its anchor or anchoring material in the tissue when removal or withdrawal was attempted) or requiring surgery or an invasive procedure to remove or attempt to remove the lead, the stimulation lead 100 has overcome these challenges. The stimulation lead 100 achieves, retains, and/or maintains the correct location for the duration of treatment (e.g., resisting unwanted dislodgement, movement, and/or migration) and also be intentionally removed fully intact by the patient, clinician, physician, and/or caregiver while avoiding surgery and avoiding failure or fracture or breakage (in whole or in part) of the lead and avoiding leaving behind in the tissue any fragment, piece, or remaining aspect or remainder of the lead, ensuring the full lead can be easily withdrawn in its entirety by ensuring the force(s) required to withdraw the lead at any timepoint before, during, and/or after treatment or therapy or the treatment period are less than the force required to damage, fracture, or break the lead or any part of it (e.g., are less than the tensile strength or force of the lead, including the minimum tensile strength of the lead or the tensile force that any part (or all parts) of the lead can withstand and/or tolerate).

The stimulation lead 100 helps ensure that there is not a secondary or micro angle that is acute or sharp (or too acute or too sharp) such that it creates a weak spot such as a kink, crimp, or other abrupt change in direction, slope, or trajectory of the filar(s), strand, wire, or other portion thereof. The stimulation lead 100 avoids the creation of a weakened (or unintentionally weakened) portion and avoids the potential for failure or fracture at a bend or juncture by ensuring there is always a minimum radius or curvature at any and/or all bend(s), joint(s), juncture(s), and/or junction(s). While the primary angle (or macro angle) between the axis of the anchor and the axis of the lead body may at times be desirably acute or obtuse or any angle as needed for a specific function or phase of use of the lead, the stimulation lead 100 ensures that a secondary angle (or micro angle) will not be created that is sharp, acute, small, or so or too sharp, acute, or small as to weaken a portion of the lead at, near or around that location such that it is weaker than any or all other parts of the lead. While the primary angle (or macro angle) between the axis of the anchor and the axis of the lead body may at times be acute or any angle as needed for a specific function or phase of use of the lead, the stimulation lead 100 ensures that it will avoid over working (and/or weakening) and avoid causing weak part or weak point in the lead by avoiding the creation of secondary angle (or micro angle) that is sharp, acute, small, or so or too sharp, acute, or small as to weaken a portion of the lead at, near or around that location such that it is weaker than any or all other parts of the lead (e.g., the present invention uses a smooth and gentle but strong transition from an uninsulated closed coil or tightly coiled (or tight wound or tightly wound) structure (e.g., in which the neighboring coils of the conductor may touch each other) to an uninsulated straight (or approximately straight) portion of the lead that provides an anchoring function and may be called an anchor or tine, which may also be conductive and deliver stimulation (e.g., electrical stimulation).

In addition to other benefits, the use of an uncoiled anchor 106 maximizes the strength (e.g., the tensile strength) of the anchor such that the tensile strength of the anchor may be the same or greater than the tensile strength of any other portion or aspect of the lead, ensuring that if the rest of the lead may be withdrawn with gentle traction or tension, then the anchor portion may also be withdrawn intact with the same amount or level of tension or traction. This feature provides another benefit to the use such that it enables the user to know, calculate, and/or appreciate the level of tensile force or tension being applied to the anchor and which it can withstand. It also reduces the risk and/or prevents the lead from fracturing at the anchor or at, near or around the bend that forms or begins to form the anchor.

As a nonlimiting example, the angle between the body of the lead (e.g., the electrode, contact, and/or uninsulated portion of the lead) and the anchor of the lead may formed or manufactured to be approximately 90 degrees or in some embodiments between approximately 0 and 180 degrees or between 0 and −180 degrees. This enables the shape and orientation of the lead and/or anchor to be made, changed, and/or adjusted (e.g., overall and/or in relation to each other as needed during the course of manufacturing, packaging (e.g., within an introducer), sterilization, shipping, storage, and/or use (e.g., including different phases or stages of use including introduction, placement, insertion, implant, delivery of stimulation, treatment, and removal). The anchor may be desirably reversibly changeable, adjustable, bendable, and/or flexible to facilitate optimal use of the lead (e.g., in each stage of its use) while avoiding or minimizing damage to tissue (e.g., the tissue in which it is designed to be implanted), the patient, the user, the lead itself, and/or other aspects or portions of the system with which the lead may be used, such as the introducer, needle, cannular, implantation tool(s), and/or introducer system. For example, the anchor 106 may initially be manufactured or positioned at a specific angle or within a prespecified range of angles (e.g., approximately 90 degrees and/or within 80-100 degrees, 70-110 degrees, 60-120 degrees, and/or more than −15, −10, −5, 0, 5, 10, 15, 20, 25, 30, 35, 40, 45, 50, 55, 60, 65, 70, 75, 80, 85, 90, 95, and/or 100 degrees and/or less than 10, 15, 20, 25, 30, 35, 40, 45, 50, 55, 60, 65, 70, 75, 80, 85, 90, 95, 100, 105, 110, 115, 120, 125, 130, and/or 135 degrees) wherein the design of the lead enables the angle, position, and/or orientation of the anchor with respect to the electrode and/or lead body to reversibly change during each phase or stage of use of the lead, such as in the following or subsequent phases or stages of use. Following initial manufacture of the lead (including the initial angle of the anchor and lead body), the angle (and/or orientation of the anchor may be made smaller or more acute (even including negative and/or offset from the midline (e.g., clockwise or counterclockwise or to the left or right of the midline or middle of the lead) if needed) to enable it to fit within a minimally invasive introducer (or needle, tube, cannula, and/or introducer device or system) while avoiding damage or undesirable permanent deformation or distortion (e.g., enabling desirable plastic deformation while avoiding undesirable plastic deformation) to the lead or any portion of the lead or introducer due to the desirable characteristics of the lead design (e.g., avoiding failure or fracture of the lead). The anchor is able to retain each desired angle and orientation as needed during each phase of use while avoiding damage to the lead, tissue, or parts of the device or system. This capability is enabled by the design of (and/or combination of) the filar(s), strand, winding(s), and partial or selective coil (e.g., portion of the lead which is coiled), intentionally straight (e.g., uncoiled) anchor or portion of the anchor (while retaining the desired winding of the filar(s) within the wire and/or strand, and/or joining of the filars, including the weld (e.g., full or partial ball weld) in or at the anchor). When and/or once the lead is packaged, placed, loaded, and/or preloaded into the introducer (or introducer system, needle, cannula, and/or delivery device or system) the anchor may reversibly bend as needed while avoiding damage to the lead and avoiding weakening it. During or once deployed (e.g., after deployment), the anchor may bend again and also desirably resist bending as needed during use in tissue to enable to optimal amount of tissue growth or ingrowth (e.g., to retain or maintain the lead in the correct location to deliver treatment during the treatment period) while preventing undesirable tissue ingrowth and prevent undesirable tissue ingrowth from inhibiting intentional withdrawal of the whole lead intact at the end of treatment or at the end of the treatment period and/or when the user desires removal (e.g., nonsurgical removal or withdrawal of the lead).

In a nonlimiting example, the lead comprises a thin, flexible structure made of a metal and/or polymer material. By "thin," the lead may be approximately or less than 3, 2, 1, 0.9, 0.8, 0.7, 0.6, 0.5, 0.4, 0.3, 0.2, or 0.1 mm or less in diameter (e.g., for the diameter of the coiled lead and/or insulated or uninsulated lead or wire).

The present system may enable the stimulation lead 100 to overcome multiple challenges of the prior art, addressing multiple concerns, and considerations and simultaneously and/or within the same device and/or single design achieve multiple goals and meet many multiple needs (e.g., goals and/or needs that may be competing, conflicting, or in conflict with each other, such that it would be counterintuitive to expect the multiple simultaneous goals to be achieved and combined into the same device design for lead). Examples of the multiple conflicting needs and/or goals include the need for the stimulation lead 100 to be sufficiently flexible, rigid, strong, soft, ductile, and/or hard and to different amounts, magnitudes, and/degrees in each applicable variable, parameter, category, dimension, orientation, direction, angle, and/or specification to achieve what is required to obtain performance superior to all applicable prior art in each goal and category.

As an example, the present system enables the stimulation lead to be sufficiently flexible and strong in all 3 dimension (e.g., X, Y, & Z directions or dimensions) and in combinations or variations of those dimensions to encourage, promote and/or facilitate healthy tissue growth near, in, and/or around the stimulation lead and/or in, at, near, around, or partially around different locations along the stimulation lead or at different parts, portions of the stimulation lead (e.g., the open coil insulated portion of the lead, the more tightly coiled (tight wound) portion of the lead (which may sometimes desirably function as a closed coil and sometimes desirably function as an open coil, depending on the needs and goals of the lead in different scenarios), and the anchor portion of the lead, and/or the transitions between any of these portions or parts of the lead, or other parts or portions of the lead). All of this while also ensuring the lead is sufficiently inflexible or rigid to retain the proper location in tissue (e.g., avoiding, preventing, minimizing, inhibiting, and/or dampening unwanted movement of the lead and/or any part of the lead such as the anchor, electrode, contact, the distal (or far) end of the electrode or contact, the proximal (or close or opposite) end of the electrode or contact while also enabling, allowing, and promoting movement or the ability to move or tolerate movement of a part or any or specific part or parts of the lead, such as the body of the lead, the insulated open coil portion or part of the lead or parts or portions thereof, while promoting movement or the ability to move or tolerate movement of a part or any or specific part or parts of the electrode and/or contact, while promoting movement or the ability to move or tolerate movement of a part or any or specific part or parts of the anchor, while avoiding, preventing, minimizing, inhibiting, and/or dampening unwanted, undesired, deleterious, harmful, movement or pistoning of a part or any or specific part or parts of the lead at, near, or part of the lead exit site or location, such as where the lead transitions from being inside the body, body tissue, and/or skin to being outside the body, tissue and/or skin to avoid, prevent, minimize, inhibit and/or deter ingress of contaminants, germs, bacteria, viruses, and/or other foreign bodies that may cause unwanted or adverse effects, health effects, or events to avoid, prevent, or reduce infection or the risk of infection, irritation, inflammation of the patient, skin, tissue, or body) while also enabling the lead to withstand trauma and multiple various mechanical stresses, strains, challenges, situations, environments, and/or perturbations that may be one time events, occur multiple times in similar or different ways, and/or be repeated, cyclical, and/or almost cyclical, meaning that the present invention is able to withstand, survive, and overcome multiple types, categories, and styles of mechanical forces, impulse force(s), and fatigue challenges including bending, flexing, straining, stressing, twisting, torsion, stretching, pulling, crushing, shearing, and other forces, tests, and/or challenges individually, in combination, and/or repeatedly. These mechanical forces, environments, and challenges, may be represented by mechanical setup(s), fixture(s), and/or test(s) as shown in FIGS. 24A, 24B, 24C and 25, and example of those tests may include a crush or compression test, a stretch or tensile test, a flex or bend test, a torsion or twist test, and/or a shear test.

As an example, if after implantation or implant (after the lead has been deployed and implanted) the stimulation lead is positioned between two hard structures, such as between two bones inside the body or between a bone inside the body and a hard or rigid object outside the body or an material or object outside of the body that may exert or act in a way to exert a force (e.g., a crushing or compressing or compression) on the lead, then the lead (and potentially the tissue in which the lead has been implanted) may experience a type of crushing or compression force. This force may be applied once or multiple times. Another example of a crushing type force may be if a lead is implanted (potentially superficially or deep) at or near the top of the torso and/or near the shoulder and/or between the shoulder and the neck such as where the shoulder strap for a backpack or rucksack may apply force. This helps with lead to withstand, survive, endure, tolerate, and/or overcome such forces, stresses, challenges, and/or such environments while performing correctly and avoiding and/or preventing fracture, loss of function, and/or failure on both a case-by-case basis with an individual lead as well as in small or large quantities or volumes or inventories of leads, meaning that leads can be produced on a large scale of volume or quantities while ensuring their reliability, performance and quality in a large number of patients, overcoming another challenge of the prior art which is consistent performance, integrity, and quality of manufacture, production, deployment, use (e.g., use by physician and patient), and intact removal of the lead(s) on or in a large scale commercial and clinical environment and scenario.

As an example, if after implantation or implant (after the lead has been deployed and implanted) the stimulation lead is positioned in a mobile area of tissue or the body which moves and/or stretches significantly then the lead may be subjected to mechanical stresses and challenges of stretching, tension, and/or pulling, such as tensile or tension forces, which may happen once, at least once, and/or repeatedly multiple times. The stimulation lead of the present system helps enables it to withstand, survive, and overcome these forces and challenges and continue to perform and function correctly while avoiding or preventing loss of function, fracture, and/or failure. As another example, the lead may be subjected to tensile or tension force(s) during removal to enable non-surgical removal of the lead in which the user (e.g., patient, clinician, caregiver, and/or physician) applies tension, traction, and pulls on the lead, and the present system helps the lead to be designed, produced, fabricated, packaged, deployed, and used such that it can withstand multiple types of tension or tensile force, whether the force(s) applied are uncontrolled, abrupt, sudden, or sharp, such as impulse (e.g., such as an intentional, accidental, or unintentional jerk, yank, sudden pull by a user (or untrained user) or an object) or are smooth, gentle, and controlled (e.g., such as by a trained and experience physician).

The present system helps enable the lead to be designed, manufactured, tested, and confirmed to withstand a wide range of uses in multiple scenarios and environments by a wide range of trained and untrained users and continue to function as intended and be used and removed intact without fracture or damage to the lead or the patient or user. The present system also helps enable a lead(s) to be designed, built, manufactured reliably, and repeatedly in small or large volumes or quantities (e.g., to produce a large inventory of leads with consistently high quality) to withstand, survive, endure, tolerate, and/or overcome such forces, stresses, strains challenges, and/or such environments while performing correctly and avoiding and/or preventing fracture, loss of function, and/or failure on both a case-by-case basis with an individual lead as well as in small or large quantities or volumes or inventories of leads, meaning that leads can be produced on a large scale of volume or quantities while ensuring their reliability, performance and quality in a large number of patients, overcoming another challenge of the prior art which is consistent performance, integrity, and quality of manufacture, production, deployment, use (e.g., use by physician and patient), and intact removal of the lead(s) on or in a large scale commercial and clinical environment and scenario.

As an example, if after implantation or implant (after the lead has been deployed and implanted) it is positioned in, at or near a region or area of tissue or the body which bends and/or rotates significantly (e.g., such as a joint, such as a shoulder, hip, elbow, knee, ankle, toe joint, finger joint, and/or other joint, and/or a highly mobile part of the body such as the neck, back, spine, and/or pelvis, and/or near the transition to any of these or similar parts of the body) then the lead may be subjected to mechanical stresses and challenges of bending, flexing, and/or rotating, such as bending, flexion or flexing forces, which may happen once, at least once, and/or repeatedly multiple times, and the present invention enables the lead to withstand, survive, and overcome these forces and challenges and continue to perform and function correctly while avoiding or preventing loss of function, fracture, and/or failure. The present system helps enable the lead to be designed, manufactured, tested, and confirmed to withstand a wide range of uses in multiple scenarios and environments by a wide range of users with a wide range of activity levels (e.g., different levels of exercise, physical therapy, and/or movement or other movement leading to different and potentially very high levels of activity that lead or contribute to high numbers of cycles contributing the potential fatigue challenges that the lead of the present invention can and must overcome) and continue to function as intended and be used and removed intact without fracture or damage to the lead or the patient or user.

The present system also enables a lead(s) to be designed, built, manufactured reliably, and repeatedly in small or large volumes or quantities (e.g., to produce a large inventory of leads with consistently high quality) to withstand, survive, endure, tolerate, and/or overcome such forces, stresses, strains challenges, and/or such environments while performing correctly and avoiding and/or preventing fracture, loss of function, and/or failure on both a case-by-case basis with an individual lead as well as in small or large quantities or volumes or inventories of leads, meaning that leads can be produced on a large scale of volume or quantities while ensuring their reliability, performance and quality in a large number of patients, overcoming another challenge of the prior art which is consistent performance, integrity, and quality of manufacture, production, deployment, use (e.g., use by physician and patient), and intact removal of the lead(s) on or in a large scale commercial and clinical environment and scenario.

As an example, if after implantation or implant (after the lead has been deployed and implanted) it is positioned in, at or near a region or area of tissue or the body which twists (e.g., such as a limb (e.g., arm or leg), torso, and/or a highly mobile part of the body such as the neck, back, spine, and/or pelvis, and/or near the transition to any of these or similar parts of the body) then the lead may be subjected to mechanical stresses and challenges of twisting, and/or torsion, such as torsion forces, which may happen once, at least once, and/or repeatedly multiple times, and the present invention enables the lead to withstand, survive, and overcome these forces and challenges and continue to perform and function correctly while avoiding or preventing loss of function, fracture, and/or failure.

As an example, if after implantation or implant (after the lead has been deployed and implanted) it is positioned in, at or near a region or area of tissue or the body which has at least two different sets of mechanical properties and/or at least two different parts of the body or tissues of groups of muscles or tissue types (e.g., that move differently or relative to each other) then the lead may be subjected to mechanical stresses and challenges of shearing and/or a combination of stretching, bending, crushing, and/or torsion forces, which may happen once, at least once, and/or repeatedly multiple times, and the present invention enables the lead to withstand, survive, and overcome these forces and challenges and continue to perform and function correctly while avoiding or preventing loss of function, fracture, and/or failure.

As another example, the lead may be subjected to mechanical stresses and challenges of shearing and/or a combination of stretching, bending, crushing, and/or torsion forces when the lead crosses tissue planes (e.g., is implanted such that it is partially within at least a first type of tissue, which may have one set, type, or category of mechanical properties and also partially within at least a second type of tissue, which may have another set, type, or category of mechanical properties, and/or it is also possible that the lead may also be partially within at least a third (or more) type of tissue, which may have a third (or more) set, type, or category of mechanical properties). The use of the lead may often require the lead crosses at least one or more tissue planes separating two (or more) types of tissue. An example can be the transition (also sometime called a plane or tissue plane) from skin tissue to adipose (or fat) tissue, connective tissue, and/or muscle tissue; or the transition from tissue plane between adipose (or fat) tissue, connective tissue and/or muscle tissue; or the transition from connective tissue to muscle tissue; or the transition from or tissue plane between connective tissue and muscle tissue; or the transition from or tissue plane between two different muscles, muscle types, muscle groups, muscle tissues, and/or muscle fibers. When the (at least) two types of tissue or two muscles or muscle groups move in opposite directions relative to each other it can create a shear or shearing force on the lead. The lead may be subjected to the resulting forces, which may happen once, at least once, and/or repeatedly multiple times, and the present invention enables the lead to withstand, survive, and overcome these forces and challenges and continue to perform and function correctly while avoiding or preventing loss of function, fracture, and/or failure.

The present system helps enable the lead to be designed, manufactured, tested, and confirmed to withstand a wide range of uses in multiple scenarios and environments by a wide range of users with a wide range of activity levels (e.g., different levels of exercise, physical therapy, and/or movement or other movement leading to different and potentially very high levels of activity that lead or contribute to high numbers of cycles contributing the potential fatigue challenges that the lead of the present invention can and must overcome) and continue to function as intended and be used and removed intact without fracture or damage to the lead or the patient or user. The present system also helps enable a lead(s) to be designed, built, manufactured reliably, and repeatedly in small or large volumes or quantities (e.g., to produce a large inventory of leads with consistently high quality) to withstand, survive, endure, tolerate, and/or overcome such forces, stresses, strains challenges, and/or such environments while performing correctly and avoiding and/or preventing fracture, loss of function, and/or failure on both a case-by-case basis with an individual lead as well as in small or large quantities or volumes or inventories of leads, meaning that leads can be produced on a large scale of volume or quantities while ensuring their reliability, performance and quality in a large number of patients, overcoming another challenge of the prior art which is consistent performance, integrity, and quality of manufacture, production, deployment, use (e.g., use by physician and patient), and intact removal of the lead(s) on or in a large scale commercial and clinical environment and scenario.

As an example, the lead(s) of the present system have undergone a wide range of tests for mechanical stresses, electrical performance and safety, and environmental and mechanical conditions to confirm that the lead(s) can and has overcome the challenges and multiple causes of challenges that have limited of use of existing systems of the prior art, demonstrating that the lead(s) has been successfully designed to resist and/or overcome unwanted movement, migration, fracture, and/or infection and/or the causes and/or contributing factors for unwanted movement, migration, fracture, and/or infection while continuing to function properly to enable, facilitate, and/or make possible uninterrupted delivery of targeted electrical stimulation of a target peripheral nerve to provide therapy, treatment, relief of pain, resolution of symptoms, and/or improvement in quality of life for a patient.

The present system helps enable the anchor 106 to overcome challenges of the prior art (e.g., in which the anchor of the prior art would become encapsulated or surrounded by tissue in such a way that it placed additional and unwanted force and tension on the anchor during any attempt to remove the lead nonsurgically, causing an increase in tensile force that would cause the leads of the prior art to fail, fracture and/or break (often at the bend or transition from the body of the lead or electrode or contact to the anchor, which was pre-weakened by the design of the prior art). The use of a straight, strong, but flexible lead anchor that has several times the strength of the anchor(s) of leads of the prior are while also exhibiting flexibility that far exceeds that of the prior art as well as a reduced profile, footprint, diameter, radius, and/or cross-section (and/or overall reduced profile, footprint, diameter, radius, and/or cross-section) that may be at all locations the same or smaller than the negative space (e.g., the hole or tunnel) created in the tissue (e.g., the outline and/or profile of the lead in the tissue), which when combined with the unique strength and flexibility of the stimulation lead and anchor of the present system, enables it to curve, bend, flex, stretch, and otherwise change shape or dimensions as needed to within the space within the tissue (e.g., where the lead has caused the tissue to grow to but not beyond or within) to be withdrawn (e.g., enabling the lead anchor to curve or bend and slide out through the tunnel of tissue that has formed around the lead). The present system helps overcome the challenges of the prior art (and avoids the creation of a neck, bottleneck, hourglass shape, or narrowing of tissue (e.g., at, near, or around the bend or transition of the anchor) through which the lead anchor of the prior are could not pass or could not pass without risk of fracture or failure or could not pass without risk of fracture or failure in a substantial and nontrivial proportion of leads, cases, instances, and/or patients when the procedure was performed in multiple or many patients). The present system helps overcome these challenges by discouraging the tissue from creating a tunnel of tissue through which the anchor cannot be removed. Said another way, the present systems helps ensure that as it encourages healthy tissue growth in, around, and near the lead it also ensures that the tissue growth that is encouraged does not prevent, inhibit, or challenge the intact removal of the lead including the anchor because the tunnel of tissue that is formed around the lead matches or approximately matches the dimensions, profile, shape, and/or contour of the respective part(s) of the lead.

It is also to be appreciated that the method of fabrication and the design of the anchor ensures that it is at least as strong and/or flexible as all other aspects or portions of the lead, which overcomes a significant challenge of the prior art (e.g., because lead anchors in the prior art were often weaker and/or less flexible than the other parts of the lead due to their design and method of manufacture). As a non-limiting example, the present design overcomes the issues of overworking the metal used in the anchor that would weaken the lead and ensures that the lead anchor maintains maximal strength and flexibility which bench tests have indicated and are consistent with preclinical animal tests exceed the performance of leads of the prior art.

The present system also helps ensure the primary angle between the axis of the lead anchor and the lead body can be achieved as needed and functions as needed while also ensuring the secondary angle at, around, or near the bend or transition of the anchor to the rest of the lead does not become too acute or problematic as to weaken or pre-weaken the lead at that location, further maintaining and maximizing the strength and flexibility of the lead, lead anchor, and portion of the lead a the bend between the anchor and the rest or remainder of the lead, enabling the lead to reliably be removed intact at the end of the intended treatment period despite the presence and challenges of nearby tissue and resulting tension created upon extraction, further enable the lead to be removed non-surgically by both trained and untrained users.

The present system may utilize an optimized pitch or number of revolutions of each aspect of the lead (per distance along a given portion of the lead) to achieve all of the desirable design goals and outcomes. Examples may include the pitch or number of revolutions per unit length of each filar or filar(s) within each lay (e.g., both the first (or inner) lay and second (or outer) lay) and of each strand, wire, and/or portion of the lead within the overall strand, wire, and/or lead in both the insulated open coil portion of the lead and the uninsulated electrode contact portion of the lead. The pitch or number of revolutions per unit length may be critical variables and parameters for multiple aspects of the lead and its features and performance and must be optimized to be neither too high or much nor too low, little, or few.

Further still, the configuration of the stimulation lead 100 allows for use of an insulation displacement connector. An insulation displacement connector is utilized with a lead to connect to the electrical stimulation generator. In the stimulation lead 100 the strength of the multi-filar wire 102 is such that it can withstand the clamping force of the insulation displacement connector necessary to cut through the insulation and not fracture as can occur in prior art systems. Moreover, the configuration of the stimulation lead 100 creates a more reliable connection between the lead and the insulation displacement connector. This also means that the user doesn't need to utilize predetermined lengths of the leads, the stimulation lead 100 may be of any length—it is a one size fits all design. Once the stimulation lead 100 is inserted, implanted or otherwise put into the patient, the user can attach the insulation displacement connector at any appropriate location along the stimulation lead 100 to form a robust and reliable electrical connection. The metal teeth on the insulation displacement connector will cut through the insulation 108 of the stimulation lead 100 to electrically connect with the multi-filar wire 102 so that electrical energy can be passed through the stimulation lead 100 to the patient via the uninsulated portion of the stimulation lead 100, e.g., the electrode 120.

The claims as follows are intended to include all modifications and alterations insofar as they come within the scope of the claims or the equivalent thereof.

Having thus described the invention, the following is claimed:

1. A lead comprising:
an inner core;
an inner layer; and
an outer layer,
wherein a portion of the inner layer is wound in a first orientation and the inner layer comprises a first number of filars of wire,
wherein a portion of the outer layer is wound in a second orientation different from the first orientation and the outer layer comprises a second number of filars of wire, the second number of filars of wire being greater than the first number of filars of wire, wherein a portion of the inner layer and outer layer are wound into a helical coil structure; and an anchor formed by the inner core, inner layer and outer layer extending away from the helical coil structure.

2. The lead of claim 1, wherein the helical coil structure is wound in the first orientation.

3. The lead of claim 1, wherein the helical coil structure comprises insulation.

4. The lead of claim 3, wherein the anchor comprises no helical coil structure.

5. The lead of claim 4, wherein the anchor is bent relative to the helical coil structure between 40 degrees and 100 degrees.

6. The lead of claim 4 further comprising a weld formed on an end of the anchor, wherein the weld prevents the inner core, inner layer and the outer layer from coming apart.

7. The lead of claim 4, wherein the anchor comprises at least a portion of an electrode.

8. The lead of claim 1, wherein the first number of filars of wire comprises between two and ten filars of wire.

9. The lead of claim 1, wherein the second number of filars of wire comprises between seven and fifteen filars of wire.

10. The lead of claim 1, wherein the first number of filars of wire comprises ten filars of wire.

11. The lead of claim 10, wherein the second number of filars of wire comprises fifteen filars of wire.

12. The lead of claim 1, wherein the first orientation comprises a left-hand lay.

13. The lead of claim 12, wherein the second orientation comprises a right-hand lay.

14. The lead of claim 1, wherein the first orientation comprises a right-hand lay.

15. The lead of claim 14, wherein the second orientation comprises a right-hand lay.

16. A lead comprising:
an inner core;
an inner layer; and
an outer layer,
wherein a portion of the inner layer is wound in a first orientation and the inner layer comprises a first number of filars of wire,
wherein a portion of the outer layer is wound in a second orientation different from the first orientation and the outer layer comprises a second number of filars of wire, the second number of filars of wire being greater than the first number of filars of wire, wherein a portion of the inner core extends beyond the inner and outer layers forming an anchor and wherein at least a portion of the anchor is uninsulated forming an electrode.

17. A lead comprising:
an inner core;
an inner layer, wherein at least a portion of a length of the inner layer is wound in a first orientation;
an outer layer, wherein at least a portion of a length of the outer layer is wound in a second orientation different from the first orientation;
wherein the portion of the length of the outer layer and the portion of the length of the inner layer comprise a helical coil structure wound in the first orientation;
insulation covering at least a portion of the helical structure; and
an anchor formed from the inner core, inner layer and outer core and extending from the helical structure, wherein the anchor comprises no helical coil structure.

18. The lead of claim 17, wherein the helical structure comprises a length and a portion of the length of the helical structure is free of the insulation.

19. The lead of claim 18, wherein the portion of the length of the helical structure free of the insulation comprises an electrode.

20. The lead of claim 17, wherein the anchor is bent relative to the helical coil structure between about 40 degrees and 100 degrees.

21. The lead of claim 17, wherein the inner layer comprises a first number of filars of wire of between two and ten filars of wire.

22. The lead of claim 21, wherein the outer layer comprises a second number of filars of wire of between seven and fifteen filars of wire.

23. The lead of claim 17, wherein the inner layer comprises ten filars of wire.

24. The lead of claim 23, wherein the outer layer comprises fifteen filars of wire.

25. The lead of claim 17 further comprising a weld formed on an end of the anchor, wherein the weld prevents the inner core, inner layer and the outer layer from coming apart.

26. The lead of claim 17, wherein the first orientation comprises a left-hand lay.

27. The lead of claim 17, wherein the first orientation comprises a right-hand lay.

28. A lead comprising:

an inner core comprising a single filar;

an inner layer wound in a first orientation around the inner core;

an outer layer wound in a second orientation opposite the first orientation;

insulation covering a portion of a length of the outer layer and inner layer and a portion of a length of the inner core, wherein the insulation, the portion of the length of the outer layer and inner layer and the portion of the length of the inner core comprise a helical coil structure; and an anchor formed by the inner core, the inner layer and the outer layer, wherein the anchor comprises no helical coil structure.

29. The lead of claim 28, wherein the helical coil structure is wound in the first orientation.

30. The lead of claim 29, wherein the helical structure comprises a length and a portion of the length of the helical structure is free of the insulation.

31. The lead of claim 30, wherein the portion of the length of the helical structure free of the insulation comprises an electrode.

32. The lead of claim 31, wherein the anchor is bent relative to the helical coil structure between about 40 degrees and 100 degrees.

33. The lead of claim 32, wherein the inner layer comprises a first number of filars of wire of between two and ten filars of wire.

34. The lead of claim 33, wherein the outer layer comprises a second number of filars of wire of between seven and fifteen filars of wire.

35. The lead of claim 34 further comprising a weld formed on an end of the anchor, wherein the weld prevents the inner core, inner layer and the outer layer from coming apart.

36. The lead of claim 35, wherein the first orientation comprises a left-hand lay.

37. The lead of claim 35, wherein the first orientation comprises a right-hand lay.

\* \* \* \* \*